US012734180B2

(12) United States Patent
Quinten et al.

(10) Patent No.: US 12,734,180 B2
(45) Date of Patent: Sep. 15, 2026

(54) TREATMENT OF PROSTATE CANCER WITH A COMBINATION OF ABIRATERONE ACETATE, NIRAPARIB TOSYLATE MONOHYDRATE AND PREDNISONE

(71) Applicant: Janssen Pharmaceutica NV, Beerse (BE)

(72) Inventors: Thomas Ronald A. Quinten, Zeveneken (BE); Urbain Alfons C. Delaet, Balen (BE); Philip Erna H. Heyns, Vosselaar (BE); Tatiana Marcozzi, Borgerhout (BE); Johny Bertels, Mol (BE); Katrien Luyten, Oud-Turnhout (BE); Kaustubh Ramesh Tambwekar, Geel (BE); Angela Lopez-Gitlitz, Los Angeles, CA (US); Paul J. A. Hartman Kok, Eersel (NL)

(73) Assignee: Janssen Pharmaceutica NV, Beerse (BE)

( * ) Notice: Subject to any disclaimer, the term of this patent is extended or adjusted under 35 U.S.C. 154(b) by 876 days.

(21) Appl. No.: 17/998,198

(22) PCT Filed: May 7, 2021

(86) PCT No.: PCT/EP2021/062180
§ 371 (c)(1),
(2) Date: Nov. 8, 2022

(87) PCT Pub. No.: WO2021/224467
PCT Pub. Date: Nov. 11, 2021

(65) Prior Publication Data

US 2023/0218640 A1 Jul. 13, 2023

Related U.S. Application Data

(60) Provisional application No. 63/142,919, filed on Jan. 28, 2021, provisional application No. 63/174,282, filed on Apr. 13, 2021.

(30) Foreign Application Priority Data

May 8, 2020 (EP) .................................... 20173749

(51) Int. Cl.

| | |
|---|---|
| ***A61K 31/58*** | (2006.01) |
| ***A61K 9/16*** | (2006.01) |
| ***A61K 9/20*** | (2006.01) |
| ***A61K 9/28*** | (2006.01) |
| ***A61K 31/454*** | (2006.01) |
| ***A61K 31/573*** | (2006.01) |
| ***A61K 38/25*** | (2006.01) |
| ***A61P 13/08*** | (2006.01) |
| ***A61P 15/00*** | (2006.01) |
| ***A61P 35/00*** | (2006.01) |
| ***A61P 35/04*** | (2006.01) |

(52) U.S. Cl.
CPC ............ *A61K 31/58* (2013.01); *A61K 9/1617* (2013.01); *A61K 9/1635* (2013.01); *A61K 9/1694* (2013.01); *A61K 9/2009* (2013.01); *A61K 9/2013* (2013.01); *A61K 9/2018* (2013.01); *A61K 9/2027* (2013.01); *A61K 9/2054* (2013.01); *A61K 9/28* (2013.01); *A61K 31/454* (2013.01); *A61K 31/573* (2013.01); *A61K 38/25* (2013.01); *A61P 13/08* (2018.01); *A61P 15/00* (2018.01); *A61P 35/00* (2018.01); *A61P 35/04* (2018.01)

(58) Field of Classification Search
CPC ................................ A61K 31/58; A61P 13/08
See application file for complete search history.

(56) References Cited

U.S. PATENT DOCUMENTS

| | | | |
|---|---|---|---|
| 4,717,721 | A | 1/1988 | Deluca et al. |
| 4,851,401 | A | 7/1989 | Deluca et al. |
| 4,857,518 | A | 8/1989 | Deluca et al. |
| 4,866,048 | A | 9/1989 | Calverley et al. |
| 5,120,722 | A | 6/1992 | Baggiolini et al. |
| 5,145,846 | A | 9/1992 | Baggiolini et al. |
| 5,190,935 | A | 3/1993 | Binderup et al. |
| 5,237,110 | A | 8/1993 | Deluca et al. |
| 5,411,949 | A | 5/1995 | Neef et al. |
| 5,446,035 | A | 8/1995 | Neef et al. |
| 5,547,947 | A | 8/1996 | Dore et al. |
| 5,604,213 | A | 2/1997 | Barrie et al. |
| 5,618,807 | A | 4/1997 | Barrie et al. |
| 5,688,977 | A | 11/1997 | Sisti et al. |
| 6,087,350 | A | 7/2000 | Johnson et al. |
| 6,310,226 | B1 | 10/2001 | Calverley et al. |
| 6,521,608 | B1 | 2/2003 | Henner et al. |

(Continued)

FOREIGN PATENT DOCUMENTS

| | | | |
|---|---|---|---|
| CN | 101528308 | A | 9/2009 |
| CN | 104306977 | A | 1/2015 |

(Continued)

OTHER PUBLICATIONS

FDA Reference ID: 4600207, 2017. (Year: 2017).*

(Continued)

*Primary Examiner* — Elly-Gerald Stoica
(74) *Attorney, Agent, or Firm* — BakerHostetler

(57) ABSTRACT

The present disclosure relates to a combination of abiraterone acetate and niraparib, free-dose and fixed-dose combinations of abiraterone acetate and niraparib, and methods of treatment of prostate cancer with said combinations.

18 Claims, 7 Drawing Sheets

(56) References Cited

Figure 1:
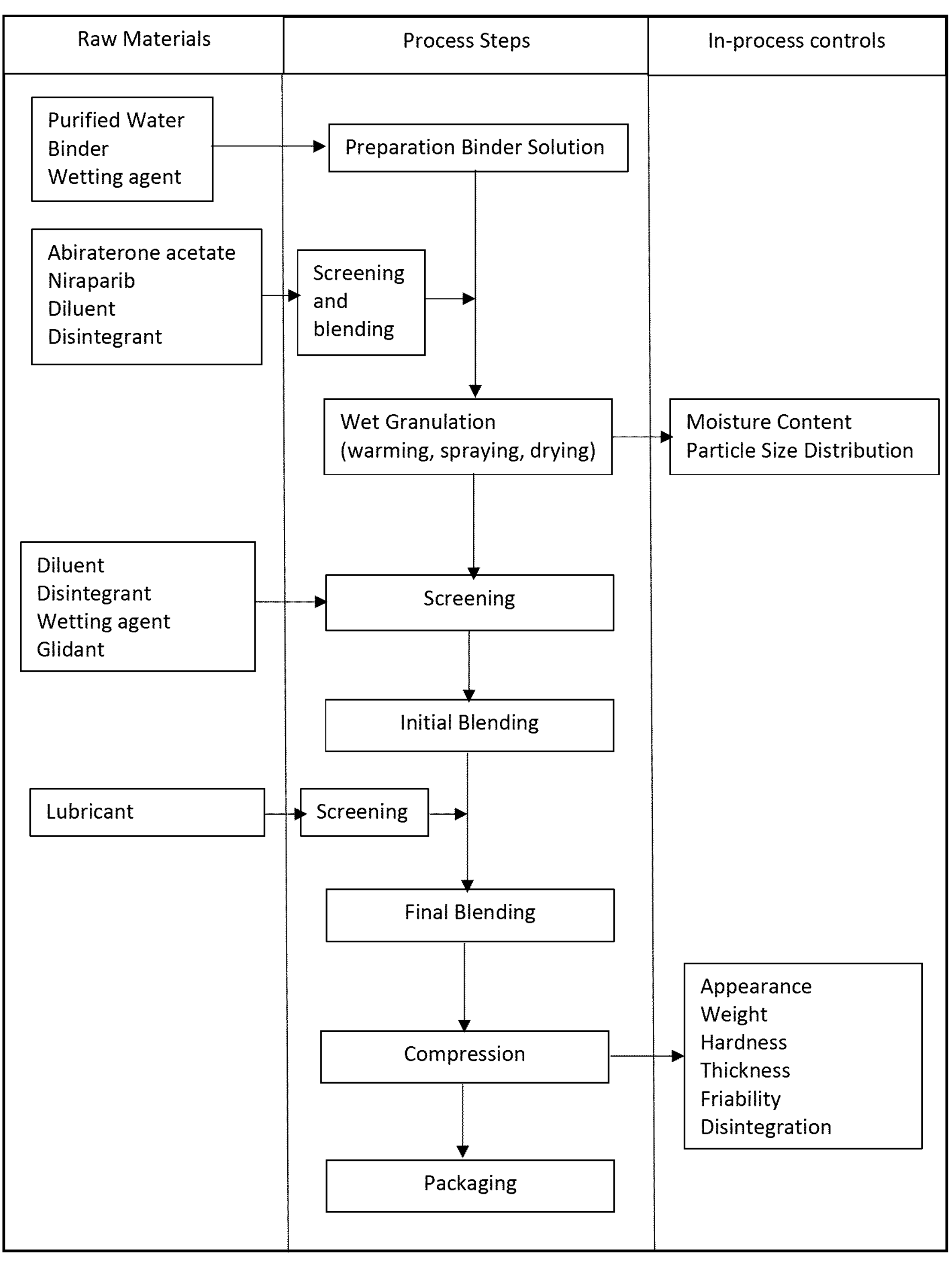

U.S. PATENT DOCUMENTS 6,559,139 B1 5/2003 Johnson et al.
6,872,568 B1 3/2005 Ni et al.
7,071,333 B2 7/2006 Combs et al.
7,256,193 B2 8/2007 Kyle et al.
7,482,334 B2 1/2009 Frincke et al.
7,547,687 B2 6/2009 Reading et al.
7,709,517 B2 5/2010 Sawyers et al.
7,879,352 B2 2/2011 Solomon et al.
8,071,623 B2 12/2011 Jones et al.
8,183,274 B2 5/2012 Sawyers et al.
8,436,185 B2 5/2013 Foley et al.
8,658,128 B2 2/2014 Altschul et al.
8,822,438 B2 9/2014 Auerbach et al.
9,114,147 B2 8/2015 Altschul et al.
9,126,941 B2 9/2015 Sawyers et al.
9,295,680 B2 3/2016 Altschul et al.
9,314,473 B2 4/2016 Altschul et al.
9,320,747 B1 4/2016 Altschul et al.
9,598,459 B2 3/2017 Altschul et al.
9,636,351 B2 5/2017 Altschul et al.
9,642,866 B2 5/2017 Altschul et al.
9,855,284 B2 1/2018 Altschul et al.
9,861,643 B2 1/2018 Altschul et al.
10,058,563 B2 8/2018 Altschul et al.
10,076,528 B2 9/2018 Altschul et al.
10,231,982 B2 3/2019 Altschul et al.
10,238,666 B2 3/2019 Altschul et al.
10,517,881 B2 12/2019 Altschul et al.
10,537,586 B2 1/2020 Altschul et al.
11,040,037 B2 6/2021 Altschul et al.
11,207,311 B2 12/2021 Gottardis et al.
11,224,599 B2 1/2022 Altschul et al.
11,364,252 B2 6/2022 Altschul et al.
11,576,921 B2 2/2023 Altschul et al.
2002/0128240 A1 9/2002 Mazess
2003/0083231 A1 5/2003 Ahlem et al.
2003/0119795 A1 6/2003 Henner et al.
2004/0138187 A1 7/2004 Reading et al.
2005/0020546 A1 1/2005 Laidlaw et al.
2005/0054620 A1 3/2005 Koeffler et al.
2005/0101581 A1 5/2005 Reading et al.
2005/0233958 A1 10/2005 Ni et al.
2006/0003021 A1 1/2006 Strugnell et al.
2006/0003950 A1 1/2006 Strugnell et al.
2006/0018933 A1 1/2006 Vaya et al.
2006/0018934 A1 1/2006 Vaya et al.
2006/0024365 A1 2/2006 Vaya et al.
2006/0030608 A1 2/2006 Nelson et al.
2007/0203107 A1 8/2007 Fricke et al.
2007/0213309 A1 9/2007 Reading et al.
2007/0265236 A1 11/2007 Reading et al.
2007/0275937 A1 11/2007 Reading et al.
2007/0275938 A1 11/2007 Reading et al.
2008/0004286 A1 1/2008 Wang et al.
2008/0004287 A1 1/2008 Ma et al.
2008/0051375 A1 2/2008 Auerbach et al.
2008/0085873 A1 4/2008 Reading et al.
2008/0138426 A1 6/2008 Hara et al.
2008/0167345 A1 7/2008 Jones et al.
2009/0124587 A1 5/2009 Auerbach et al.
2012/0046330 A1 2/2012 Alargova et al.
2012/0201747 A1 8/2012 Altschul et al.
2014/0107086 A1 4/2014 Theise et al.
2014/0315920 A1 10/2014 Mrca et al.
2014/0336154 A1 11/2014 Do et al.
2014/0336157 A1 11/2014 Auerbach et al.
2015/0344968 A1 12/2015 Johnson
2015/0366881 A1 12/2015 Altschul et al.
2015/0366882 A1 12/2015 Altschul et al.
2016/0015816 A1 1/2016 Benjamin et al.
2016/0113948 A1 4/2016 Altschul et al.
2016/0160294 A1 6/2016 Wilcoxen et al.
2016/0279148 A1 9/2016 Altschul et al.
2016/0279149 A1 9/2016 Altschul et al.
2017/0051007 A1 2/2017 Altschul et al.
2017/0128465 A1 5/2017 Altschul et al.
2017/0202859 A1 7/2017 Altschul et al.
2017/0232005 A1 8/2017 Altschul et al.
2017/0354665 A1 12/2017 Bosch et al.
2018/0017438 A1 1/2018 Crohn et al.
2018/0028521 A1 2/2018 Gottardis et al.
2018/0117066 A1 5/2018 Altschul et al.
2018/0185392 A1 7/2018 Altschul et al.
2018/0296574 A1 10/2018 Snyder et al.
2018/0311224 A1 11/2018 Hedley et al.
2018/0325920 A1 11/2018 Altschul et al.
2018/0360852 A1 12/2018 Altschul et al.
2019/0022079 A1 1/2019 Gottardis et al.
2019/0134062 A1 5/2019 Altschul et al.
2019/0151335 A1 5/2019 Altschul et al.
2019/0381038 A1 12/2019 Altschul et al.
2020/0101087 A1 4/2020 Altschul et al.
2021/0353623 A1 11/2021 Altschul et al.
2021/0361675 A1 11/2021 Altschul et al.
2022/0071980 A1 3/2022 Gottardis et al.
2022/0175801 A1 6/2022 Snyder et al.
2022/0298203 A1 9/2022 Altschul et al.
2023/0142627 A1 5/2023 Altshul et al.
2024/0245710 A1 7/2024 Snyder et al.

FOREIGN PATENT DOCUMENTS

CN 108514550 A 9/2018
DE 10061137 A1 6/2002
EP 0413270 A2 2/1991
EP 0912535 A1 5/1999
EP 0914116 A1 5/1999
EP 1140192 A2 10/2001
EP 1336602 A1 8/2003
EP 1379246 A1 1/2004
EP 1385514 A1 2/2004
EP 1385515 A1 2/2004
EP 1385518 A1 2/2004
EP 1423381 A1 6/2004
EP 1463733 A2 10/2004
EP 1466628 A1 10/2004
EP 1487829 A1 12/2004
EP 1515949 A1 3/2005
EP 1556354 A2 7/2005
EP 1562932 A1 8/2005
EP 1562936 A2 8/2005
EP 1572299 A1 9/2005
EP 1583524 A1 10/2005
EP 1583763 A1 10/2005
EP 1598338 A1 11/2005
EP 1598339 A1 11/2005
EP 1598340 A1 11/2005
EP 1631285 A1 3/2006
EP 1307197 B1 4/2006
EP 1648879 A1 4/2006
EP 1664016 A2 6/2006
EP 1664041 A1 6/2006
EP 1674479 A1 6/2006
EP 1676577 A1 7/2006
EP 1803718 A1 7/2007
EP 1810970 A1 7/2007
EP 1412368 B1 8/2007
EP 1673092 B1 8/2007
EP 1862458 A2 12/2007
EP 1867644 A1 12/2007
EP 1918279 A2 5/2008
EP 1927858 A1 6/2008
EP 1930322 A1 6/2008
EP 1942106 A1 7/2008
EP 1975164 A2 10/2008
EP 2336120 A1 6/2011
EP 2478907 A2 7/2012
EP 2061561 B1 7/2013
EP 2805945 A1 11/2014
EP 2007733 B1 5/2016
EP 3578266 B1 6/2024
JP 2003-104888 A 4/2003
JP 2003-525254 A 8/2003
JP 2006-515623 A 6/2006

(56) References Cited

FOREIGN PATENT DOCUMENTS

| | | | |
|---|---|---|---|
| JP | 2010-501575 | A | 1/2010 |
| JP | 2010-506846 | A | 3/2010 |
| JP | 2010-515715 | A | 5/2010 |
| JP | 2011-512349 | A | 4/2011 |
| JP | 2013-536231 | A | 9/2013 |
| WO | 92/00992 | A1 | 1/1992 |
| WO | 93/20097 | A1 | 10/1993 |
| WO | 95/09178 | A1 | 4/1995 |
| WO | 01/64251 | A2 | 9/2001 |
| WO | 01/81364 | A1 | 11/2001 |
| WO | 01/93836 | A2 | 12/2001 |
| WO | 02/03286 | A1 | 1/2002 |
| WO | 02/32861 | A2 | 4/2002 |
| WO | 02/53138 | A2 | 7/2002 |
| WO | 02/85355 | A1 | 10/2002 |
| WO | 02/85361 | A1 | 10/2002 |
| WO | 02/91993 | A2 | 11/2002 |
| WO | 2002/102783 | A1 | 12/2002 |
| WO | 03/20699 | A2 | 3/2003 |
| WO | 03/22835 | A1 | 3/2003 |
| WO | 03/37252 | A2 | 5/2003 |
| WO | 03/39460 | A2 | 5/2003 |
| WO | 03/86388 | A1 | 10/2003 |
| WO | 03/86404 | A1 | 10/2003 |
| WO | 03/92595 | A2 | 11/2003 |
| WO | 2004/012699 | A2 | 2/2004 |
| WO | 2004/012700 | A2 | 2/2004 |
| WO | 2004/016753 | A2 | 2/2004 |
| WO | 2004/037269 | A1 | 5/2004 |
| WO | 2004/041164 | A2 | 5/2004 |
| WO | 2004/062620 | A2 | 7/2004 |
| WO | 2005/016236 | A2 | 2/2005 |
| WO | 2005/021487 | A1 | 3/2005 |
| WO | 2005/107801 | A2 | 11/2005 |
| WO | 2006/004917 | A2 | 1/2006 |
| WO | 2006/021776 | A1 | 3/2006 |
| WO | 2006/027266 | A1 | 3/2006 |
| WO | 2006/050402 | A1 | 5/2006 |
| WO | 2006/081152 | A2 | 8/2006 |
| WO | 2006/116217 | A2 | 11/2006 |
| WO | 2006/116716 | A2 | 11/2006 |
| WO | 2007/014327 | A2 | 2/2007 |
| WO | 2008/024484 | A1 | 2/2008 |
| WO | 2008/039254 | A2 | 4/2008 |
| WO | 2008/048802 | A1 | 4/2008 |
| WO | 2008/062466 | A2 | 5/2008 |
| WO | 2008/084261 | A1 | 7/2008 |
| WO | 2008/100985 | A2 | 8/2008 |
| WO | 2008/109740 | A2 | 9/2008 |
| WO | 2008/127290 | A2 | 10/2008 |
| WO | 2009/087381 | A1 | 7/2009 |
| WO | 2009/122431 | A2 | 10/2009 |
| WO | 2012/009475 | A1 | 1/2012 |
| WO | 2012/027247 | A2 | 3/2012 |
| WO | 2012/106514 | A2 | 8/2012 |
| WO | 2014/089324 | A1 | 6/2014 |
| WO | 2015/032873 | A1 | 3/2015 |
| WO | 2015/164586 | A1 | 10/2015 |
| WO | 2016/001208 | A1 | 1/2016 |
| WO | 2016/044701 | A1 | 3/2016 |
| WO | 2016/094391 | A1 | 6/2016 |
| WO | 2017/023694 | A1 | 2/2017 |
| WO | 2018/050131 | A1 | 3/2018 |
| WO | 2018/067520 | A2 | 4/2018 |
| WO | 2018/183354 | A1 | 10/2018 |
| WO | 2018/191141 | A1 | 10/2018 |
| WO | 2019/067634 | A1 | 4/2019 |
| WO | 2019/074536 | A1 | 4/2019 |
| WO | 2019/206472 | A1 | 10/2019 |
| WO | 2020/072797 | A1 | 4/2020 |

OTHER PUBLICATIONS

"A Safety and Pharmacokinetics Study of Niraparib Plus an Androgen Receptor-Targeted Therapy in Men With Metastatic Castration-Resistant Prostate Cancer (BEDIVERE)", NCT02924766, Version 9, Feb. 1, 2018, 10 pages.

"A Safety and Pharmacokinetics Study of Niraparib Plus an Androgen Receptor-Targeted Therapy in Men With Metastatic Castration Resistant Prostate Cancer (BEDIVERE)", NCT02924766, Jul. 26, 2019, Version 17, Jul. 26, 2019, 4 pages.

"A Safety and Pharmacokinetics Study of Niraparib Plus an Androgen Receptor-Targeted Therapy in Men With Metastatic Castratio .· Resistant Prostate Cancer (BEDIVERE)", NCT02924766 Version 4, May 12, 2017, 4 pages.

"A Safety and Pharmacokinetics Study of Niraparib Plus Apalutamide in Men With Metastatic Castration-Resistant Prostate Cancer (BEDIVERE)", NCT02924766, Version 2 Clinical Trail Nov. 3, 2016, 8 pages.

"A Safety and Pharmacokinetics Study of Niraparib Plus Apalutamide in Men With Metastatic Castration-Resistant Prostate Cancer (BEDIVERE)", NCT02924766 Version 1, Oct. 4, 2016, 8 pages.

"A Study of Niraparib in Combination With Abiraterone Acetate and Prednisone Versus Abiraterone Acetate and Prednisone for Treatment of Participants With Metastatic Prostate Cancer (MAGNITUDE)". Study NCT03748641, Retrieved from https://classic.clinicaltrials.gov/ct2/history/NCT03748641?V_19=View#StudyPageTop, Apr. 2, 2020, pp. 23.

"Abiraterone/Prednisone, Olaparib, or Abiraterone/Prednisone + Olaparib in Patients With Metastatic Castratio•• Resistant Prostate Cancer With DNA Repair Defects ", NCT03012321, Version 5, Feb. 8, 2017, 13 pages.

"Akeega EMA SmPC," Summary of product characteristics, First published: Feb. 6, 2023, pp. 1-57.

"Corticosteroid Conversion Calculator", Retrieved from https://clincalc.com/Corticosteroids/, Oct. 24, 2015, 4 Pages.

"Description of VCaP cell line," Cellosaurus, First creation date: Apr. 4, 2012, pp. 1-4.

"Final Multivariate Analysis from the Phase 3 MAGNITUDE Study Shows Trend Toward Improvement in Overall Survival in Patients with Metastatic Castration-Resistant Prostate Cancer with BRCA Alterations Treated with Niraparib and Abiraterone Acetate Plus Prednisone", Oct. 22, 2023, 12 Pages.

"Gynaecological Cancers: Biology and Therapeutics," RCOG, 2011, p. 92.

"Late-Stage Prostate Cancer Treatment Strengthens Oncology Pipeline," Johnson & Johnson Completes Acquisition of Aragon Pharmaceuticals, Inc., Aug. 19, 2013, Retrieved from https://www.jnj.com/media-center/press-releases/johnson-johnson-completes-acquisition-of-aragon-pharmaceuticals-inc, pp. 5.

"Ph II Study to Evaluate Olaparib With Abiraterone in Treating Metastatic Castration Resistant Prostate Cancer", NCT01972217, Version 27, Feb. 2, 2017, 19 pages.

2011 Zytiga(Registered) Approval Prescribing Information, ZYTIGA(Trademarks), (abiraterone acetate) Tablets for Oral Administration Initial U.S. Approval—2011, Apr. 2011, 22 pages.

A Phase 3, Randomized, Double-Blind, Placebo-Controlled Study of Abiraterone Acetate (CB7630) Plus Prednisone in Patients with Metastatic Castration-Resistant Prostate Cancer Who Have Failed Docetaxel-Based Chemotherapy, Clinical Genitourinary Cancer, vol. 6(2):140 (2008).

Abad et al., "Male pseudohermaphroditism with 17 alpha-hydroxylase deficiency", A case report, Br. J. Obstet. Gynaecol., Dec. 1980, vol. 87 No. 12, 1162-1165.

Abida, Wassim, et al., "Targeting DNA Repair in Prostate Cancer", Journal of Clinical Oncology, American Society of Clinical Oncology, Apirl 1, 2018, vol. 36, No. 10, pp. 1017-1021.

Abiraterone Acetate: Abbreviated Clinical Study Report Synopsis COU-AA-BE (Doc. EDMS-ERI-13494974:2.0) (Be Synopsis) 2010, 5 pages.

Abiraterone: A Story of Scientific Innovation and Commercial Partnership, http://www.icr.ac.uk/news-features/latestfeatures/abiraterone-a-story-of-scientific-innovation-andcommercial-artnership, Dec. 19, 2016, pp. 1-14.

(56) References Cited

OTHER PUBLICATIONS

About ZYTIGA (Registered) Abiraterone acetate, retrieved from https://www.zytiga.com/choos ing-zytiga#how-zytiga-works, on Jul. 25, 2017, 7 pages.
Academy of Managed Care Pharmacy (AMCP) Nexus 2016, National Harbor, MD, USA; Oct. 3-6, 2016 filed for Janssen IPR2016-01332.
Aggarwal et al., "Development of Abiraterone Acetate, a 17-alpha Hydroxylase C17,20-Lyase Inhibitor as a Secondary Hormonal Therapy in Prostate Cancer," Update on Cancer Therapeutics, vol. 2:171-175 (2007).
Altman et al., "The Revised CONSORT Statement for Reporting Randomized Trials: Explanation and Elaboration", Annals of Internal Medicine vol. 134, No. 8, Apr. 17, 2001, pp. 663-694.
Amended marketing authorization for Zytiga, European Commission, Nov. 9, 2016, pp. 74.
Anlonarakis et al., "Phase III Trials With Docetaxel-Based Combinations for Metastatic Castration-Resistant Prostate Cancer: Time to Learn From Past Experiences" Journal of Clinical Oncology, vol. 31, Ne 14. May 10, 2013: pp. 1709-1712.
Annane D et al., "Effect of treatment with low doses of hydrocortisone and fludrocortisone on mortality in patients with septic shock", JAMA, Aug. 21, 2002, vol. 288, No. 7, pp. 862-871.
Anonymous: "NCT00485303—An Efficacy and Safety Study of Abiraterone Acetate and Prednisone in Participants With Prostate Cancer Who Failed Androgen Deprivation and Docetaxel- Based Chemotherapy", Jun. 2007, 3 pages.
Antifungal Treatment Should Be Taken Off the Market, Public Citizen Tells FDA filed for Case# IPR2016-01582 on Feb. 24, 2015, 1 page.
Antolin et al., "Linking off-target kinase pharmacology to the differential cellular effects observed among PARP inhibitors", Oncotarget, vol. 5, No. 10, May 2014, pp. 3023-3028.
Antolin et al., "The kinase polypharmacology landscape of clinical PARP inhibitors", Scientific Reports, vol. 10, Article No. 2585, 2020, pp. 14.
Arinc et al.., "Molecular Aspects of Monooxygenases and Bioactivation of Toxic Compounds". Series A: Life Sciences vol. 202 Mylan Pharms. Inc., 1989, 28 pages.
Arlt, W. et al., "Adrenal insufficiency," Lancet, vol. 361 May 31, 2003, pp. 1881-1893.
Armstrong and Carducci. "New drugs in prostate cancer," Current Opinions Urology, 2006, Filed for Case IPR2016-00286, Janssen Exhibit 2011, vol. 16, pp. 138-145.
Armstrong et al., "New Drug Development in Metastatic Prostate Cancer," Urologic Oncology: Seminars and Original Investigations, vol. 26: 430-437 (2008).
ASCO Cancer Foundation, Poster Session F: Hormone Refractory, ASCO, 2005.
Asim et al. AR signaling and parp inhibition synergize; olaparib inhibited growth of PC3 prostate tumors; Nature comm 8:374; 2017.
Assessment Report for Zytiga (abiraterone) published 2011 by the CHMP of the EMA.
Attard el al.. "Prostate Cancer's Day in the Sun." BMJ, vol. 337: a1256 (2008).
Attard et al., Activity, toxicity, and effect on steroid precursor levels of abiraterone (A), an oral irreversible inhibitor of CYP17 (17Alpha-hydroxylase/1720, lyase), in castrate men with castration refractory prostate cancer (CRPC): 2007 Prostate Cancer Symposium, Abstract No. 264.
Attard et al., "Antitumor Activity with CYP17 Blockade Indicates That Castration-Resistant Prostate Cancer Frequently Remains Hormone Driven", Cancer Res 2009, vol. 69, No. 12, Jun. 15, 2009, pp. 4937-4940.
Attard et al., "Dissecting Prostate Carcinogenesis Through ETS Gene Rearrangement Studies: Implications for Anticancer Drug Development," J. Clin. Pathol, vol. 61:891-896 (2008).
Attard et al., "Improving the outcome of Patients with Castration-Resistant Prostate Cancer Through Rational Drug Development," British Journal of Cancer, vol. 95:767-774 (2006).
Attard et al., "Management Strategies for Hormone-Refractory Prostate Cancer", Therapy in Practice, Arn. J. 2006,. Volume 5, No. 3, pp. 163-169.
Attard et al., "Phase | Clinical Trial of a Selective Inhibitor of CYP17, Abiraterone Acetate, Confirms That Castration-Resistant Prostate Cancer Commonly Remains Hormone Driven." J. Glin. Oncol., vol. 26(26):4563-4571 (2008).
Attard et al., "Phasel study of continuous oral dosing of an irreversible CYP17 inhibitor, abiraterone (A), in castration refractory prostate cancer (CRPC) patients (p) incorporating the evaluation of androgens and steroid metabolites in plasma and tumor," J. Clin. Oncology, 2007 ASCO Annual Meeting Proceedings Part I, vol. 25(188), Abstract No. 5063.
Attard et al., "Predictors of Response and Pharmacodynamic (PD) Endpoints in a Phase I and Pharmacokinetic Study of Abiraterone Acetate (AA) in Castration-Resistant Prostate Cancer (CRPC)," ASCO 2008 Genitourinary Cancers Symposium, abstract No. 214 (2008).
Attard et al., "Selective blockade of androgenic steroid synthesis by novel lyase inhibitors as a therapeutic strategy for treating metastatic prostate cancer," BJU International, vol. 96, pp. 1241-1246 (2005).
Attard et al., "Selective Inhibition of CYP17 with Abiraterone Acetate is Well Tolerated and Results in a High Response Rate in Castration-Resistant Prostate Cancer (CRPC)," Molecular Cancer Therapeutics (Dec. 2007), vol. 6(12): 3455s, 2007 AACR-NCI-EORTC International Conference, Poster Session B, abstract No. B73 (2007).
Attard et al., "Selective Inhibition of CYP17 With Abiraterone Acetate Is Highly Active in the Treatment of Castration-Resistant Prostate Cancer," Journal of Clinical Oncology, Filed for Case IPR2016-002B6, Janssen Exhibit 2015, vol. 27, No. 23, on Aug. 10, 2009, pp. 3742-3748.
Attard et al., Steroid Hormone Receptors in Prostate Cancer: A Hard Habit to Break?, Cancer Cell, vol. 16, Dec. 8, 2009, pges 458-462.
Attard et al... "Abiraterone Acetate Is Well", Journal of Clinical Oncology, vol. 28, No. 29, Oct. 10, 2010. pp. e560-e561.
Attard et al... Abiraterone, an oral, irreversible CYP450C17 enzyme inhibitor appears In have activity in post-docetaxel castration refractory prostate cancer (CRPC) patients (pts). Annals of Oncology, vol. 18(Supplement 9): ix173-ix174. Abstract No. 51PD (2007).
Attard G et al., "Clinical and biochemical consequences of CYP17A1 inhibition with abiraterone given with and without exogenous glucocorticoids in castrate men with advanced prostate cancer". Journal of Clinical Endocrinol Metab Feb. 2012, vol. 97 No. 2 pp. 507-516.
Attard, Poster: A randomized trial of abiraterone acetate (AA) administered with 1 of 4 glucocorticoid (GC) regimens in metastatic castration-resistant prostate cancer (mCRPC) patients (pts). J. Clin Oncol 34, 2016 (Suppl 2S: abstr 261). pp. 1-4, Nov. 15, 2016.
Auches et al., "Use of Prednisone With Abiraterone Acetate in Metastatic Castration-Resistant Prostate Cancer", The Oncologist, vol. 19, No. 12, Oct. 31, 2014 (Oct. 31, 2014), pp. 1231-1240,.
Auchus et al., "Human steroid biosynthesis for the oncologist", NIH Public Access, J Investing Med. Author manuscript: available in PMC May 14, 2013, 22 pages.
Auchus, R.J. "The genetics, pathophysiology, and management of human deficiencies of P450c17," Endocrinology and Metabolism. Clinics of North America. vol. 30, No. 1, pp. 101-119, Mar. 2001.
Auerbach et al., United States Patent and Trademark Office, Before the Patent Trial and Appeal Board, Amerigen Pharmaceuticals Limited and Argentum Pharmaceuticals LLC (Petitioners), Janssen Oncology, Inc. (Patent Owner) for U.S. Pat. No. 8,822,438, "Methods and Compositions for Treating Cancer", filed for Case IPR2016-01582, Amerigen Exhibit 2019 Issued on Sep. 2, 2014, 13 pages.
Austin et al., "A Brief note on overlapping confidence intervals", Mylan vs. Janssen, Filed for Case IPR2016-01332, , Janssen Exhibit 2184, on 2002, Journal of Vascular Surgery, vol. 36, No. 1, 194-195 pages.
Ayub, M., Inhibition of testicular 17a-hydroxylase and 17,20-lyase but not 3B-hydroxysteroid dehydrogenase-isomerase or 17B-hydroxysteroid oxidoreductase by ketoconazole and other imidazole drugs, Journal of Steroid Biochemistry (1987) 28(5), p. 521-531.

(56) References Cited

OTHER PUBLICATIONS

Azad et al., "Outcomes with Abiraterone Acetate in Metastatic Castration-resistant Prostate Cancer Patients Who Have Poor Performance Status", European Urology, vol. 67, Issue 3, Mar. 2015, pp. 441-447.

Balaji, Managing Metastatic Prostate Cancer in Your Urological Oncology Practice (2016).

Barrie et al., "17-(3-Pyridyl) Substituted Irreversible Inhibitors of Cytochrome P45017alpha" British J. Cancer, vol. 78 (Suppl. 1):34. abstract No. 33 (1998).

Barrie et al., "Biochemistry and Pharmacokinetics of Potent Non-Steroidal Cytochrome P45017Alpha Inhibitors," J Steroid Biochem. Molec. Biol., vol. 60(5-6):347.351 (1997).

Barrie et al., "CB7598: A Potent Inhibitor of Steroidal 17alpha-Hydroxylase/C17,20 Lyase. A Potential New Drug for the Treatment of Prostate Caneer," J. Pharmacy and Pharmacology, vol. 47(128):1076 (1995).

Barrie et al., "Highly Potent Inhibitors of Human Cytochrome P-450(17alpha): Activity In Vitro and In Vivo," British J. Cancer (1993), p. 75, BACR/ACP/BOA Annual Meeting, abstract No. 177 (1993).

Barrie et al., "Inhibitors of Cytochrome P450 17alpha (17alpha-Hydroxylase/C17,20 Lyase)," Endocrine-Related Cancer, vol. 3:25-39 (1996).

Barrie et al., Pharmacology of Novel Steroidal Inhibitors of Cytochrome P450 17alpha (17alpha- Hydroxylase/C17-20 Lyase; J, Steroid Biochem. Molec. Biol., vol. 50(5/6)267-273 (1994).

Barrie et al., "Biochemistry of Potent Cytochrome P45017alpha Inhibitors," British J. Cancer, vol. 75 (Suppl. 1):6, abstract No. 1.7 (1997).

Beardsley et al., "Systemic Therapy After First-Line Docetaxel in Metastatic castration-Resistant Prostate Cancer," Current Opinion in Supportive and Palliative Gare, vol. 2:161-166 (2008).

Beer et al., "Weekly high-dose calcitriol and docetaxel in metastatic androgen-independent prostate cancer," J. Clin. Oncology, vol. 21(1) pp. 123-128 (2003).

Bernard P. Schimmer and Keith L. Parker, Adrenocorticotropic Hormone: Adrenocortical Steroids and Their Synthetic Analogs: Inhibitors of the Synthesis and Actions of Adrenocortical Hormones, in Goodman & Gilman's the Pharmacological Basis of Therapeutics, (10th ed. 2001), pp. 1649-1677.

Berry, W. et al.. Phase III Study of Mitoxantrone Plus Low Dose Prednisone Versus low Dose Prednisone Alone in Patients with Asymptomatic Hormone Refractory Prostate Cancer, The Journal of Urology, 2002, pp. 2439-2443, vol. 168.

Biglieri EG et al., "Herron MA, Brust N. 17-hydroxylation deficiency in man", Journal of Clinical Investigation 1966, vol. 45 No. 12, pp. 1946-1954.

Bigueri, et al., "17-Hydroxylation Deficiency in Man", Journal of Clinical Investigation, vol. 45, No., 12. 1966, 10 pages.

Bisphosphonates Fact Sheet. The Paget Foundation http://www.paget.org/information.FactSheet/bisfact/html (Jul. 2006).

Blackard, "Letters to the Editor," Journal of Urology, Re: Prostate Specific Antigen for Assessing Response to Ketoconazole and Prednisone in Patients With Hormone Refractory Metastatic Prostate Cancer, Filed for Case IPR2016-00286, Janssen Exhibit 2049, on Dec. 1991, vol. 146, No. 6, pp. 1621-1622.

Blair, Medivation, INC. "Looking into Recent Weaknesses: Second-Quarter Preview and Breast Cancer Prospect; Lowering Price Target ta $150 on Adjusting Share Count," Jul. 14, 2015.

Blutt et al., "A calcitriol analogue, EB 1089, inhibits the growth of LNCaP tumors in nude mice," Cancer Res., vol. 60 (4), pp. 779-782 (2000).

Booth et al., Oncology's trials,' Nature Reviews, vol. 2: Aug. 2003, pp. 609-610.

Borner et al., "Answering Patients Needs", Oral Alternatives to Intravenous Therapy, The Oncologist 2001 Vol. 6, suppl 4, pp. 12-16.

Boudadi et al., "Resistance to Novel Antiandrogen Therapies in Metastatic Castration-Resistant Prostate Cancer", Clin Med Insights Oncol, Feb. 9, 2016, vol. 10, (Suppl 1), pp. 1-9.

Boumpas et al., "Glucocorticoid Therapy for Immune-mediated Diseases: Basic and Clinical Correlates," Annals of Intemal Medicine, Filed for Case IPR2016-00286, Janssen Exhibit 2021 on Dec. 15, 1993, vol. 119, No. 12 1198-1208.

Brenner et al. ETS fusion positive prostate tumor models respond to olaparib; Cancer Cell 19 664; 2011.

Brooke et al., "A novel point mutation in P450c17 (CYP17) causing combined 17alpha-hydroxylase/17,20.lyase deficiency",. The Journal of Clinical Endocrinology & Metabolism, 2006, vol. 91 No. 6 pp. 2428-2431.

Brown et al., "Targeting DNA Repair in Cancer: Beyond PARP Inhibitors", Cancer Discovery, Jan. 2017, vol. 7, No. 1, pp. 20-37.

Bruno et al., Targeting cytochrome P450 enzymes: A new approach in anti-cancer drug development Elsevier, 2007, pp. 5047-5060, vol. 15.

Bubley et al., "Eligibility and Response Guidelines for Phase II Clinical Trials in Androgen-Independent Prostate Cancer: Recommendations From the Prostate-Specific Aniigen Working Gmup", Journal of Clinical Oncology, file for Case IPR2016-00286, Janssen Exhibit 2057, on Nov. 1999, vol. 17, No. 11, pp. 3461-3467.

Bundgaard, "Design of Prodrugs", Elsevier, 1985, pp. 1-96.

Burgess and Roth et al., "Changing Perspectives of the Role of Chemotherapy in Advanced Prostate Cancer," urologic Clinics of North America 2006, filed for case IPR2016-00286, Janssen Exhibit 2007, vol. 33, pp. 227-236.

Burke et al. , "Active-Site Conformation of 17-(3-Pyridyl) Androsta-5, i6-Dien-3Beta-of, a Potent Inhibitor of the P450 Enzyme C17alpha-Hydroxylase/C17-20 Lyase," Bioorganic & Medicinal Chemistry letters, vol. 5(11):1125-1130 (1995).

C.J. Ryan et al., "Abiraterone acetate plus prednisone versus placebo plus prednisone in chemotherapy-naive men with metastatic castration-resistant prostate cancer (COU-AA-302): final overall survival analysis of a randomised, double-blind, placebo-controlled phase 3 study", The Lancet, filed for Case# IPR2016-00286, vol. 16, pp. 152-160, Feb. 2015.

Campbell-Walsh Urology, Ninth Edition, Saunders, vol. 3, Chapters 104 and 105, 2007.

Cancer.0111(ACS), "What are the key statistics about prostate cancer?", http://www.cancer.org/cancer/prostatecancerfdetaile<iguide/prostat e-cancer-key-statistics (accessed Jun. 28, 2016), Mylan Pharms. Inc., Exhibit 1041, 2 pages.

Cancer.gov (NIH NCI), "Metastatic cancer," https://www.cancer.gov/types/metastatic-cancer (accessed Oct. 3, 2016), pp. 3 for Case# IPR2016-00286.

Cancer.gov (NIH NCI), "Prostate-specific antigen (PSA) test," http//www.cancer.gov/types/prostate/psa-fact-sheet (accessed Apr. 11, 2017), 8 pages.

Cancer.gov (NIH NCI), Metastatic cancer https://www.cancer.gov/about-cancer/treatment/drugs/docetaxel (accessed Oct. 3, 2016), pp. 3 for Case# IPR2016-01332.

Cancer.Net "Treatment of Metaslallc Castration-Resistant Prostate Cancer" filed for Case# IPR2016-00286 on Sep. 8, 2014 3 pages.

Cancer.net (ASCO Patient Website), "Treatment of Metastatic Castration-Resistant Prostate Cancer Sep. 8, 2014", http://www.cancer.net/research-and-advocae:y/asco-care-andtreatment-recommendalions-patients/treatment-metastaticcastration-resistant-prostate-cancer (accessed Jun. 28, 2016), 4 pages.

Cancer.org (ACS), "Hormone therapy for prostate cancer," https://www.cancer.org/conten/cancer/en/cancer/prostatecancer/ treating/hormone-therapy•.html (accessed Apr. 10, 2017), 11 pages.

Cannell, 100th Annual Meeting of the American Association for Cancer Research, Los Angeles, CA, USA;, http://oncology.thelancel.com, 2007, pp. 471, vol. 8.

Carden et al., "Crossover Pharmacokinetics (PK) Study to Assess Oral Administration of Abiraterone Acetate Capsule and Tablet Formulations in Fasted and Fed States in Patients with Prostate Cancer," J. Clin. Oncol. (Meeting abstracts),. vol. 26 (May 20 Supplement), abstract No. 5168 (2008).

(56) References Cited

OTHER PUBLICATIONS

Carducci et al., "A Phase 3 Randomized Controlled Trial of the Efficacy and Safety of Atrasentan in Men With Metastatic Hormone . . . refractory Prostate Cancer," vol. 110, No. 9, Nov. 1, 2007, pp. 1959-1966.
Carducci, MA, What is more exciting? The Activity of Docetaxel in Early Prostate Cancer or the Successful Collaboration between Urologists and Medical Oncologists to complete a study in early Prostate Cancer'?, Journal of Clinical Oncology (2005), vol. 23, Na. 15, pp. 3304-3307.
Carlson et al., "PARP Inhibitors Show Promise Against Metastatic Triple-Negative Breast Cancer in Early Studies," Oncology Times, vol. 31, Issue 15, Aug. 10, 2009, pp. 10-11.
Carroll, "Updated: J&J grabs prostate cancer rights for Tesaro's niraparib in $500M deal", Apr. 6, 2016, p. 1.
CB-7630 Shows Activity in Prostate Cancer Trials, Daily Essentials (2007).
CB1089, Cougar Biotechnology, Inc., http:/www.cougatbiotechnology.com/eb1089.html, 2006, pp. 1-2.
Cecil Textbook of Medicine, Wyngaarden & Smith 18th edition; Chapter on "Glucocorticosteroid Therapy", Wyngaarden & Smith 18th edition, (1988) p. 128-131.
Centers for Disease Control and Prevention, Prostate Cancer Janssen Exhibit 2100, Amerigen vs. Janssen filed for Case# IPR2016-00286, 2 Pages.
Chang, Ching-Yi, et al.Glucocorticoids Manifest Androgenic Activity in a Cell Derived from a Metastatic Prostate Cancer, Cancer Research, 2001, pp. 8712-8717, vol. 61.
CHARTED-Chemohormonal Therapy versus Androgen Ablation Randomized Trial for Extensive Disease in Prostate Cancer, Declaration of Christopher J. Sweeney, Clinical Advances in Hematology and Oncology, filed for Case IPR2016-01582, Janssen Exhibit 2157, on Aug. 2006, vol. 4, No., 8, pp. 588.590.
Chemicals: Seocalcitol http//ctd.mdibl.org/voc.go:isessionid"126741EAF326D9CE517F360251236091?voc=chem&acc=C078903&queryferms=seocaldtol&qurey Type=contains&browser=r (Jul. 17, 2006).
Chen, C.D, et al., Molecular determinants of resistance to antiandrogen therapy, Nat Med, 10(1), (2004) pp. 33-39.
Cheol Kwak, et al., "Abiraterone acetate and prednisolone for metastatic castration-resistant prostate cancer failing androgen deprivation and docetaxel-based chemotherapy", International Journal of Urology (2014), vol. 21, pp. 1239-1244.
Chi et al., "A Phase I Pharmacokinetic and Pharmacodynamic Study of OGX-011, a 2'-Methoxyethyl Antisense Oligonucleotide to Clusterin, in Patients With Localized Prostate Cancer", Journal of the National Cancer Institute, vol. 97, Issue 17, Sep. 7, 2005, pp. 1287-1296.
Chi et al., "Niraparib and Abiraterone Acetate for Metastatic Castration-Resistant Prostate Cancer", J Clin Oncol., Mar. 23, 2023, vol. 41, No. 18, pp. 3339-3351.
Chi et al., "Niraparib plus abiraterone acetate with prednisone in patients with metastatic castration-resistant prostate cancer and homologous recombination repair gene alterations: second interim analysis of the randomized phase III Magnitude trial," Annals of Oncology, vol. 34, Issue 9, Sep. 2023, pp. 772-782.
Chou et al., "Desoxyepothilone B: An efficacious microtubule-targeted antitumor agent with a promising in vivo profile relative to epothilone B", Proc. Natl. Acad. Sci. USA vol. 95, No. 16. Aug. 1998 Pharmacology, pp. 9642-9647.
Christensen G.L., "Sequential Versus Combined Treatment of Human Breast Cancer Cells with Antiestrogens and the Vitamin D Analogue EB 1089 and Evaluation of Predictive Markers for Vitamin D Treatment", Breast Cancer Research and Treatment 85(1) 53-63 (2004).
Clark et al., "Defining the normal cortisol response to the short Synacthen test", Implications for the investigation of hypothalamic pituitary disorders, clinical Endocrinology 1998 vol. 49 pp. 287-292.
Clarke et al., "Olaparib combined with abiraterone in patients with metastatic castration-resistant prostate cancer: a randomised, double-blind, placebo-controlled, phase 2 trial", The Lancet Oncology vol. 19, No. 7, Jun. 4, 2018, pp. 1-12.
Clarke et al., "Olaparib combined with abiraterone in patients with metastatic prostate cancer: Safety run-in from a phase II study", : Journal of Clinical Oncology, vol. 33, No. 15_suppl, May 20, 2015, pp. 1-3.
Clement et al., "Three dimensional pharmacophore modeling of human CYP17 inhibitors. Potential agents for prostate cancer therapy", journal of Medicinal Chemistry, vol. 46, No. 12, 2003, pp. 2345-2351.
Clinical trial patient data extract, for Patient 1, Patient 2, 2007, 2 pages.
Clinical Trials: What you need to know, American cancer society, Aug. 18, 2020, pp. 1-29.
ClinicalTrials.gov Archive, NCT00485303 on Jun. 11, 2007. http://clinicaltrials.gov/archive/NCT00485303/, 3 pages.
Clinicaltrials.gov, "Phase II Clinical Trial of Abiraterone Acetate Without Exogenous Glucocorticoids in Men With Castration-resistant Prostate Cancer With Correlative Assessment of Hormone Intermediates.", NCT02025010, *Amerigen* v. *Janssen*, Case# IPR2016-00286, 2017, 5 pages.
Cole, "Cancer Expert Doubts Claims About Prostate Cancer Trial," BMJ, vol. 337: a979 (2008).
Collette et al., Is Prostate-Specific Antigen a Valid Surrogate End Point for Survival in Hormonally Treated Patients With Metastatic Prostate Cancer? Joint Research of the European Organization for Research and Treatment of Cancer, the Limburgs Universitair Centrum, and AstraZeneca Pharmaceuticals, Journal of Clinical Oncology, vol. 23, No. 25, pp. 6139-6148 (Sep. 1, 2005).
Collette et al., Prostate-specific antigen (PSA) alone is not an appropriate surrogate marker of long-term therapeutic benefit in prostate cancer trials, European Journal of Cancer, 42, pp. 1344-1350 (2006).
Collins et al., "A systematic review of the effectiveness of docetaxel and mitoxantrone for the treatment of metastatic hormone-refractory prostate cancer," British J. of Cancer. 95, pp. 457-462 (2006).
Colston et al, "Mechanisms implicated In the growth regulatory effects of vitamin D in breast cancer," Endocrine-Related Cancer, vol. 9(1):45-59 (2001).
Colston, K. W., "Effects of Seocalcitol (EB1089) on Nitrosomethyl Urea-Induced Rat Mammary Tumors", 80(3) Breast Cancer, 303-311 (2003).
Conde and Aronson, "Risk factors for male osteoporosis." Urologic Oncology, Seminars and Original Investigations, Filed for Case IPR2016-00286, Janssen Exhibit 2025. on 2003, vol. 21, pp. 380-383.
Consider the impact of ZYTIGA (Registered) 500 mg film-coated tablets over the course of a month or a year for your patients with mCRPC, ZYTIGA (Registered) (abiraterone acetate) Dosing & Monitoring HCP, May 24, 2018, 7 pages.
Continuing Challenge of Hormone-Refractory Prostate Cancer, Declaration of Oliver Sartor, "Clinical Genitourinary Cancer", filed for case Janssen IPR2016-01582, Janssen Exhibit 2156 on Mar. 2006, pp. 238-239.
Cooper et al., "Mechanisms of Disease: Biomarkers and molecular Targets from microarray Gene Expression Studies in Prostate Cancer," Nature Ctn Practice OncoL, vol. 4('12):677-687 (2007).
Costa-Sanlos, M. et al.. "Two Prevalent CYP17 Mutations and Genotype-Phenotype Correlations in 24 Brazilian Patients with 17-Hydroxylase Deficiency," J, Clin. Endocrin. & MetaboL vol. (89)1, pp. 49-60, 2004.
Cougar Biotechnology Announces Acceptance of CTA for Abiraterone Acetate, News Release, available at: http:www.cougarbiotechnolagy.com (2005).
Cougar Biotechnology Announces Agreement with FDA on Special Protocol Assessment for PhaseIll Trial of C87630 (Abiraterone Acetate) in Chemotherapy Naive Castration Resistant Prostate Cancer Patients. News. Release, available at http:/www.cougarbiotechnology.com (2008).

(56) References Cited

OTHER PUBLICATIONS

Cougar Biotechnology Announces CB7630 Phase I Data to be Presented at National Cancer Research Institute Conference, News Release (Sep. 27, 2006), available at http://www.cougarbiotechnology.com (2006).
Cougar Biotechnology Announces Initiation of Phase I Trial for CB7630 (Abiraterone Acetate), News Release, available at: http://www.cougarbiotechnology.com (2006).
Cougar Biotechnology Announces Initiation of Phase III Trial of CB7630 (Abiraterone Acetate), News Release, available at http://www.cougarbiotechnology.com (2008).
Cougar Biotechnology Announces Presentation of Positive CB7630 (Abiraterone Acetate) Phase II Data at ASCO 2009 Genitourinary Cancers Symposium, News Release, available at http://www.cougarbiotechnology.com (2009).
Cougar Biotechnology Announces Presentation of Positive CB7630 Clinical Data at AACR-NCI-EORTC International Conference on Molecular Targets and Cancer Therapeutics, News Release, available at: http://www.cougarbiotechnology.com (2007).
Cougar Biotechnology Announces Presentation of Positive CB7630 Clinical Data at ESMO Conference, News Release, available at: http://www.cougarbiotechnology.com (2007).
Cougar Biotechnology Announces Presentation of Positive CB7630 Phase I Clinical Data at ASCO 2008 Genitourinary Cancers Symposium, News Release, available at http://www.cougarbiotechnology.com (2008).
Cougar Biotechnology Announces Presentation of Positive Phase I and Phase II Data at ASCO Prostate Cancer Symposium, News Release, available at hitp://www.cougarbiotechnology.com (2007).
Cougar Biotechnology Inc. with the U.S. Securities and Exchange Commission, From 10-QSB, 2013.
Cougar Biotechnology Initiates Phase II Trial of C87630 (Abiraterone Acetate), News Release, available at: http://www.cougarbiotechnology.com (2006).
Cougar Biotechnology Presents CB7630 Phase I Clinical Data at the 2005 Prostate Cancer Symposium, News Release, available at http/www.cougarbiotechnology.com (2005).
Cougar Biotechnology Presents CB7630 Phase I Data at Prostate Cancer Foundation Scientific Retreat. News Release, available at: http://www.cougarbioiechnology.com (2004).
Cougar Biotechnology Presents Positive CB7630 (Abiraterone Acetate) Phase I and Phase II Data at ASCO 2008 Annual Meeting, News Release, available at http://www.cougarbiotechnology.com (2008).
Cougar Biotechnology Presents Positive CB7630 Clinical Data at AACR Annual Meeting Late-Breaking Clinical Trials Session, News Release, available at: http:www.cougarbiotechnology.com (2007).
Cougar Biotechnology Presents Positive CB7630 Phase II Data at Chemotherapy Foundation Symposium; News Release, available at: http://www.cougarbiotechnology.com (2007).
Cougar Biotechnology Presents Positive CB7630 Phase II Data at EORTC-NCI-AACR Symposium, News Release, available at: http://www.cougarbiotechnology.com (2008).
Cougar Biotechnology to Present Clinical Data on CB7630 (Abiraterone Acetate) at American Society of Clinical Oncology 2008 Annual Meeting. News Release, available at http://www.cougarbiotechnology.com (2008).
Cougar Biotechnology, A Phase iIii Open Label Study of the 17-Hydroxylase/C17-20 lyase Inhibitor, Abiraterone Acetate in Patients with Prostate Cancer Who have Failed Hormone Therapy, Latter to Johann De-Bono, Re: Revised abiraterone protocol, Dec. 6, 2004, 86 pages.
Cougar Biotechnology, Cougar Biotechnology Announces Initiation of Phase I/II Trial for CB7630 (Abiraterone Acetate), Cougar Biotechnology, Dec. 14, 2004.
Cougar Biotechnology, Cougar Biotechnology Announces Presentation of Positive CB7630 Clinical Data at ESMO Conference, Drugs.com, Jul. 2007.
Cougar Biotechnology, Cougar Biotechnology presents C87630 Phase I clinical data at the 2005 Prostate Cancer Symposium, All Business, 2005.
Cougar Biotechnology, Cougar Technology Announces Presentation of Positive CB7630 Clinical Data at ASCO Annual Meeting, The Free library, Jun. 4, 2007.
Cougar Biotechnology, Inc., Clinical Study Report: COU-AA-001 and COU-AA 001 EXT, Nov. 17, 2010, 7 pages.
Cowen & Company, "Biotechnology Quarterly."Jul. 2, 2012.
Cowen & Company, "Quick Take: Zytiga Gets FDA OK for Use in Pre-Chemo Setting on rPFS Data-Johnson & Johnson."Accessed (Dec. 11, 2012).
Crawford et al., "Treating Patients with Metastatic Castration Resistant Prostate Cancer", a Comprehensive Review of Available Therapies, The Journal of Urology, vol. 194, Dec. 2015, pp. 1537-1547.
Credit Suisse, "Prostate Cancer-Implications of Zytiga's Pre-Ghemo Approvat" Dec. 11, 2012.
Czock, et al., "Pharmacokinetics and Pharmacodynamics of Systemically Administered Glucocorticoids", Pharmacokinetic (2005), 44(1), p. 61-98.
D. Lorente et al., Tumor responses following a steroid switch from prednisone to dexamethasone in castration-resistant prostate cancer patients progressing on abiraterone, British Journal of Cancer, (2014) 111, pp. 2248-2253.
Dalhoff, KA, "Phase II Study of the Vitamin D Analogue Seocalcitol in Patients with Inoperable Hepatocellular Carcinoma". 89(2) British Journal of Cancer, 252-257 (2003).
Dalia Buffery, "The 2015 Oncology Drug Pipeline: Innovation Drives the Race to Cure Cancer", Am Health Drug Benefits, vol. 8(4), 2015, pp. 216-222.
Daniel C Danila et al., "Prednisone Therapy in Patients With Docetaxel-Treated Castration-Resistant Prostate Cancer", Journal of Clinical Oncology, vol. 28, No. 9, Mar. 20, 2010. pp. 1496-1501.
Danielenko et al., "Enhancement by other compounds of the anticancer activity of vitamin D3 and its analogs;" Experimental Cell Research, vol. 298 (2):339-358 (2004).
Danila et al., "Abiraterone acetate and prednisone in patients (Pts) with progressive metastatic castration resistant prostate cancer (CRPC) after failure of docetaxel-based chemotherapy," J. Clin. Oncol. (Meeting abstracts), vol. 26 (May 20 Supplement), abstract No. 5019 (2008).
Danila et al., "Preliminary Phase II Results of Abiraterone Acetate in Patients With Castration Resistant Metastatic Prostate Cancer After Failure of Docetaxel-Based Chemotherapy: COU-AA-004," in Innovative Cancer Therapy for Tomorrow: Foundation Symposium XXV; presentation (2007).
Danila et al., "Preliminary Phase II Results of Abiraterone Acetate in Patients with Castration-Resistant Metastatic Prostate Cancer After Failure of Docetaxel-Based Chemotherapy," ASCO 2008 Genitourinary Cancers Symposium, abstract No. 3 (2008).
Danila et al., Phase II Multicenter Study of Abiraterone Acetate Plus Prednisone Therapy in Patients With docetaxel-Treated Castration-Resistant Prostate Cancer. Journal of Clinical Oncology, Filed for Case IPR2016-01332, Janssen Exhibit 2016, on Mar. 20, 2010, vol. 28, No. 9, pp. 1496-1501.
Datta et al., The Journal of Urology, 1997, 158, 175-177.
De Bono et al. Antitumor Activity of Abiraterone Acetate, a CYP17 Inhibitor That Blocks Androgen Synthesis, in Castration-Resistant Prostate Cancer: ASCO 2008 Annual Meeting, Presentation.
De Bono et al., "Anti-tumor activity of abiraterone acetate (AA), a CYP17 inhibitor of androgen synthesis, in chemotherapy naive and docetaxel pre-treated castration resistant prostate cancer (CRPC)," J. Clin. OncoL (Meeting abstracts),. vol. 26 (May 20 Supplement), abstract No. 5005 (2008).
De Bono et al., Inhibition of CYP450c17 by abiraterone administered once daily to castrate patients with prostate cancer resistant ta LHRH analogues,. anti-androgens and steroid therapy 1s well tolerated, The institute of Cancer Research, 2007.
de Bono et al . . . Abiraterone and Increased Survival in Metastatic Prostate Cancer New England Journal of Medicine, filed for case IPR2016-01582, Janssen Exhibit 2159, on May 26, 20.11, Established in 1812, vol. 364, No. 21, pp. 1995-2005.

(56) References Cited

OTHER PUBLICATIONS

De Coster et al . . . "P450-Dependent Enzymes as Targets for Prostate Cancer Therapy," J. Steroid Biochem. Malec.. Biol., vol. 56(1-6):133-143 (1996).
De Coster, et al., Effects of High-Dose Ketoconazole and Dexamethasone on ACTH-Stimulated Adrenal Steroidogenesis in Orchiectomized Prostatic Cancer Patients, ACTA Endocrinological (Copenh), ,1987, pp. 265-271, vol. 115.
Debono et al., "Clinical and endocrine evaluation of abiraterone acetate (AA), a rationally designed small molecule inhibitor of androgen synthesis targeting 17Alpha-hydroxylase (170H)/17,20 lyase in patients with hormone refractory prostate cancer," 2005 Prostate Cancer Symposium, Abstract No. 290.
Decision of the United States Court of Appeals for the Federal Circuit; U.S. Appl. No. 15/950,757; Appeal 2023-1763; Jul. 11, 2024, pp. 2.
Decision of the US Patent Trial and Appeal Board; U.S. Appl. No. 15/950,757; Appeal 2022-004874; Feb. 2, 2023, pp. 17.
Declaration of Dr. Gerhardt Attard, 2015, 29 pages.
DELTASONE—prednisone tablet Pharmacia and Upjohn and Company, Deltas one (Registered) prednisone tablets, USP. 2007, 13 pages.
Demario et al., "Oral Chemotherapy", Rationale and Future Directions, Journal of Clinical Oncology, vol. 16. No. 7, Jul. 1998, pp. 2557-2567.
Dennis L Kasper, et al (Eds.), Harrison's Principles of Iniernal Medicine, 16th Edition (2005), 12 pages.
Di Cerbo et al., "Combined 17 alpha-Hydroxylase/17, 20-lyase deficiency caused by Phe93 Cys mutation in the CYP17 gene", The Journal of Clinical Endocrinology & Metabolism 2002, vol. 87, No. 2 pp. 898-905.
Dickstein G et al., "One microgram is the lowest ACTH dose to cause a maximal cortisol response. There is No. diurnal variation of cortisol response to submaximal ACTH stimulation". European Journal of Endocrinology 1997, vol. 137 No. 2 pp. 172-175.
Dickstein G., et al.. , "Low' dose ACTH test—A word of caution to the word of caution" when and how to use it Journal of Clinical Endocrinology and Metabolism 1997, vol. 82 No. 1, 322 pages.
Division of Endocrinology et al., "Dose-response aspects in the clinical assessment of the hypothalamusry-adrenal axis and the low-dose adrenocorticotropin test", European Journal of Endocrinology, 1996, 135: pp. 27-33.
Dizdar 2015, Is Dexarnethasone a Better Partner for Abiraterone Than Prednisolone, The Oncologist May 2015 vol. 20, No. 5 e 13.
Donold L. Trump et al., High-Dose Ketoconazole in Advanced Hormone-Refractory Prostate Cancer: Endocrinologic and Clinical Effects, Journal of Clinical Oncology, vol. 7, No. Aug. 8, 1989, pp. 1093-1098.
Dorff, TB, Crawford, ED. Management and challenges of corticosteroid therapy in men with metastatic castrate-resistant prostate cancer, Annals of Oncology, 2013. pp. 31-38, vol. 24(1).
Dorin et al., "Diagnosis of Adrenal Insufficiency", Academia and Clinic, Annals of Internal Medicine, Filed for Case IPR2016-00286, Janssen Exhibit 2051, on Aug. 5, 2003, vol. 139, No. 3, pp. 194-204.
Drean et al., "PARP inhibitor combination therapy", Critical Reviews in Oncology/Hematology, vol. 108, 2016, pp. 73-85.
Due et al., "In vitro and in vivo models for the evaluation of potent inhibitors of male rat 17 (Alpha)-hydroxylase/C17,20-lyase," Journal of Steroid Biochemistry & Molecular Biology, 2003, Filed for Case IPR2016-01332, Janssen Exhibit 2012, vol. 84 pp. 537-542.
ECOG Performance Status, "Developed by the Eastern Cooperative Oncology Group, Robert L Combs, MD, Group Chair",. *Wockhardt* v. *Janssen*, Field for Case# IPR2016-01582, Janssen Exhibit 2158, http://ecog-acrin.org/resources/ecog-performance-status, Mar. 14, 2017, 2 pages.
Efstathiou et al., "Candidate Predictors of Response to Abiraterone Acetate (AA) in Castrate Resistant Prostate Cancer (CRPC)," 2009 Genitourinary Cancers Symposium (Feb. 26-28, 2009), abstract Submission (2008).
Efstathiou et al., Identification of an Androgen Withdrawal Responsive Phenotype in Castrate Resistant Prostate Cancer (CRPC) Patients Treated with Abiraterone Acetate; presentation, 2007.
Efstathiou, Eleni, et al. Effects of Abiraterone Acetate on Androgen Signaling in Castrate-Resistant Prostate Cancer in Bone, American Society of Clinical Oncology, Journal of Clinical Oncology, 2011, pp. 1-8.
Efstathiou, et al., "Enzalutamide in Combination with Abiraterone Acetate in Bone Metastatic Castration-resistant Prostate Cancer Patients", Science Direct, European Urology Oncology 3 (2020), 2019 European Association of Urology, Published by Elsevier B.V., pp. 119-127.
Eighteenth Edition Physicians' Desk Reference to Pharmaceutical Specialties and Biologicals, 1964, PDR Published by Medical Economics, INC. 3 pages.
EMA-Zytiga Product Information, http://www.ema.europa.eu/docs/en_GB/document_library/EPAR _-product_Information/human/002321/WC500112858pdf, 2016, 37 pages.
Emel Arinc et al., "Molecular Aspects of Monooxygenases and Bioactivation of Toxic Compounds", Series A: Life Sciences vol. 202 Mylan Pharms. Inc., 1989, 28 pages.
Endert E. et al., "Establishment of reference values for endocrine tests. Part IV: Adrenal insufficiency", Netherlands, Journal of Medicine 2005, vol. 63, No. 11, pp. 435-443.
Ergun-Longmire. Berrin et al., "Two Novel Mutations Found in a Patient with 17a-Hydroxylase Enzyme Deficiency", The Journal of Clinical Endocrinology & Metabolism (2006), 91(10), p. 4179-4182.
Eric J. Small et al., "Ketoconazole Retains Activity in Advanced Prostate Cancer Patients With Progression Despite Flutamide Withdrawal", The Journal of Urology, vol. 157 Apr. 1997, pp. 1204-1207.
Erica L. T. Van Den Akker et al., "Differential Inhibition of 17alpha-hydroxylase and 17,20-lyase activities by three novel missense CYP17 mutations identified in patients with P450c17 deficiency", The Journal of Clinical Endocrinology & Metabolism Dec. 2002, vol. 87 No. 12 pp. 5714-5721.
Erie J. Small et al., "Antiandrogen Withdrawal Alone or in Combination With Ketoconazole in Androgen-Independent Prostate Cancer Patients: A Phase III Trial (CALGB9583)", Journal of Clinical Oncology, *Wockhardt* vs. *Janssen*, Filed for Case IPR2016-01582, Janssen Exhibit 2172, on Apr. 3, 2017, 18 pages.
Excerpts from Seifter, Concepts in Medical Physiology, Chapter 34, pp. 540-553, Chapter 37, pp. 606-620 (2005), Filed for Case IPR2016-00286, Janssen Exhibit 2058.
F. Labrie et al., "Anti-hormone Treatment for Prostate Cancer Relapsing after Treatment with Flutamide and Castration", British Journal of Urology, (1989) 63 , pp. 634-638.
Fable Zustovich and Davide Pastorelli, Therapeutic management of bone metastasis in prostate cancer: an update, Expert Review of Anticancer Therapy, http://dx.doi.org/10.1080/14737140.2016.1241148, Sep. 27, 2016.
Fallowfield et al., "Patients' preference for administration of endocrine treatments by injection or tablets", results from a study of women with breast cancer, Annals of Oncology vol. 17 No. 2 Feb. 2000, pp. 205-210.
Farwell, et al., "Total Suppression of Cortisol Excretion by Ketoconazole in the Therapy of the Ectopic Adrenocorticotropic Hormone Syndrome", American Journal of Medicine, filed for case IPR2016-00286, Janssen Exhibit 2065, on Jun. 1988, vol. 84, pp. 1063-1006.
FDA News Release, "FDA expands Zytiga's use for late-stage prostate cancer," Dec. 10, 2012, http://www. fda.gov/NewsEvents/Newsroom/PressAnnouncements/ucrn331492.htm.
Feldman, "Ketoconazole and Other Imidazole derivatives as Inhibitors of steroidogenesis", filed for Case# IPR2016-00286, 1986, vol. 7, No. 4, 12 pages.
Final Written Decision, United States Patent and Trademark Office Before the Patent Trail and Appeal Board, Case No. IPR2016-01582 U.S. Pat. No. 8,822,438 82, Jan. 17, 2018, 51 pages.
Final Written Decision, United States Patent and Trademark Office Before the Patent Trial and Appeal Board, Case No. IPR2016,00286 Patent 8,822A38 B2, Jan. 17, 2018, 48 pages.

(56) References Cited

OTHER PUBLICATIONS

Final Written Decision, United States Patent and Trademark Office Before the Patent Trial and Appeal Board, Case No. IPR2016-01332 U.S. Pat. No. 8,822,438 B2, Jan. 17, 2018, 50 page.
Fizazi et al., "Abiraterone plus Prednisone in Metastatic, Castration-Sensitive Prostate Cancer", The new england journal of medicine, ,Jul. 2017, vol. 377, No. 4, pp. 352-360.
Fizazi et al., "Low Incidence of Corticosteroid-associated Adverse Events on long-term Exposure to Low-dose Prednisone Given with Abiraterone Acetate to Patients with Metastatic Castration-resistant Prostate Cancer", Eur Urol. Sep. 2016, vol. 70, No. 3, pp. 438-444.
Fossa et al., "Flutamide versus prednisone in patients with prostate cancer symptomatically progressing after androgen-ablative therapy: a phase III study of the European organization for research and treatment of cancer genitourinary group," Journal of Clinical Oncology, vol. 19( 1 ) 62-71 (2001).
Fossa, et al., Weekly Docetaxel and Prednisone Versus Prednisolone Alone in Androgen-Independent Prostate Cancer: A Randomized Phase II Study, European Urology, 2007, pp. 1691-1699, vol. 52.
Fourteenth Edition Physicians' Desk Reference to Pharmaceutical Specialties and Biologicals, 1960, PDR, 2 pages.
Friel, Patrick N., et al., Suppression of adrenal function by low-dose prednisone: assessment with 24-hour urinary steroid hormone profiles—A review of five cases , Alternative Medicine Review (2006), 11(1).
Full Prescribing Information and Patient Information for ZEJULA, Mar. 2017, pp. 1-19.
G. Sonpavde et al., Impact of single-agent daily prednisone on outcomes in men with metastatic castration-resistant prostate cancer, Prostate Cancer and Prostatic Diseases (2016) 00, pp. 1-5.
Garnick Deposition Blackhard, Letter to Editor, The Journal of Urology. "Official Journal of The American Urological Association, Inc.", file for Case IPR2016-01332, Janssen Exhibit 2011 on Dec. 1991, vol. 146, No. 6, pp. 1621-1622.
Garnick et al., "Androgen deprivation therapy: the future", Prostate Cancer Principles and Practice, 2006, 19 pages.
Geethakumari et al., "PARP Inhibitors in Prostate Cancer", Curr Treat Options Oncol., 2017, vol. 18, 37, pp. 1-16.
Genentech Provides Update on Phase III Study of Avastin in Men With late Stage Prostate Cancer Janssen Exhibit 2081, Amerigen vs. Janssen filed for Case# IPR2016-00286, Mar. 12, 2010, 3 Pages.
Geoff Cumming, "Inference by eye: reading the overlap of independent confidence intervals", Statistics in Medicine, vol. 28, 2009, pp. 205-220.
Gerber, et al., Prostate Specific Antigen for Assessing Response to Ketoconazole and Prednisone in Patients with Hormone Refractory Metastatic Prostate Cancer, The Journal of Urology, 1990, pp. 1177-1179, vol. 1444, No. 5.
Ghatana et al . . . "Effect of Single-agent Daily Prednisone on Outcomes and Toxicities in Metastatic Castration- resistant Prostate Cancer: Pooled Analysis of Prospective Studies", Clinical Genitourinary Cancer, vol. 16, No. 2, Aplil 2018, pp. e277-e287.
Gignac et al., "Castration Resistant, Taxane Naive Metastatic Prostate Cancer: Current Clinical Approaches and Future Directions," J. Urology, vol. 178:S30-S35 (2007).
Gill et al., "Efficacy of Eplerenone in the Management of Mineralocorticoid Excess in Men With Metastatic Castration-resistant Prostate Cancer Treated With Abiraterone Without Prednisone", Clinical Genitourinary Cancer; vol. 15, No. 4, Aug. 2017, pp. e599-e602.
Gills, "ASCO GU Highlights New Treatment Options for Prostate Cancer", 2016 Highlights from ASH: CLL News, 2015, 5 Pages.
Gleave et al., "Use of antisense oligonucleotides targeting the cytoprotective gene, clusterin, to enhance androgen• and chemo-sensitivity in prostate cancer", World J Urol. Feb. 2005, vol. 23, No. 1, pp. 38-46.
Gordon Williams et al., "Objective Responses to Ketoconazole Therapy in Patients with Relapsed Progressive Prostatic Cancer" British Journal of Urology vol. 58, pp. 45-51 (1986).
Gras Jordi: "Niraparib hydrochloride. Poly [ADP-ribose] polymerase (PARP) inhibitor, Oncolytic" , Drugs of the Future, vol. 38, No. 10, Oct. 1, 2013 (Oct. 1, 2013), pp. 679-685, XP009195509, Prous Science, ES ISSN: 0377-8282.
Grinspoon and Biller, "Clinical Review 62 Laboratory Assessment of Adrenal Insufficiency", Journal of Clinical Endocrinology and Metabolism, Filed for Case IPR2016-00286, Janssen Exhibit 2052, on 1994, vol. 79. No. 4, pp. 923-931.
Grove, M. et al., "Bioavailability of Seocalcitol i: Relating Solubility in Biorelevant Media with Oral Bioavailability in Rats-Effect of Medium and Long Chain Triglycerides", 94(8) J. Pharm. Sci. No. 1830-1838 (2005).
H.I. Scher et al., Design and End Points of Clinical Trials for Patients with Progressive Prostate Cancer and Castrate Levels of Testosterone: Recommendations of the Prostate cancer Clinical Trials Working Group, Journal of Clinical Oncology, vol. 26, No. 7, at 1148-1159 (Mar. 1, 2008).
Hadaschik et al., "Novel targets and approaches in advanced prostate cancer", Current Opinion in Urology 2007, vol. 17: pp. 182-187.
Haidar et al., "Effects of novel 17alpha-hydroxylase/C17, 20-lyase (P450 17, CYP 17) inhibitors on androgen biosynthesis in vitro and in vivo", Journal of Steroid Biochemistry & Molecular Biology, Apr. 2003, vol. 84, No. 5, pp. 555-562.
Haidar et al., "Novel steroidal pyrimidyl inhibitors of P450 17 (17alpha-hydroxylase/C17-20-lyase)," Arch. Phann. Pharm. Med. Chern., vol. 334:373-374 (2001).
Hakki et al., CYP17- and CYP11B-dependent steroid hydroxylases as drug development targets, Elsevier. 2006, pp. 27-52, vol. 11.
Hansen. C. M. et al., "Seocalcitol (EB 1089): A Vitamin D. Analogue of Anti-Cancer Potential. Background, Design, Synthesis,. Pre-Clinical and Clinical Evaluation", 6 Current Pharmaceutical Design, 803-828 (2000).
Harris, et al., Low Dose Ketoconazole with Replacement Doses of Hydrocortisone in Patients with Progressive Androgen Independent Prostate Cancer, The Journal of Urology, 2002, pp. 542-545, vol. 168.
Harrison's 15th Edition Principles of Internal Medicine, Braunwald Fauci Kasper Hauser Longo Jameson, N Engl J. Med. 341: 156, 1999.
Hartmann et al., "Synthesis and evaluation of novel steroidal oxime inhibitors of P450 17 ( 17alpha-hydroxylase/C17-20-lyase) and 5alpha-reductase types 1 and 2," J. Med. Chem., vol. 43:4266-4277 (2000).
Harzstark et al., "Novel Therapeutic Strategies in Development for Prostate Cancer," Expert Opin. investig. Drugs, vol. 17(1):13-22 (2008).
Harzstark et al., "Therapies in Development for Castrate-Resistant Prostate Cancer," Expert Rev. Anticancer Ther.; vol. 8(2):259-268 (2008).
Haynes et al., "Pharmacology of CB759S, a Highly Potent Inhibitor of Cytochrome P450c17." Proceedings American Association for Cancer Research, vol. 35, Eighty-fifth Annual Meeting, abstract No. 2507 (1994).
Hellersledt et al., "The current state of hormonal therapy for prostate cancer", CA A C, ancer Journal for Clinicians, May-Jun. 2002, vol. 52, No. 3, pp. 154-179.
Heremans GF, Moolenaar AJ. van Gelderen HH. Female phenotype In a male child due to 17-alpha-hydroxylase deficiency. Arch Dis Child, file for Case IPR2016-00286, Amerigen Exhibit 1167 on 1976, vol. 51. No. 9 pp. 721-723.
Herr and Pfitzenmaier. "Glucocorticoid use in prostate cancer and other solid tumors: implications for effectiveness of cytotoxic treatment and metastases," The Lancet Oncol, Filed for Case IPR2016-00286, Janssen EXHIBIT 2023, 01: May 2006, vol. 7 pp. 425-430.
Highlights of Prescribing Information, "Akeega FDA label," Aug. 2023, pp. 32.
Highlights of Prescribing Information, Zytiga, Reference ID: 2939553, Apr. 2011, pp. 1-22.
Highlights of Zytiga Prescribing Information, 2015.
Highlights of Zytiga Prescribing Information, 2018.
Hildesheim, "Prostate cancer pill extends life", Lancastria.net. May 26, 2011, 5 pages.

(56) References Cited

OTHER PUBLICATIONS

History of Changes for Study: NCT01576172, "Abiraterone Acetate and Prednisone With or Without Veliparib in Treating Patients With Metastatic Hormone-Resistant Prostate Cancer", NCT01576172 Version 52, Dec. 22, 2016, 23 pages.
Hopkins et al., "Mechanistic Dissection of PARP1 Trapping and the Impact on In Vivo Tolerability and Efficacy of PARP Inhibitors", Mol Cancer Res, vol. 13, Issue 11, 2015, pp. 1465-1477.
Horsham, Pa, Dec. 10, 2012—US. FDA Approves Expanded ZYTIGA (Registered) Indication for Treatment of Metastatic Castration-Resistant Prostate Cancer Johnson & Johnson, Services, INC. 1997-2017. 5 pages.
Hotte and Saad, "Current management of castrate-resistant prostate cancer," Current Oncology- vol. 17, Supplement 2,. S72-S79 2010 filed for Case# IPR2016-00286.
HOW Zytiga(Registered) (abiraterone acetate) ZYTIGA (Registered) Inhibits Androgen Production at 3 Sources—Inclucting the Tumor Itself Works, htips://www.zytiga.com/print/about-zytiga/how-zytiga-works (accessed Jul. 23, 2015).
Hsieh et al., "Novel Concepts in Androgen Receptor Blockade," The Cancer Journal (January/Feb. 2008), vol. 14(1):11-14.
Huggins, Charles, et al. Studies on Prostatic Cancer.I. The Effect of Castration. of Estrogen and of Androgen Injection on Serum Phosphatases in Metastatic Carcinoma of the Prostate, Cancer Research, .1941, pp. 293-297, vol. 1.
Huggins, C., et al.. "Studies on Prostatic Cancer. I. The Effect of Castration, of Estrogen and Androgen Injection on Serum Phosphatases in Metastatic Carcinoma of the Prostate". Cancer Res. 22(4), (1972) pp. 232-240.
Hussain et al., "Co-targeting androgen receptor (AR) and DNA repair: A randomized ETS gene fusion-stratified trial of abiraterone + prednisone (Abi) +/− the PARP1 inhibitor veliparib for metastatic castration-resistant prostate cancer (mCRPC) patients (pts) (NCI9012)—A University of Chicago phase II consortium trial", Journal of Clinical Oncology, vol. 34, No. 15, May 20, 2016.
Hussain, Maha, et al., "Targeting Androgen Receptor and DNA Repair in Metastatic Castration-Resistant Prostate Cancer: Results from NCI9012" Journal of Clinical Oncology, American Society of Clinical Oncology, Apr. 1, 2018, vol. 36, No. 10, pp. 991-1009.
In the United States District Court, for the District of New Jersey, BTG International Limited, Janssen Biotech, Inc., Janssen Oncology, Inc., Janssen Research & Development, LLC, for Case# 15-cv 05909-KM-JBC, "Plaintiffs' Opening Claim Construction Brief" Document# 209 Filed 06130/16 p. 1 of 15.
In the United States District Court, for the District of New Jersey, *BTG International Umited, Janssen Biotech, Inc., Janssen Oncology, Inc., Janssen Research & Development, LLC*, (Plaintiffs) vs. *Actavis Laboratories FL INC*, Case# 15-cv-05909-KM-JBC, "Plaintiffs' Responsive Claim Construction Brief" Document 220 Filed Aug. 31, 2016 p. 1 of 25.
Information concerning Zytiga (abiraterone acetate) from http://www.kampendium.ch/prod/pnr/1183238lde?Platfonn=Desktop as of Mar. 25, 2014.
INSPRA (eplerenone) tablets, Initial U.S. Approval: 2002, *Wockhardt* v. *Janssen* filed for Case# IPR2016-01332, Janssen Exhibit 2129, 8 Pages.
International Search Report dated Jul. 13, 2018; International Application No. PCT/US2018/026661.
International Search Report dated Sep. 29, 2017; International Application No. PCT/US2017/044413.
Isaacs et al., Identification of ABR-215050 as lead second generation quinoline-3-carboxamide anti-angiogenic agent for the treatment of prostate cancer, The Prostate. Dec. 2006, vol. 66, No. 16, pp. 1768-1778.
J J. Body, "Low-dose prednisone and increased risk of development of bone metastases", Annals of Oncology, file for Case IPR2016-00286, Janssen Exhibit 2061, on 1996, vol. 7, pp. 643-645.
J. Gonzaalbez et al., "Establishment of reference values for standard dose short synacthen test (250 microgram). low dose short synacthen test (1 microgram) and insulin tolerance test for assessment of the hypothalamicuitary-adrenal axis in normal subjects", Clinical Endocrinology 2000, vol. 53, 199-204.
J. Trachtenberg and A. Pont, The Lancet, Ketoconazole Therapy for Advanced Prostate Cancer, Aug. 25; 1984, pp. 433-435.
Jakobsen et al., "Medroxyprogesterone Acetate and Prednisone in Advanced Breast Cancer. A Randomized Trial," Eur. J Cancer Clio. Oncol.. vol. 22:9. pp. '1067-1072 (1986).
James et al., "Antimicrobial Therapy, in Trauma Critical Care", vol. 2, (William C. Wilson et al.. eds., 2007), pp. 927-960.
Janssen Announces Preliminary Results from Phase 2 GALAHAD Study in Adults with Metastatic Castration- Resistant Prostate Cancer and DNA-Repair Pathway Defects (DRD), Feb. 14, 2019, 8 pages.
Janssen Announces U.S. FDA Breakthrough Therapy Designation Granted for Niraparib for the Treatment of Metastatic Castration-Resistant Prostate Cancer, Oct. 3, 2019, 4 pages.
Janssen Exhibit 2006, *Amerigen* v. *Janssen* IPR2016-00286, Clinical Cancer Research, A Journal of the American Association for Cancer Research, Letter to lan Judson. RE: "Manuscript# 030579, Hormonal impact of the 17a-hydroxylase/C17, 20-lyase inhibitor abiraterone acetate (CB7630) in patients with prostate cancer", Dated May 12, 2003, 4 pages.
Janssen Research & Development, LLC , "A Phase 3 Randomized, Placebo-controlled, Double-blind Study of Niraparib in Combination with Abiraterone Acetate and Prednisone Versus Abiraterone Acetate and Prednisone for Treatment of Subjects with Metastatic Prostate Cancer", Oct. 16, 2024, pp. 1-5.
Janssen Research & Development. Clinical Study Report Synopsis Protocol JNJ-212082-JPN-201; Phase 2, 2015, 9 pages.
Janssen Research and Development, LLC: "A Safety and Pharmacokinetics Stud Y of Niraparip Plus and Androgen Receptor-Targeted Therapy in Men With Met Astatic Castration-Resistant Prostate Cancer (BEDIVERE)," Clinical Trials.gov. Oct. 5, 2016.
Jarman et al., "Enzyme Inhibitors In Endocrinology," J. Endocrinology, vol. 148 (Suppl.), abstract No. S23 (1996).
Jarman et al., "The 16.17-Double Bond is Needed for Irreversible Inhibition of Human Cytochrome P45017alpha by Abiraterone (17-(3•Pyridyl)androsta-5, 16-dlen-3Beta-ol) and Related Steroidal Inhibitors," J. Med. Chem.. vol. 41:5375-5381 (1998).
Jarman et al., "The Mechanism of Irreversible Inhibition of Human Cytochrome P45017alpha by Abiraterone, a Potential New Drug for the Treatment of Prostate Cancer:" Annals of Oncol.). vol. 9(SuppL 2):135, 10th NCL-EORTC Symposium on New Drugs in Cancer Therapy, abstract No. 516 (1998).
Jemal, A., et al., "Cancer Statistics, 2007", CA Cancer J Clin, 57, (2007) pp. 43-66.
Jennifer Craft, "Eplerenone (Inspra), a new aldosterone antagonist for the treatment of systemic hypertension and heart failure", Baylor University Medical Center Proceedings, file for Case IPR2016-00286, Janssen Exhibit 2062, on Apr. 2004, vol. 17, No. 2, pp. 217-220.
JEVTANA (Registered) (cabazitaxel) injection, for intravenous use Initial U.S. Approval: 2010, Jevtana Label, Sep. 2016, *Amerigen* vs. *Janssen* filed for case IPR2016-00286, Amerigen Exhibit 1149, 25 pages.
Jevtana prescribing information (Sep. 2016), JEVTANA(Registered) (cabazitaxel) injection, for intravenous use Initial U.S. Approval 2010, 25 pages.
Jevtana Website. "Dosing and Administration", http://www.jevtana,com/hcp/dosing/defaultaspx (accessed Jun. 28, 2016), Mylan Pharms, Inc., Exhibit 1049, 4 pages.
Jhun et al., "Gene expression signature of Gleason score is associated with prostate cancer outcomes in a radical prostatectomy cohort", Oncotarget, Jun. 2017, vol. 8, No. 26, pp. 43035-43047.
John S, et al., "Secondary Hormonal Therapy for Advanced Prostate Cancer", The Journal of Urology, vol. 175, Jan. 2006, p. 27.34.
Johnson & Johnson Announces Definitive Agreement to Acquire Cougar Biotechnology, Inc,, Access to Late-Stage, First-in-Class Prostate Cancer Treatment Strengthens Presence in Oncology May 21, 2009, pp. 4.
Johnson & Johnson Q3 2016 Results—Earnings Call Transcript Oct. 18, 2016, pp. 1-32.

(56) References Cited

OTHER PUBLICATIONS

Johnson & Johnson, "Zytiga Approved in the EU for Use in the Treatment of Metastatic Castration-Resistant Prostate Cancer Before Chemotherapy," Jan. 11, 2013, 4 pages.
Jones et al., "Discovery of 2-{4-[(3S)-Piperidin-3-yl]phenyl}-2H-indazole-7-carboxamide (MK-4827): A Novel Oral Poly(ADP-ribose)polymerase (PARP) Inhibitor Efficacious in BRCA-1 and -2 Mutant Tumors", J. Med. Chem. 2009, vol. 52, pp. 7170-7185.
Jubelirer and Hogan, "High Dose Ketoconazole for the Treatment of Hormone Refractory Metastatic Prostate Carcinoma; 16 Cases and Review of the literature," The Journal of Urology, Filed for Case IPR2016-00286, Janssen Exhibit 2018, on Jul. 1989, vol. 142, No. 1. pp. 89-91.
Julian Seifter et al., "Concepts in Medical Physiology", Lippincott Wiluams and Wilkins, *Wockhardt* vs. *Janssen*, Files for Case IPR2016-01582, Janssen Exhibit 2171, 2005, 540-620 pages.
Juliet Richards et al., Interactions of Abiraterone, Eplerenone, and Prednisolone with Wild-type and Mutant Androgen Receptor: A Rationale for Increasing Abiraterone Exposure or Combining with MDV3100, Cancer Res; 72(9) pp. 2176-2182, May 1, 2012.
K, Akakura et al., Possible Mechanism of Dexamethasone Therapy for Prostate Cancer: Suppression of Circulating Level of Interleukin-6, The Prostate, 56:106.109 (2003).
K. Kobayashi et al., "Mineralocorticoid Insufficiency Due to Suramin Therapy, CANCER", vol. 78, No. 11 (Dec. 1, 1996).
K. Nishimlira et al., Low Doses of Oral Dexamethasone for Hormone-Refractory Prostate Carcinoma, Cancer vol. 89, No. 12, at 2570-2576 (Dec. 15, 2000).
Karim Fizazi et al: 11Abiraterone plus, Prednisone in Metastatic, Castration-Sensitive Prostate Cancer 11, New England Journal of Medicine, The—NEJM, vol. 377, No. 4, Jul. 27, 2017, pp. 352-360, XP055485182.
Kasper D.L. et al. (Eds.). "Harrison's Principles of Internal Medicine", 16th Edition (2005), 549 pp. 42.
Kaye et al., "New Drug Treatment for Cancer in 2007 Real Progress at Last?" EJC Supplements, vol. 5(4):35, 14th European Cancer Conference, abstract No. 126 (2007).
Kirby M. et al., "Characterising the castration-resistant prostate cancer population: A systematic review", Int'l J. Clinical Practice, vol. 65 No. (11): pp. 1180-1192, (Nov. 2011).
Kissmeyer, A.M. et al., "The Tissue-specific Distribution of 3H-Seocalcitol (EB 1089) and 3H-calcitriol in Rats", J. of Steroid Bioch. & Mol. Biol. 89-90: 43-47 (2004).
Kluetz P. G. et al., Abiraterone Acetate in Combination with Prednisone for the Treatment of Patients with Metastatic Castration-Resistant Prostate Cancer: U.S. Food and Drug Administration Drug Approval Summary. Clinical Cancer Research, Dec. 15, 2013, vol. 19, No. 24, pp. 6650-6656.
Knezevic et al., "Proteome-wide Profiling of Clinical PARP Inhibitors Reveals Compound-Specific Secondary Targets", Cell Chemical Biology, vol. 23, 2016, pp. 1490-1503.
Knol et al., "The Mis-use of Overlap of Confidence Intervals to Assess Effect Modification", Filed for Case *Wockhardt* V. *Janssen* IPR2016-01332, Janssen Exhibit 2183, on 2011, Eul J. Epidemiol., vol. 26, 253-254 pages.
Koshizuka et al., "Combined effect of vitamin D3 analogs and paclitaxel on the growth of MCF-7 breast cancer cells in vivo," Breast Cancer Research and Treatment, Springer, New York, NY, vol. 53(2): 113-120 (1999).
Krishnan et al., "A Glucocorticoid-Responsive Mutant Androgen Receptor Exhibits Unique Ligand Specificity Therapeutic Implications for Androgen-Independent Prostate Cancer," Endocrinology, Filed for Case IPR2016-00286, Janssen Exhibit 2024, on May 2002, vol. 143, No. 5, pp. 1889-1900.
Kruit et al.. Effect of combination therapy with aminoglutethimide and hydrocortisone on prostate-specific antigen response in metastatic prostate cancer refractory to standard endocrine therapy, Anti-Cancer Drugs, 2004, vol. 15, No. 9, pp. 843-847.
Kuzel et al., "A Phase II Study of Continuous Infusion 5-Fluorouracil in Advanced Hormone Refractory Prostate Cancer", Cancer, file for Case IPR2016-00286, Janssen Exhibit 2054, vol. 72, No. 6, on Sep. 15, 1993, 1965-1968 pages.
Lam et al., "Secondary Hormonal Therapy for Advanced Prostate Cancer," J Urology, vol. 175(1):27-34 (2006).
Lara and Meyers, "Treatment Options in Androgen-Independent Prostate Cancer" Cancer Investigation, file for Case IPR2016-00286, Janssen Exhibit 2053, vol. 17, No. 2, on 1999, pp. 137-144.
Lesaffre et al., "Statistical controversies in clinical research: futility analyses in oncology—lessons on potential pitfalls from a randomized controlled trial," Annals of Oncology, vol. 28, 2017, pp. 1419-1426.
Li et al. AR-induced brcaness and part inhibition in preclinical studies; Sci Signal 10: eaam7479, 2017.
Li et al. targeting parp/cmyk in prostate cancer, with olaparib tested in vivo in Vcap model; Sci Signal 7: ra47; 2014.
Ling et al., "17-imidazolyl, pyrazolyl, and isoxazolyl androstene derivatives, Novel steroidal inhibitors of human cytochrome C1720-lyase (P45017alpha):" J, Med. Chem., vol. 40:3297-3304 (1997).
Logothetis et al., "Effect of abiraterone acetate and prednisone compared with placebo and prednisone on pain control and skeletal-related events in patients with metastatic castration-resistant prostate cancer:exploratory analysis of data from the COU-AA-301 randomised trial", Lancet Oneal, 13, pp. 1210-1217,2012.
Logothetis et al., "Identification of an androgen withdrawal responsive phenotype in castrate resistant prostate cancer (CRPC) patients (pts) treated with abiraterone acetate (Aa)," J. Clin. Oncol. (Meeting abstracts), vol. 26 (May 20 Supplement), abstract No. 5017 (2008).
Lupo et al., "Inhibition of poly(ADP-ribosyl)ation in cancer: old and new paradigms revisited", Biochim Biophys Acta, Aug. 2014, vol. 1846, No. 1, pp. 201-215.
Luthy et al., "Androgenic Activity of Synthetic Progestins and Spironoladone in Androgen-Sensitive Mouse Mammary Carcinoma (Shionogi) Cells in Culture", J. Steroid Biochem, vol. 31, No., 5 • 1988. pp. 845-852.
Madan Ravi A et al. Abiraterone Cougar Biotechnology Idrugs, Current Drugs LTD, GB, vol. 9, No. 1, 2006, pp. 49-55.
Mantero et al., "Long-term treatment of mineralocorticoid excess syndromes", Divisions of Endocrinology, Universities of Padua and Ancona, Italy, Steroids, file for Case IPR2016-00286, Janssen Exhibit 2066, on Jan. 1995, vol. 60 pp. 81-86.
Marc B- Garnick, "Management of Metastatic Carcinoma of the Prostate—Treatment Options and Controversies", in Prostatic Disorders, (David F. Paulson et al. eds., 1989), pp. 354-367.
Maria I., "Male pseudohermaphroditism due to 17 alpha-hydroxylase deficiency", Journal of Clinical Investigation 1970, vol. 49 No. 10 pp. 1930-1941.
Marik PE et al., Recommendations for the diagnosis and management of corticosteroid insufficiency in critically Ill adult patients consensus statements from an international task force by the American College of Critical Care Medicine. Critical Care Medicine 2008, vol. 36, No. 6, pp. 1937-1949.
Marinan Fakih et al., "Glucocorticoids and Treatment of Prostate Cancer: a Preclinical and Clinical Review". Urology 60. 2002, pp. 553-561.
Marini et al., "The effect of adjuvant prednisone combined with GMF on patterns of relapse and occurrence of second malignancies in patients with breast cancer", Annals of Oncology, file for Case IPR2016-00286, Janssen Exhibit 2060, on 1996, vol. 7, pp. 245-250.
Mark. J. Ratain et al., Statistical and Ethical Issues in the Design and Conduct of Phase land II Clinical Trials of New Anticancer Agents, Journal of the National Cancer Institute, vol. 85, No. 20, pp. 1637-1649, Oct. 20, 1993.
Marketing authorization for Zytiga, European Commission, Sep. 5, 2011, pp. 31.
Martins et al., "A Validated Liquid Chromatographic-Tandem Mass Spectroscopy Method for the Quantification of Abiraterone Acetate and Abiraterone in Human Plasma," J. Chromatography B, vol. 843:262-257 (2006).

(56) References Cited

OTHER PUBLICATIONS

Masuda et al., Promise of vitamin D analogues in the treatment of hyperproliferative conditions, Mol. Cancer Ther., vol. 5(4) pp. 797-808 (2006).
Mateo et al., TOPARP study reported in NEJM 373:1697-olaparib treatment of prostate cancer patients, 2015.
Mateo et al., "DNA-Repair Defects and Olaparib in Metastatic Prostate Cancer", The New England Journal of Medicine, 2015, vol. 373, No. 18, pp. 1697-1708.
Mayo Clinic "Prednisone and other corticosteroids" for Case# IPR2016-002S6 Janssen Exhibit 2102 Oct. 3, 2016 4 Pages.
Mayo Clinic Website, "Prostate cancer", http://www.mayoclinic.org/diseasesconditions/prostatecancer/basics/definition/con-20029597?p=1 (accessed Jun. 28, 2016), Mylan Pharms. Inc., Exhibit 1051, 11 pages.
Mckay et al., "A phase II trial of abiraterone acetate (AA) without prednisone in castration resistant prostate cancer (CRPC)", Genitourinary (Prostate) Cancer, An American Society of Clinical Oncology Journal, 2017, 5 pages.
McPhaul. Michael J., "Mechanisms of Prostate Cancer Progression to Androgen Independence," Best Practice & Research Clinical Endocrinology & Metabolism. vol. 22(2):373-388 (2008).
Medical Dictionary, "Refractory cancer definition of refractory cancer by Medical dictionary" Janssen Exhibit 2103 *Amerigen* vs. *Janssen* filed for Case# IPR2016-00286. Oct. 3, 2016, 1 page.
MedlinePlus, MACTH stimulation test, Available at https://medlineplus.govtency/artide/003696.htm, last visited Sep. 30, 2016, file for Case IPR2016-00286, Janssen Exhibit 2050, 4 pages.
Melby JC et al., "Comparative studies on adrenal cortical function and cortisol metabolism in healthy adults and in patients with shock due to infection", Journal Clin Invest 1958, vol. 37 No. 12 pp. 1791-1798.
Mendel et al., "In vivo antitumor activity of SU11248, a novel tyrosine kinase inhibitor targeting vascular endothelial growth factor and platelet-derived growth factor receptors determination of a pharmacokinetic/pharmacodynamic relationship", Clinical Cancer Research, Jan. 2003. vol. 9, No. 1. pp. 327-337.
Michaelson et al., "Randomized, Placebo-Controlled, Phase III Trial of Sunitinib Plus Prednisone Versus Prednisone Alone in Progressive, Metastatic, Castration-Resistant Prostate Cancer." Journal of Clinical Oncology, vol. 31. pp. 1-8, (2013).
Michie, C.O., et al., "Final results of the phase I trial of niraparib (MK4827), a poly(ADP)ribose polymerase (PARP) inhibitor incorporating proof of concept biomarker studies and expansion cohorts involving BRCA1/2 mutation carriers, sporadic ovarian, and castration resistant prostate cancer (CRPC)," Journal of Clinical Oncology, vol. 31, No. 15, suppl, May 20, 2013, pp. 2513-2513.
Millikan, et al., "Randomized phase 2 trial of ketoconazole and ketoconazole/doxorubicin in androgen independent prostate cancer" Urologic Oncology, file for Case IPR2016-00286, Janssen Exhibit 2064, on 2001. vol. 6, pp. 111-115.
Milliken et al., EB1089, a vitamin D receptor agonist, reduces proliferation and decreases tumor growth rate in a mouse model of hormone-factuced mammary cancer, Cancer letters, New York, NY, vol. 229 (2):205-215 (2005).
Monetizing Focus: Tesaro Adds Runway by Out-licensing Niraparib In Prostate Cancer, Pink sheet, Apr. 6, 2016, pp. 1-3.
Moreira et al., "CYP17 Inhibitors for Prostate Cancer Treatment—An Update," Current Medicinal Chemistry), vol. 15:888-899 (2008).
Moreira et al., Synthesis and evaluation of novel 17-indazole androstene derivatives designed as CYP17 inhibitors, Elsevier, 2007, pp. 939-948, vol. 72.
Morgan et al., "Impact of prednisone on toxicities and survival in metastatic castration-resistant prostate cancer: A systematic review and meta-analysis of randomized clinical trials", Critical Reviews in Oncology/Hematology, Jun. 2014, vol. 90, No. 3, pp. 253-261.
Morioka et al., Prostate-Specific Antigen Levels and Prognosis in Patients with Hormone-Refractory Prostate Cancer Treated with Low-Dose Dexamethasone, Urologia Internationalis vol. 68, at 10-15 (2002).
Mostaghel et al., "Intracrine Androgen Metabolism in Prostate Cancer Progression: Mechanisms of Castration Resistance and Therapeutic Implications," Best Practice & Research Clinical Endocrinology & Metabolism, vol. 22(2) 243-258 (2008).
Mostaghel, E.A., "Abiraterone in the treatment of metastatic castration-resistant prostate cancer", Cancer Management Res. (2014) 6, p. 39-51.
Mostaghel, EA et al. Molecular Pathways Targeting resistance in the androgen receptor for therapeutic benefit, Clin. Cancer Res, Dec. 4, 2013.
Mottet et al., "Highlights on Prostate Cancer from Urological and Oncological Congresses in 2007," European Urology Supplements, vol. 7:460-476 (2008).
Mulcahy, Phase 3 Trial of Immuriotherapy for Metastatic Prostate Cancer Terminated Janssen Exhibit 2082 *Amerigen* vs. *Janssen* for Case#. IPR2016v0028-6, Oct. 17, 2008, 2 Pages.
Murai et al., parp inhibitor resistance mediated by SLFN11 inactivation; Oncotarget 7;76534, 2016.
Murai, et al., "Differential trapping of PARP1 and PARP2 by clinical PARP inhibitors", National Institute of Health, Cancer Res. Nov. 1, 2012; 72(21): 5588-5599.
Murphy W.J. JL Orcutt & P.C. Remus (2012) Patent Valuation: Improving Decision Making through Analysis Hoboken NJ: Wiley.
N. Rornero-Laorden et al., Prospective Evaluation of the Response to Prednisone-Dexamethasone Switch in Castration-Resistant Prostate Cancer Patients Treated with abiraterone pre-and post-docetaxel, Journal of Clinical Oncology vol. 34, Nov. 14, 2016.
Nakabayashi, M.,. et al.. "Response to Low-Dose Ketoconazole and Subsequent Dose Escalation to High-Dose Ketoconazole in Patients with Androgen-Independent Prostate Cancer", Amer Canc. Soc., 107(5), (2006) pp. 975-981.
National Cancer Institute-seer Stat Fact Sheets: Prostate Cancer Janssen Exhibit 2089, *Amerigen* vs. *Janssen* filed for case # IPR2016-00286, Oct. 3, 2016, pp. 1-11.
NCCN Practice Guidelines in Oncology. V. 1.2005, Prostate Cancer, 41 pages.
NCT01576172, "Abiraterone Acetate and Prednisone With or Without Veliparib in Treating Patients With Metastatic Castration-Resistant Prostate Cancer", ClinicalTrials.gov, Apr. 12, 2012.
NCT01715285 Clinicaltrials.gov, History of Changes for Study: NCT01715285 A Study of Abiraterone Acetate Plus Low-Dose Prednisone Plus Androgen Deprivation Therapy (ADT) Versus ADT Alone in Newly Diagnosed Participants With High-Risk, Metastatic Hormone-Naive Prostate Cancer (mHNPC), Sep. 19, 2019, 13 pages.
NCT01867710 Clinicaltrials gov, "A Randomized Phase 2 Study Evaluating Abiraterone Acetate With Different Steroid Regimens for Preventing Symptoms Associated With Mineralocorticoid Excess in Asymptomatic, Chemotherapy-native and Metastatic Castration-resistant Prostate Cancer (mCRPC) Patients" file for Case IPR2016-00286, Amerigen Exhibit 1187, on Jan. 14, 2017, 4 pages.
New Treatment for Prostate Cancer Under Development May 22, 1996 Wed for Case#. IPR2016-01582.
Newell et al. The Cancer Research UK experience of pre-clinical toxicology studies to support early clinical trials with novel cancer therapies, Elsevier, 2004, pp. 899-906, vol. 40.
Nimalasena et al.,. "Paraneoplastic Cushing's Syndrome in Prostate Cancer: A Difficult Management Problem," BJU International, vol. 101:424-427 (2007).
Nishimura, Kazuo, et al. Potential Mechanism for the Effects of Dexamethasone on Growth of Androgen-Independent Prostate Cancer, Journal of the National Cancer Institute, 2001, pp. 1739-1746, vol. 93.
Nishiyama, et al., Hormone/Antihormone Withdrawal and Dexamethasone, for Hormone—Refractory Prostate Cancer, international Journal of Urology, 10, 1997, vol. 5, 44-47.
Nnane et al., Inhibition of Androgen Synthesis in Human Testicular and Prostatic Microsomes and in Male Rats by Novel Steroidal Compounds, Endocrinology, 1999, pp. 2891-2897. vol. 140 No. 6.
O'Donnell et al., "Hormonal impact of the 17 (Alpha)-hydroxylase/C 17,20-lyase inhibitor abiraterone acetate (CB7 630) in patients with prostate cancer" British Journal of Cancer, 2004, vol. 90, No. 12, pp. 2317-2325.

(56) References Cited

OTHER PUBLICATIONS

Oelkers W. et al., Dose-response relationships between plasma adrenocorticotropin (ACTH), cortisol, aldosterone, and 18-hydroxycorticosterone after injection of ACTH-(1-39) of human corticotropin-releasing hormone in man, Journal of Clinical Endocrinology Metabolism, 1988, vol. 66, No. 1, pp. 181-186.
Official Journal of the American Urological Association, "Prostate Cancer", Journal Urology, vol. 177, No. 4, Apr. 2007, 2 pages..
Official Journal of the American Urological Association, Inc., "The Journal of Urology", vol. 135, Numbet 4, part 2, filed for Case, IPR2016-00286, Janssen Exhibit 2022 on Apr. 1986, 203A pages, Abstract 397.
Oh W. K., "Secondary hormonal therapies in the treatment of prostate cancer", Urology 60(Supp. 3A): pp. 87-93, (Sep. 2002).
Ohlmann C.H et al., "Androgendeprivation plus Abiraterone/ Prednisone beim metastasierten hormon• sensitiven Prostatakarzinom", Jul. 21, 2017, pp. 1185-1186.
Oliver Sartor et al., Effect of Prednisone on Prostate-Specific Antigen in Patients With Hormone-Refractory Prostate Cancer, Urology, 52: 1998, pp. 252-256.
Olmos et al., "Reply: Clnical Outcome and Prognostic Factors for Patients Treated Within a Phase I Study: The Royal Marsden Hospital Experience," British Journal of Cancer, vol. 99:1365 (2008).
OncoGenex Announces Top-Line Survival Results of Phase 3 SYNERGY Trial Evaluating Custirsen for Metastatic Castrate-Resistant Prostate Cancer, Janssen Exhibit 2077, *Amerigen* vs. *Janssen*, filed for Case# IPR2016-00286, Apr. 28, 2014, 2 Page.
Opar, Alisa, Asco Presentations Highlight Value of Cancer Biomarkers,: Nature Reviews, vol. 7:547-548 (2008).
Osaba, D., et al., "Health-Related Quality of Life in Men with Metastatic Prostate Cancer Treated with Prednisone alone or Mitoxantrone and Prednisone"< J Clin. Oncol. (1999), 17(6), p. 165-1663.
Osborne, "Historic' and 'practice-changing' Zytiga delivers in prostate cancer at ASCO", 2017, 2 pages.
Ospina et al., "ACTH Stimulation Tests for the Diagnosis of Adrenal Insufficiency: Systematic Review and Meta-Analysis", The Journal of Clinical Endocrinology & Metabolism Feb. 2016, vol. 101 No. 2 pp. 427-434.
Oudard et al., "Actualite dans le cancer de la prostate", Synthese, Bull Cancer 2005; 92 (10), pp. 865-873 (relevance in English abstract).
Palma et al., "ABT-888 Confers Broad In vivo Activity in Combination with Temozolomide in Diverse Tumors", Cancer Therapy: Preclinical, Dec. 1, 2009, pp. 7277-7290.
Palmer, "Managing Hyperkalemia Caused by Inhibitors of the Renin-Angiotensin-Aldosterone System", New England Journal of Medicine, file for Case IPR2016-01332, Janssen Exhibit 2067 on Aug. 5, 2004, vol. 351, No. 6, pp. 585-592.
Paltiel et al., Management of severe hypokalemia in hospitalized patents: a study of quality of care based on computerized databases, Arch Intern Med. Apr. 23, 2001, vol. 161, No. 8, pp. 1089, 1095.
Papatsoris et al., "Novel Biological Agents for the Treatment of Hormone-Refractory Prostate Cancer (HRPC)", Current Medicinal Chemistry 2007, filed for Case IPR2016-00286, Janssen Exhibit 2010, vol. 12, pp. 277-296.
Papeo et al., "Poly(ADP-ribose) Polymerase Inhibition in Cancer Therapy: Are We Close to Maturity?", Expert Opinion on Therapeutic Patents, Oct. 2009, vol. 19, No. 10, pp. 1377-1400.
Patel et al., "Failure of Iniparib to Inhibit Poly(ADP-Ribose) Polymerase In Vitro", Clin Cancer Res, vol. 18, Issue 6, 2012, pp. 1655-1662.
Patent Owner Janssen Oncology, Inc., for U.S. Pat. No. 8,822,438, *Mylan* vs. *Janssen*, filed for case , PR2016-01332, Janssen Exhibit 2189, 2016, 86 pages.
PCT International Search Report for PCT/US2007/018770, published Feb. 28, 2008.
PCT Written Opinion of the International Searching Authority for PCT/US2007/018770, published Feb. 28, 2008.
Peehl et al., "Preclinical activity of Ketoconazole in combination with calcitriol or the vitamin D analogue EB 1089 in prostate cancer cells," J. Urology, vol. 168, pp. 1583-1588 (2002).
Perlmutter et al: "New Directions in Prostate Cancer Management Androgen Deprivation Therapy in the Treatment of Advanced Prostate Cancer", Reviews in Urology, vol. 9, Jan. 2007, pp. S3-S8.
Petrylak et al., "Docetaxel and Estramustine Compared with Mitoxantrone and Prednisone For Advanced Refractory Prostate Cancer", New England Journal of Medicine, file for Gase IPR2016-01582; Janssen Exhibit 2059, on Oct. 7, 2004, vol. 351, No. 15, pp. 1513-1520.
Petrylak, "Future Directions in the Treatment of Androgen-Independent Prostate Cancer," Urology 65 (Supplement 6A), pp. 8-13 (2005).
Petrylak, D.P., "New Paradigms for Advanced Prostate Cancer", Rev. Urol. (2007), 9, Suppl. 2, S3-S12.
Ph II Study to Evaluate Olaparib With Abiraterone in Treating Metastatic Castration Resistant Prostate Cancer, NCT01972217, First Posted Oct. 30, 2013.
Phillip et al., Targeting PARP in prostate cancer: novelty, pitfalls, and promise. Oncology, vol. 30, No. 5, May 15, 2016 p. 377-377.
PMLiVe Website, "Top 50 pharmaceutical products by Global Sales", http:pmlive.pmlive.com/top pharma list/Top 50 pharmaceutical produds by global sales (accessed Jun. 30, 2016), Mylan Pharms. Inc., Exhibit 1055, 3 pages.
Polkinghorn et al., AR singnaling regulates DNA repair in prostate cancer; Cancer discovery 3:1245, 2013.
Ponder et al., "Response to aminoglutethimide and cortisone acetate in advanced prostatic cancer", Br. J. Cancer, (1984) 50 , pp. 757-763.
Positive Phase II Data on Cougar Biotechnology's CB7630 Presented at Prostate Cancer Foundation Scientific Retreat, News Release, available at http://www.cougarbiotechnology.com (2008).
Posner. G.H. et al., A non-Calcemic Sulfone Version of the Vitamin D3 Analogue Seocalcitol (E81089): Chemical Synthesis, Biological Evaluation and Potency Enhancement of the Anticancer Drug Adriamycin, Bioorganic & Medicinal Chem. 9: 2365-71 (2001).
Postma, "Treatment of Prostate Cancer", Annals of Oncology, Sep. 2006, vol. 17, Supplement 10, x207-x210.
Potter et al. "A Convenient Large-Scale Synthesis of Abiraterone Acetate [3Beta-acetoxy-17-(3 pyridyl) androsta-5, 16-diene], a Potential New Drug for the Treatment of Prostate Cancer," Organic Preparations and Procedures Intl, vol. 29(1):123-134 (1997).
Potter et al., "Discovery of highly potent and selective enzyme inhibitors with potential for the treatment of prostate cancer; the important dual role of transition metal chemistry in both drug design and synthesis," Poster presented at the SmithKline Beecham Research Symposium, Robinson College, Cambridge. England (1993).
Potter et al., "Highly potent inhibitors of human cytochrome p. 450 (17alpha)," Poster presented at the third drug discovery and development symposium, San Diego, California (1993).
Potter et al., "Novel Steroidal Inhibitors of Human Cytochrome P4501711 (17alpha-Hydroxylase-C17.20- lyase): Potential Agents for the Treatment of Prostatic Cancer," J. Med. Chem, vol. 38:2463-2471 (1995).
Prednisone Side Effects from http://www.drugs.com/sfx/prednisone-side-effects.html?printable=1, (Jul. 8, 2010).
PredniSONE Tablets USP, 1 mg, 2.5 mg, 5 mg, 10 mg, 20 mg and 50 mg, PredniSONE Oral Solution USP, 5 mg per 5 mL and PredniSONE Intensol (Trademark) Oral Solution (Concentrate), 5 mg per mL, Revised Nov. 2012, 18 pages.
Prelone, Physician's Desk Reference, 54th edition 1959-1960 (2000).
Prostate Cancer End Points Workshop Jun. 21-22, 2004, Bethesda Marriott—Bethesda MD, 66 pages.
Prostate Cancer Principles and Practice, Taylor & Francis (2006) Chapter 93.
Public Citizen Press Room Release—"Antifunal Treatment Should Be Taken Off the Market, Public Citizen Tells FOAD,." Filed for Case IPR2016-00286, Janssen Exhibit 2019. on Feb. 24, 2015, 1 page.
R. Venkitararnan et al., A Randomised Phase 2 Trial of Dexamethasone Versus Prednisolone in Castration-resistant Prostate Cancer, European Urology, 67, pp. 673-679 (2015).

(56) References Cited

OTHER PUBLICATIONS

Raghavan et al., "Prostate Cancer: Moving Forward by Reinventing the Wheel . . . But This Time it is Round." J. Clin. Oncol, vol. 26(28):4535-4536 (2008).
Ramiah et al.. Clinical Endpoints for Drug Development in Prostate Cancer: Current Opinion in Urology, vol. 18:303-308 (2008).
Raritan, NJ, "Janssen Enters Worldwide Collaboration and License Agreement with TESARO, Inc., for Niraparib in Prostate Cancer", Apr. 6, 2016, pp. 2.
Rathkopf et al., "Updated Interim Efficacy Analysis and Long-Term Safety of Abiraterone Acetate in Metastatic Castration-Resistant Prostate Cancer Patients Without Prior Chemotherapy(COU-AA-302)". European Urology, filed for Case# IPR20•16-00286, No. 66, pp. 815-825, 2014.
Reid et al., "CYP17 Inhibition as a Hormonal Strategy for Prostate Cancer," Nature Clin. Prac. Urology, vol. 5(11):610-620 (2008).
Reid et al., "Inhibition of Androgen Synthesis Results in a High Response Rate in Castration Refractory Prostate Cancer (CRPC)," Annals of Oncol. Vol. 18 (Supp. 9): abstract No. 50PD: 173-74 (2007).
Reid et al., "Selective CYP17 Inhibition with Abiraterone Acetate (AA) Results in a High Response Rate (RR) in Castration-Resistant Prostate Cancer (CRPC) Confirming the Continued Importance of Targeting Androgen Receptor (AR) Signaling," ASCO 2008 Genitourinary Cancers Symposium, abstract No. 50 (2008).
Reid et al., "Significant and Sustained Antitumor Activity in Post-Docetaxel, Castration-Resistant Prostate Cancer With the CYP17 Inhibitor Abiraterone Acetate," J. Clin. Oncol., vol. 28:(9), pp. 1489-1495 (2010).
Reid, A., et al., "Annals of Oncology", Educational and Abstract Book of the ESMO Conference Lugano (ECLU), (2007), 18(Supplement 9), ix173-ix174. Abstract 50PD.
Remington—The Science and Practice of Pharmacy, 20th Edition, filed for Case IPR2016-01582, Janssen Exhibit 2026. on 2000, pp. 1363-1370.
Report to the Nation on Prostate Cancer 2004. Prostate Cancer Foundation.
Richard d. Auchus, "Steroid 17-hydroxylase and 17,20-lyase deficiencies, genetic and pharmacologic", Journal of Steroid Biochemistry & Molecular Biology, 2017, vol. 165, pp. 71-78.
Robert Twycross, "Corticosteroids in Advanced Cancer".filed for Case# IPR2016-00286, vol. 305, pp. 969-970, Oct. 24, 1992.
Ross et al., "Hormone Refractory Prostate Cancer: Choosing the Appropriate Treatment Option," Oncology, vol. 21(2):185-193 (2007).
Rowlands et al., Esters of 3-Pyridylacetic Acid that Combine Potent Inhibition of 17alpha- Hydroxylase/C17.20-lyase (Cytochrome P45017alpha) with Resistance to Esterase Hydrolysis, J. Med. Chem., vol. 38:4191-4197 (1995).
Ruben H Munoz, Akin Gump Strauss H,t.\uer & Feld LLP, "Zytiga IPR", Mailed for Cast> # IPR2016-00286, Jun. 29, 2016, 1 page.
Rumohr et al., "Current Chemotherapeutic approaches for androgen-independent prostate cancer", Current Opinion in Investigational Drug, Filed for Case IPR2016-01332. Janssen Exhibit 2027, on 2006, vol. 7. No. 6, pp. 529-533.
Runge, Marschall S., et al., Principles of Molecular Medicine; Second edition; (2006) Humana Press Inc. ISBN: • 1-58829-202-9. pp. 365-376 and 482-484.
Ryan et al. "Impact of Prior Ketoconazole Therapy on Response Proportion to Abiraterone Acetate, a 17 alpha hydroxylase C17,20-Lyase Inhibitor in Castration Resistant Prostate Cancer (CRPC)," presentation (2008).
Ryan et al. , "Impad of prior ketoconazole therapy on response proportion to abiraterone acetate, a 17-alpha hydroxylase C17,20-lyase inhibitor in castration resistant prostate cancer (CRPC)," J. Clin. Oncol. (Meeting abstracts), vol. 26 (May 20 Supplement), abstract No. 5018 (2008).
Ryan et al., "Abiraterone Acetate Plus Prednisone in Chemotherapy (Chemo)-Naive castration Resistant Prostate Cancer (CPRC) Patients Not Exposed to Ketoconazole: Results of a Multi-Center Phase II Study," 2009 Genitourinary cancers Symposium (Feb. 26-28, 2009). abstract Submission (2008).
Ryan et al., "Abiraterone acetate plus prednisone versus placebo plus prednisone in chemotherapy-naive men with metastatic castration-resistant prostate cancer (COU-AA-302): final overall survival analysis of a randomised, double- blind, placebo-controlled phase 3 study.", The Lancet. Oncology, vol. 16, No. 2, Feb. 2015 (Feb. 2015), pp. 152-160.
Ryan et al., "Dose-Ranging Study of the Safety and Pharmacokinetics of Atrasentan in Patients with Refractory Malignancies", Clinical Cancer Research, filed for IPR2016-00286, vol. 10, pp. 440&-4411, Jul. 1, 2004.
Ryan et al., "Effect of Concomitant Food Intake on Pharmacokinetics of Abiraterone Acetate, a 17 alpha Hydroxylase C17,20-Lyase Inhibitor in Castration-Resistant Prostate Cancer (CRPC)," Molecular Cancer Therapeutics (Dec. 2007), vol. 6(12):3527s, 2007 AACR•NCI-EORTC International Conference, Poster Session C, abstract No. C2 (2007).
Ryan et al., "Phase I clinical trial of the CYP17 inhibitor abiraterone acetate demonstrating clinical activity in patients with castration-resistant prostate cancer who received prior ketoconazole therapy", Journal of Clinical Oncology Mar. 20, 2010, vol. 28, No. 9, pp. 1481-1488.
Ryan et al., "Phase II Study of Abiraterone In Chemotherapy-Naive Metastatic Castration-Resistant Prostate Cancer Displaying Bone Flare Discordant with Serologic Response", Clinical Cancer Research, 2011, Filed for Case IPR2016-00286, Janssen Exhibit 2017, vol. 17, No., 14, pp. 4854-4861.
Ryan et al., "Phase I Evaluation of Abiraterone Acetate (CB7630), a 17 alpha hydroxylase C17,20-Lyase Inhibitor in Androgen-Independent Prostate Cancer (AIPC)." J. Clin. Oncol. vol. 25 (18S):250s, ASCO Annual Meeting Proceedings Part I, abstract No. 5064 (2007).
Ryan et al., "Phase I Evaluation of Abiraterone Acetate (CB7630), a 17-alpha hydroxylase C17,20-Lyase Inhibitor in Androgen-Independent Prostate Cancer (AIPG)." ASCO 2007 Prostate Cancer Symposium, abstract No. 278 (2007).
Ryan et al., "Prostate Specific Antigen Only Androgen Independent Prostate Cancer: Natural History, Challenges in Management and Clinical Trial Design." J, Urology, vol. 178:S25-S29 (2007).
Ryan et al., Abiraterone in Metastatic Prostate Cancer without Previous Chemotherapy, The New England Journal of Medicine, 368; 2, pp. 138-148 (Jan. 10, 2013).
Ryan, "Secondary Hormonal Manipulations in Prostate Cancer," Hematology/Oncology Clinics of North America, vol. 20(4).925-934 (2006).
Rydzewska et al., "Adding Abiraterone to Androgen Deprivation Therapy in Men with Metastatic Hormone-sensitive Prostate Cancer: A Systematic Review and Meta-analysis," European Journal of Cancer, vol. 84, 2017, pp. 88-101.
S, Halabi et al., Prostate-Specific Antigen Changes as Surrogate for Overall Survival in Men With Metastatic Castration-Resistant Prostate Cancer Treated With Second-Line Chemotherapy, Journal of Clinical Oncology, vol. 31, No., 31, pp. 3944-3950 (Nov. 1, 2013).
S, Wilkinson, S. and G, Chodak., "An Evaluation of Intermediate-Dose Ketoconazole in Hormone Refractory Prostate Cancer," European Urology, vol. 45, pp. 581-585, Nov. 26, 2004.
S. M. Withelm et al., BAY 43-9006 Exhibits Broad Spectrum Oral Antitumor Activity and Targets the RAF/MEKIERK Pathway and Receptor Tyrosine Kinases Involved in Tumor Progression and Angiogenesis, Cancer Research, filed for Case# IPR2016-00286, vol. 64, pp. 7099-7109, (Oct. 1, 2004).
S. Oudard et al., Prostate-Specific Antigen Doubling Time Before Onset of Chemotherapy as a Predictor of Survival for Hormone-Refractory Prostate Cancer Patients, Annals of Oncology vol. 18, pp. 1828-1833, (Nov. 2007).
S. Udhane et al., Specificity of Anti-Prostate Cancer CYP17A1 Inhibitors on Androgen Biosynthesis, Biochemical and Biophysical Research Communications, filed for Case# IPR2016-00286, vol. 477, pp. 1005-1010, (Elsevier 2016).
Saad et al, "Niraparib with androgen receptor-axis-targeted therapy in patients with metastatic castration-resistant prostate cancer: safety

(56) References Cited

OTHER PUBLICATIONS and pharmacokinetic results from a phase 1b study (BEDIVERE)", Cancer Chemother Pharmacol., vol. 88, Issue 1, Jul. 2021, pp. 25-37.
Sabroe, T.P. et al., "An Efficient Synthesis of a Key Intermediate for the Biologically Active Vitamin D Analogue. Seocalcitol", Organic Process Research & Dev. vol. 8(1): 133-35 (2004).
Sahu, B., et al., "FoxA1 Specifies Unique Androgen and Glucocorticoid Receptor Binding Events in Prostate Cancer Cells" Cancer Research (2013), vol. 73, pp. 1570-1580.
Sandhu et al. "Phase I Study of Poly(ADP)-Ribose Polymerase (PARP) Inhibitor MK-4827(MK) with Antitumour Activity in Sporadic Castration Resistant Prostate Cancer (CRPC)", Asia-Pac J. Clin. Oncol., vol. 8(Suppl. 1), pp. 29-34, 2012 (Abstract 112).
Sandhu et al., "Poly (ADP-ribose) polymerase (PARP) inhibitors for the treatment of advanced germline BRCA2 mutant prostate cancer", Annals of Oncology, 2013, vol. 24, Issue 5, p. 1416-1418.
Sandhu et al., "The poly(ADP-ribose) polymerase inhibitor niraparib (MK4827) in BRCA mutation carriers and patients with sporadic cancer: a phase 1 dose-escalation trial", Lancet Oncol 2013; 14: 882-892 (Supp Appendix attached).
Sandhu et al., Supplementary Appendix, The poly(ADP-ribose) polymerase inhibitor niraparib (MK4827) in BRCA mutation carriers and patients with sporadic cancer: a phase 1 dose-escalation trial. Lancet Oncology; published online Jun. 28; 2013, 1-14.
Sartor et al., "Combination therapy: Abiraterone prolongs survival in metastatic prostate cancer". Nature Reviews Cunical Oncology, Aug. 2, 2011, vol. 8, No., 9, pp. 515-516.
Sartor et al., "Novel Therapeutic Strategies for Metastatic Prostate Cancer in the Post-Docetaxel Setting", Academia- Pharma Intersect Genitourinary Cancer: Prostate, The Oncologist, Nov. 2, 2011. vol. 16, pp. 1487-1497.
Saunders et al., "Inhibition of breast and ovarian carcinoma cell growth by 1,25-dlhydroxyvitamin D3 combined with retinoic acid or dexamethasone," Anti-Cancer Drugs, Rapid Communications of Oxford, vol. 6 (4) 562-569 (1995).
Sawyer et al., "Phase I Study of an Oral Formulation of ZD9331 Administered Daily for 28 Days", Journal of Clinical Oncology, filed for IPR201&.00286, vol. 2.1, No. 9, pp. 1859-1865, May 1, 2003.
Scher et al., "Bicalutamide for Advanced Prostate Cancer: The Natural Versus Treated History of Disease", Journal of Clinical Oncology, file for Case IPR2016-00286, Janssen Exhibit 2055, vol. 15, No. 8 on Aug. 1997, pp. 2928-2938.
Scher et al., "Biology of Progressive, Castration-Resistant Prostate Cancer: Directed Therapies Targeting the Androgen-Receptor Signaling , Axis," J. Clin. Oncol. vol. 23(32):8253-61 (2005).
Scher H.I. et al., "Increased survival with enzalutamide in prostate cancer after chemotherapy" New Eng. J. Med., vol. 367 No. 13, Sep. 27, 2012, pp. 1187-1197.
Schiewer et al., Dual roles of PARP-1 promote cancer growth and progression, Cancer Discovery 2:1134, 2012.
Scholz, et al., Long-Term Outcome for Men with Androgen Independent Prostate Cancer Treated with Ketoconazole and Hydrocortisone, The Journal of Urology, 2005, pp. 1947-1952. vol. 173.
Schroder, "Progress in Understanding Androgen-Independent Prostate Cancer (APC): A Review of Potential Endocrine-Mediated Mechanisms," European Urology, vol. 53: 1129-1137 (2008).
Schulte et al.., The corticotropinreleasing hormone stimulation test a possible aid in the evaluation of patients with adrenal insufficiency Journal of Clinical Endocrinology Metabolism 1984, vol. 58 No. 6, pp. 1064-1067.
Seale and Compton, "Side-effects of corticosteroid agents", The Medical Journal of Australia vol. 144, No. 3 Feb. 3, 1986 pp. 139-142.
Seocalcitol Versus Placebo in Advanced Hepatocellular Carcinoma LEO Pharma Study http://www.clinicaltrials.gov/ c1/show,No. 100051532 (2004).
Sephton, et al., "Diurnal Cortisol Rhythm as a Predictor of Breast Cancer Survival", Journal of the National Cancer Institute, vol. 92, No. 12, Jun. 21, 2000, pp. 994-1000.
Seventy One Edition Physicians' Desk Reference, the trusted drug reference for over 70 years, 2017. PDR, 5 pages.
Sharifi et al.., "Secondary Hormonal Therapy for Prostate Cancer: What Lies on the Horizon," BJU International, vol. 101:271-74 (2007).
Sills, Irene N., et al., "17a•hydroxylase deficiency in a genetic male and female sibling pair", Int J. GynaecoL Obstet., (1981), 19, 473:479.
Small et al., "Antiandrogen Withdrawal Alone or in Combination with Ketoconazole in Androgen-Independent Prostate Cancer Patients: A Phase III Trial (CALGB 9583)" Journal of Clinical Oncology, file for Case IPR2016-01332, Janssen Exhibit 2063, on Mar. 15, 2004, vol. 22, No. 6, pp. 1025-1033,.
Small et al., "Second-Line Hormonal therapy for Advanced Prostate Cancer: A Shifting Paradigm", journal of Clinical Oncology, vol. 15, No. Jan. 1, 1997, pp. 382-388.
Small et al., The Case fot Socondary Hormaonal Therapies in the Chemotherapy Age, The Journal of Urology, 2006; pp. S66-S71, vol. 176.
Small, E.J., et al., "Simultaneous Antiandrogen Withdrawal and Treatment with Ketoconazole and Hydrocortisone in Patients with Advanced Prostate Carcinoma", Amer Canc. Soc., 80(9), (1997) pp. 1755-1759.
Smith et al., "Niraparib in patients with metastatic castration-resistant prostate cancer and DNA repair gene defects (GALAHAD): a multicentre, open-label, phase 2 trial", Lancet Oncol., Mar. 2022, 23(3): 362-373.
Sonino et al., "The Use of Ketoconazole as an Inhibitor of Steroid Production", New England Journal of Medicine, file for Case IPR2016 01332, Janssen Exhibit 2163, on Sep. 24, 1987, vol. 317, No. 13, pp. 812-818.
Sonpavde et al., Impact of single-agent daily prednisone on outcomes in men with metastatic castration-resistant prostate cancer, Prostate Cancer and Prostatic Diseases, Mar. 2017, vol. 20, No. 1, pp. 67-71.
St. Louis, A Division of J.B. Lippincott, Drug Facts and Comparisons. 1985 Edition, 13 pages.
Stamey et al., "Prostate-Specific Antigen as a Serum Marker for Adenocarcinoma of the Prostate," The New England journal of Medicine, vol. 317, No. 15, Oct. 8, 1987 pp. 909-916.
Stein, et al., Randomized Phase 2 Therapeutic Equivalence Study of Abiraterone Acetate Fine Particle Formulation vs. Originator Abiraterone Acetate In Patients With Metastatic Castration Resistant Prostate Cancer: The STAAR Study, Urologic Oncology: Seminars and Original Investigations. 36, 2018, 81.e9-81.e16.
Sternberg et al., Phase III Trial of Satraplatin, an Oral Platinum plus Prednisone vs. Prednisone alone in Patients with Hormone-Refractory Prostate Cancer, Oncology, 68, pp. 2-9 (2005).
Sternberg, "Systematic Chemotherapy and New Experimental Approaches in the Treatment of Metastalic Prostate Cancer," Annals of Oncol., vol. 19 (Sopp. 7):vii91-vii95 (2008).
Sternberg. "Hormone refractory metastatic prostate cancer", Annals of Oncology, file for Case IPR2016-00286, Janssen Exhibit 2056, on 1992, vol. 3, pp. 331-335.
Storlie. J.A., et al., "Prostate Specific Antigen Levels and Clinical Response to Low Dose Dexamethasone for Hormone-Refractory Metastatic Prostate Carcinoma", Cancer (1995) vol. 76, No. 1, p. 96-100.
Strother et al., "Novel cytotoxic and biological agents for prostate cancer" Where will the money be in 2005?, European Journal of Cancer 2005, filed for Case IPR2.016-00286, Janssen Exhibit 2008. vol. 41, pp. 954-964.
Study NCT03012321 "Abiraterone/Prednisone, Olaparib, or Abiraterone/Prednisone + Olaparib in Patients With Metastatic Castration-Resistant Prostate Cancer With DNA Repair Defects", Clinical Trials, NCT03012321, 2021, pp. 1-13, first posted Jan. 6, 2017.
Study Status and Contacts/Locations History of Changes for Study: NCT02924766 A Safety and Pharmacokinetics Study of Niraparib Plus Apalutamide in Men With Metastatic Castratio•• Resistant

(56) References Cited

OTHER PUBLICATIONS

Prostate Cancer (BEDIVERE), Retrieved from https://clinicaltrials.gov/study/NCT02924766?tab=history&a=1#StudyPageTop,(Mar. 21, 2023), XP093033276%5BA%5D1-21, Oct. 4, 2016, pp. 1-11.
Summary of Product Characteristics for Zytiga 250 mg tablets (Jan. 16, 2014).
Swartz and Dluhy, "Corticosteroids: Clinical Pharmacology and Therapeutic Use", Clinical Pharmacology and Therapeutic, Drugs, file for Case IPR2016-00286, Janssen Exhibit 2068, on 1978, vol. 16, pp. 238-255.
Sweeney et al., "Chemohormonal Therapy in Metastatic Hormone-Sensitive Prostate Cancer", New England Journal of Medicine, filed for Case *Wockhardt* vs. *Janssen* IPR2016-01582, Janssen Exhibit 2163, on Aug. 20, 2015, vol. 373, No. 8, pp. 737-746.
Szmulewitz et al., "Antiandrogen Therapy in Prostate Cancer," Update on Cancer Therapeutics, vol. 2:119-131 (2007).
T. Saika et al., Treatment of androgen-independent prostate cancer with dexamethasone: A prospective study in stage D2 patients, International Journal of Urology, 8, pp. 290-294 (2001).
Taichman et al.., "The evolving biology and treatment of prostate cancer", The Journal of Clinical Investigation, Sep. 2007, vol. 117, No. 9, 2351-2361.
Takeda et al., "Inhibitors of the Key Enzymes of Androgen Synthesis: Potential Agents as Targets for Prostate Cancer," Japanese Journal of Clinical Medicine, vol. 58(Suppl.):312-316 (2000); Partial Translation Included (Total pp. 14).
Tamic, R, et al., "Hormonal Effects of High Dose Medroxyprogesterone Acetate Treatment in Males with Renal or Prostatic Adenocarcinoma", (1988), vol. 22 (1), Abstract.
Tanagho, EA, et al., "The Leading Single-vol. Resource in Urology" Smith's General Urology, 16th Edition, (2004), Chapter 19, pp. 321-323; Chapter 22, pp. 380-385.
Tannock et al., Chemotherapy with mitoxantrone plus prednisone or prednisone alone for symptomatic hormone-resistant prostate cancer: a Canadian randomized trial with palliative end points, Journal of Clinical Oncology,. vol. 14,. (6):1756-1764 (1996).
Tannock et al., "Treatment of metastatic prostatic cancer with low-dose prednisone: evaluation of pain and quality of life as pragmatic indices of response," Journal of Clinical Oncology, vol. 7 590-597 (1989).
Tannock I. et al., "Docetaxel plus prednisone or mitoxantrone plus prednisone for advanced prostate cancer", N. Eng. J. Med. 351, Oct. 7, 2004, pp. 1502-1512.
Taplin, "Drug Insight Role of the Androgen Receptor in the Development and Progression of Prostate Cancer," Nature Clin. Practice Oncol, vol. 4(4):236-244 (2007).
TAXOTERE (docetaxel) Injection Concentrate, Aventis Pharmaceuticals Inc. (2005). prescribing information.
Taxotere label, May 2004, Mylan Pharms. Inc. Exhibit 1140.
Taxotere prescribing information (Dec. 2015), TAXOTERE (docetaxel) Injection Concentrate, Intravenous Infusion (IV). Initial U.S, Approval: 1996, 63 pages.
Taxotere(Registered)," RX Taxotere (Docetaxel) Injection Concentrate", InformatIn as of May 2004, 35 pages.
Tenuta et al., "Clinical trial risk in castration-resistant prostate cancer: immunotherapies show promise", BJUI, vol. 113, Issue 5b, 2014, pp. E82-E89.
TESARO Announces Global Prostate Cancer Collaboration and Licensing Agreement With Janssen, Apr. 6, 2016, pp. 1-2.
Tewari et al., "Long-Term Survival Probability in Men with Clinically Localized Prostate Cancer Treated Either Conservatively or with Definitive Treatment (Radiotherapy or Radical Prostatectomy)", Urology, Dec. 2006, vol. 68. Issue 6, 1268-1274.
Teyssonneau et al., "Prostate Cancer and PARP Inhibitors: Progress and Challenges", J Hematol Oncol, Mar. 2, 20219, vol. 14, No. 51, 19 Pages.
The Institute of Cancer Research, Abiraterone: a story of scientific innovation and commercial partnership, Making the discoveries that defeat cancer filed for IPR2016-00286 Oct. 3, 2016.
Theodore, "Cancers Genito-Urinaires," Oncologie, vol. 10:497-500 (2008).
Therasse et al., "New Guidelines to Evaluate the Response to Treatment in Solid Tumors Journal of the National Cancer Instituie", vol. 92, No. 3, Feb. 2, 2000 pp. 205-216.
Thirty Second Edition Physicians' Desk Reference, 1978, PDR, 6 pages.
Thorsell et al., "Structual Basis for Potency and Promiscuity in Poly(ADP-ribose) Polymerase (PARP) and Tankyrase Inhibitors", J. Med. Chem., vol. 60, 2017, pp. 1262-1271.
Toshihiko Yanase et al., "Deletion of a phenylalanine in the N-terminal region of human cytochrome P-450(17 alpha) results in partial combined 17 alpha-hydroxylase/17, 20-lyase deficiency" Journal of Biological Chemistry May 24, 1989, vol. 264 No. 30 pp. 18076-18082.
Tozer et al., "Introduction to Pharmacokinetics and Pharmacodynamics", The Quantitative Basis of Drug Therapy, 2006, 40 pages.
TRELSTAR (Trademark) Depot 3.75 mg (triptorelin pamoate for injectable suspension), Pharmacia &. Upjohn Company (2001), package insert.
TRELSTAR(Trademark) LA 11.25 mg (triptorelin pamoatefor injectable suspension), Pharmacia & Upjohn Company (2001), package insert.
Trepanier, "Glucocorticoids", Cliniciansbrief.com, Dec. 2005 5 pages.
Trial of Abiraterone Without Exogenous Glucocortiooids in Men With CRPC With Correlative Assessment of Hormone Intermediates, 2013, 10 pages.
Trump et al., "Phase II trial of high-dose, intermittent calcitriol (1,25 dihydroxyvitamin D3) and dexamethasone in androgen-independent prostate cancer," Cancer, vol. 106(10), pp. 2136-2142 (2006).
Truven Commercial and Medicare Data, *Wockhardt* vs. *Janssen*, Filed for case IPR2016-01332, Janssen Exhibit 2135, 2016, 12 pages.
Tucker et al., "Reversible Adrenal Insufficiency Induced by Ketoconazole" Janssen Exhibit 2090, *Wockhardt* vs. *Janssen*, Case# IPR2016-01582, Jama, vol. 253, No. 16 Apr. 26, 1985, 2 Pages.
Twenty Nineth Edition Physicians' Desk Reference, 1975, PDR, 4 pages.
U,S. Patent. Alan H, Auerbach, et al., U.S. Pat. No. 8,822,438 B2, "Methods and Compositions for Treating Cancer", filed for Case# 15-cv-05909-KM-JBC, Document# 288-1, filed on Feb. 13, 2017, p. 2 of 13.
U.S. Food and Drug Administration ("FDA"), "Fda Approves New Indication for Taxotere-Prostate Cancer", FDA News Release dated May 19, 2004, 2 pages.
U.S. Food and Drug Administration FDA News Release, "FDA expands Zytiga's use for late-stage prostate cancer", Dec. 10, 2012 http://www.fda.gov/NewsEvents/Newsroom/PressAnnouncements/ucm331492.htm (access Jun. 30, 2016), 2 pages.
U.S. Food and Drug Administration, "FDA News Release", Press Announcements> FDA approves Zytiga for late-stage prostate cancer, Janssen Exhibit 2070, *Amerigen* v. *Janssen*, for Case# IPR2016-00286, Apr. 28, 2011, 2 Pages.
U.S. Food and Drug Administration, FDA Website Drugs@FDA—Zytiga, http://www.accessdata.fda.gov/scripts/cder/drugsatfda/index.cfm? fuseaction=Search.DrugDetails (accessed Jun. 28, 2016), Mylan Pharms, Inc., Exhibit 1046, 2 pages.
UBS Investment Research, "Johnson & Johnson—Zytiga Label Extended," Dec. 10, 2012.
UBS Research, "Medivation—A look at the Growth and Share in Prostate Cancer," Feb. 3, 2014.
Understanding the role of prednisone In combination with ZYTIGA(Registered), (abiraterone acetate), Putting Prednisone in Perspective, 2011, 13 pages.
Understanding Zytiga Users "Urologist Success" Qualitative Research, Janssen Exhibit 2092, *Amerigen* vs. *Janssen* filed for Case# IPR2016-00286, Jan. 2014.
Veliparib (ABT-888) is a PARP inhibitor being investigated to treat non-small cell hmg cancer, BRCA breast cancer and ovarian cancer, 2019, https://www.abbvie.com/onr- science/pipeline.html.

(56) References Cited

OTHER PUBLICATIONS

Venkitaraman, R., et al., "Efficacy of low-Dose Dexamethasone in Castration-Refractory Prostate Cancer", BJU Int (2008), 101, pp. 1756-1764.
MADUR(Registered) (leuprolide acetate implant). Bayer Pharmaceuticals Corporation (2004), package insert.
Vidal et al., "Reversing Resistance to Targeted Therapy", vol. 16—Supplement No. 4, 2004, pp. 7-12.
Vijayakumar, S. et al., "Clinical Trials Involving Vitamin D Analogs in Prostate Cancer", Cancer J. vol. 11(5): 362-73 (2005).
Vink-Van Wijingaarden et al., "Inhibition of breast cancer cell growth by combined treatment with vitamin D3 analogues and tamoxifen," Cancer Research, American Association for Cancer Research, Baltimore, MD:5711-5717, abstract (1994).
Vitamin D Aids Chemotherapy for Advanced Prostate Cancer, http://www.supplementquality.com/efficacy/VitD.prostate chemo.html (2002).
Vitamin D Boosts Cancer Treatment, http://new-s.bbc.co.uk/l/hi/health/2961806.stm (2003).
Vivek K. Arora et al., Glucocorticoid Receptor Confers Resistance to Anti-Androgens by Bypassing Androgen Receptor Blockade, Cell, Dec. 5, 2013: 155(6): 1309-1322.
Vogelzang, N.J., Curriculum Vitae, 2010, 15 pages.
Wahlberg et al., "Family-wide chemical profiling and structural analysis of PARP and tankyrase inhibitors", Nature Biotechnology, vol. 30, No. 3, 2012, pp. 283-289.
Walsh et al., "Docetaxel Plus Prednisone or Mitoxantrone Plus Prednisone for Advanced Prostate Cancer," J Urology, vol. 173 :2 p. 456 (2005).
Wang, C., et al., "Hypertension due to 17a-Hydroxylase deficiency", Australian and New Zealand Journal of Medicine (1978), 8(3), p. 295-299.
Wedbush Quick Note, "Medivation: Zytiga Market Share Decline Accelerates From Last Quarter," Jul. 14. 2015.
Wells Fargo Securities, LLC., Equity Research, "Johnson & Johnson," Jun. 29, 2015.
What You Need to Know About Prostate Cancer, NIH Publication No. 12-1576 (2012) Janssen Exhibit 2091 Amerigen vs. Janssen filed for Case# IPR2016-00286.
White, "Synthesis and Metabolism of Corticosteroids," Principles and Practice of Endocrinology and Metabolism, Ed. Kenneth L Becker, Philadelphia: Lippincott Williams & Wilkins, Janssen Exhibit 2086 *Amerigen* vs. *Janssen* for Case# IPR2016-00286, 2001, Chapter 72, 704-714.
Whitworth, "Mechanism of glucocorticoid-induced hypertension," Kidney International. vol. 31:1213-1224 (1987).
Wikipedia, Corticosteroid, undated. website, 2013.
William Blair, "Biotechnology—Zytiga Fourth-Quarter Sales Imply Xtandi Strength," Jan. 22, 2013.
William D. Figg et al.. "A Randomized Phase Ii Trial of Ketoconazole Plus Alendronate Versus Ketoconazole Alone in Patients With Androgen Independent Prostate Cancer and Bone Metastases", the Journal of Urology, vol. 173. pp. 790-796, Mar. 2005.
Williams, "Discontinued Drugs in 2007: oncology drugs," Expert Opinion on Investigational Drugs, vol. 17 No. 12: pp. 1791-1816 (2008).
Written Opinion dated Jul. 13, 2018; International Application No. PCT/US2018/026661, 6 Pages.
Xiao-Yan Zhao et al.. , Glucocorticoids can promote androgen-independent growth of prostate cancer cells through a mutated androgen receptor, Nat Med vol. 6 No. 6, Jun. 2000, pp. 703-706.
Xu et al., Correlation between Prostate-Specific Antigen Kinetics and Overall Survival in Abiraterone Acetate-Treated Castration-Resistant Prostate Cancer Patients, Clinical Cancer Research, Jul. 15, 2015, vol. 21, No. 14 pp. 3170-3177.
Xu Yuxia et al., "Clinical Observation of Abiraterone Acetate and Prednisone on Patients with Castration resistant Prostate Cancer", Cancer Research on Prevention and Treatment, 2015, vol. 42, No. 4, pp. 382-384.
Yanase T et al., 17 alpha hydroxylase/17-20-lyase deficiency: from clinical investigation to molecular definition, Endocrine Reviews 1991; vol. 12 No. 1 pp. 91-108.
Yano et al., "Glucocorticoids Suppress Tumor Angiogenesis and In vivo Growth of Prostate Cancer Cells", Clinical Cancer Research, May 15, 2006, vol. 12. No. 10, pp. 3003-3009.
Yano, A., et al., "Glucocorticoids Suppress Tumor Lymphangiogenesis of Prostate Cancer Cells", Clin Cancer Res (2006), vol. 12, pp. 6012-6017.
Yap et al., "Abiraterone acetate, an oral irreversible inhibitor of CYP450C17, administered to castration refractory prostate cancer patients is safe, suppresses androgen and steroid precursor levels, and has a high degree of durable antitumor activity," J Urology, vol. 177(4 )p. 199 (2007).
Yap et al., "Targeting CYP17; Established and Novel Approaches in Prostate Cancer" Current Opinion in Pharmacology (Jul. 28, 2008), vol. 8:449-457 (2008).
Zafeiris Zaferiou et al.. in Balaji, Chapter 9, Abiraterone for the Treatment of mCRPC, *Amerigen* v. *Janssen*, Case# IPR2016-00286, pp. 125-155.
Zaferiou et al., Managing Metastatic Castration-Resistant Prostate Cancer in the Pre-chemotherapy Setting: A Changing Approach in the Era of New Targeted Agents, Drugs, 76:421-430, Feb. 12, 2016.
Zhang et al., Targeting the MYCN-PARP-DNA Damage Response Pathway in Neuroendocrine Prostate Cancer, Clin Cancer Res 24: 696, 2017.
Zhang et al. parp inhibitor treatment of neuroendocrine prostate cancer, Clin Cancer Res 24: 696, 2017.
Zhang et al., "Help-seeking behavior for erectile dysfunction: a clinic-based survey in China," Asian J Androl, 2014, vol. 16, Issue 1, pp. 131-135.
Zhang, "Poly(ADP-ribose) polymerase inhibitor: an evolving paradigm in the treatment of prostate cancer", Asian J. of Andrology, vol. 16, pp. 401-406, 2014.
Zhou et al., Asian Pacific Journal of Cancer Prevention, 2014; 15:1313-1320.
ZOLADEX (Registered) 10.8 mg (goserelin acetate implant), AstraZeneca (2004), package insert.
ZOLADEX (Registered) 3.6 mg (goserelin acetate implant), AstraZeneca (2004), package Insert.
Zytiga Brochure, Putting Prednisone in Perspective, "Prednisone reduces the incidence and severity of mineralocorticoid-related adverse reactions associated with ZYTIGA(Registered)", Janssen Biotech, INC. 2015 3/15.
Zytiga Label, May 20, 2015, ZYTIGA(Registered) (abiraterone acetate) Tablets For Oral Administration Initial U.S. Approval: 2011, May 2015, Mylan Pharms. Inc., Exhibit 1065, 30 pages.
Zytiga Presentation—Key Clinical Findings for Patients with mCRPC who have progressed on Androgen Deprivation Therapy, 2016, pp. 1-66.
Zytiga Promotional Brochure—A comparison of The Mechanisms of Action of Select Prostate Cancer Treatments, 2012, pp. 1-12.
Zytiga Promotional Brochure—for patients with mCRPC who received prior Chemotherapy containing Docetaxel, 2012, pp. 1-2.
Zytiga Promotional Brochure—in Men with mCRPC—Mechanism of Action, 2014, pp. 1-2.
Zytiga Promotional Brochure—Prednisone reduces the incidence and severity of mineralocorticoid-related adverse reactions with Zytiga, 2011, 1 page.
Zytiga Promotional Brochure—Zytiga (abiraterone acetate)—Introducing a New Option for Patients with mCRPC before Chemotherapy, 2012, pp. 1-103.
Zytiga Promotional Brochure-Zytiga abiraterone acetate—an Oral Androgen Biosynthesis Inhibitor, 2011, 1 page.
Zytiga Usage-total promotional spend Janssen Exhibit 2096 *Amerigen* vs. *Janssen* filed for Case# IPR2016-00286, 2016, 3 Pages.
Zytiga Website How Zytiga(Registered) (abiraterone acetate) Works, "ZYTIGA(Registered) Inhibits Androgen Production at 3 Sources—Including the Tumor Itself" https://www.zytiga.com/print/about-zytiga/how-zytliga-works (accessed Jun. 28, 2016).
Zytiga Website, About Zytiga(Registered) (abiraterone acetate), "Prescribed Oral Medication for Metastatic Castration -Resistant

(56) References Cited

OTHER PUBLICATIONS

Prostate Cancer", https:/www.zytiga,cornichoosing-zytiga/results-of-zytiga (accessed Apr. 3, 2017), 10 pages.
Zytiga, "Highlights of Alimta prescribing information," 2008, pp. 20.
Zytiga, "Orange Book: Approved Drug Products with Therapeutic Equivalence Evaluations", Amerigen 1035, Sep. 24, 2015, 2 pages.
ZYTIGA (Trademark) (abiraterone acetate) Tablets for Oral Administration Initial U.S. Approval Issued Apr. 2011. *Wockhardt* vs. *Janssen*, Filed for Case IPR2016-01582, Janssen Exhibit 2168, 22 pages.
Clinical Cancer Research, "A Journal of the American Association for Cancer Research", Letter to lan Judson, RE: "Manuscript# 030579, Hormonal impact of the 17a-hydroxylase/C17, 20-lyase inhibitor abiraterone acetate (CB7630) in patients with prostate cancer", Filed for case IPR2016-01332, Janssen Exhibit 2030, on May 12, 2003, 4 pages.
Cougar Bioledmology Announces, "Positive CB7630 Phase I Data at the AACR Innovations in Prostate Cancer Research Conference," News Release, available at http://www.cougarbiotechnology.com, 2006, 2 pages.
Cougar Biotechnology Announces, "Presentation of positive phase I and phase II data at ASCO Prostate Cancer Symposium", Cougar Biotechnology, Feb. 23, 2007, 3 pages.
Cougar Biotechnology Presents, "Positive CB7630 Phase II Data at Prostate Cancer Foundation Scientific Retreat," News Release, available at http://www.cougarbiotechnology.com, 2007, 3 pages.
Farmer et al., "Targeting the DNA repair defect in BRCA mutant cells as a therapeutic strategy", 434 Nature, 2005, 917-921.
Hu et al., "Dual-target inhibitors of poly (ADP-ribose) polymerase-1 for cancer therapy: Advances, challenges, and opportunities", 230 European Journal of Medicinal Chemistry, 2022, 18 pages.
NCT02500901, "Enzalutamide and Niraparib in the Treatment of Metastatic Castrate-Resistant Prostate Cancer (CRPC)", ClinicalTrials.gov, Jul. 17, 2015, 9 pages.
U.S. Food and Drug Administration, "Orange Book: Approved Drug Products with Therapeutic Equivalence Evaluations", *Wockhardt* v. *Janssen* IPR2016-00286 Janssen Exhibit 2107, Oct. 3, 2016, 1 page.
Wang et al., Significance of the TMPRSS2:ERG gene fusion in prostate cancer:, 16 Molecular Medicine Reports, 2017, 5450-5428.
Wyatt et al., "Genomic Alterations in Cell-Free DNA and Enzalutamide Resistance in Castration-Resistant Prostate Cancer", JAMA Oncology, 2016, 1598-1606.
Zhang et al., "Enzalutamide versus abiraterone acetate for the treatment of men with metastatic castration-resistant prostate cancer", 16 Expert Opinion on Pharmacotherapy, 2015, 473-485.
Zytiga Usage-prednisone information Janssen Exhibit 2095, *Amerigen* vs. *Janssen* filed for Case# IPR2016-00286, 2016, 8 pages.
Anonymous: "A Study of Niraparib in Combination With Abiraterone Acetate and Prednisone Versus Abiraterone Acetate and Prednisone for the Treatment of Participants With Deleterious Germline or Somatic Homologous Recombination Repair (HRR) Gene-Mutated Metastatic Castration-Sensitive Prostate Cancer (mCSPC) (AMPLITUDE)", Aug. 4, 2020, pp. 8.
Chi K.N. et al., "A phase III randomized, placebo-controlled, double-blind study of niraparib plus abiraterone acetate and prednisone versus abiraterone acetate and prednisone in patients with metastatic prostate cancer (NCT03748641)", Annals of Oncology, vol. 30, Supplement 5, Oct. 2019, pp. V354.
Chi K.N et al., "A phase III randomized, placebo-controlled, double-blind study of niraparib plus abiraterone acetate and prednisone versus abiraterone acetate and prednisone in patients with metastatic prostate cancer (MAGNITUDE)", 56th Annu Meet Am Soc Clin Oneal (ASCO), May 25, 2020, vol. 38, No. 15, pp. 5.
Damle et al., "Abstract 2134: Niraparib combined with abiraterone acetate inhibits the growth of BRCA2wt prostate tumors", Cancer Res, 2019, vol. 79.
European Medicines Agency: "Assessment report EMA—Procedure No. EMEA/H/C/004249/0000—Zejula", Committee for Medicinal Products for Human Use, Sep. 14, 2017, pp. 1-122.
Fizazi K. et al., "Abiraterone acetate plus prednisone in patients with newly diagnosed high-risk metastatic castration-sensitive prostate cancer (LATITUDE): final overall survival analysis of a randomised, double-blind, phase 3 trial", The Lancet Oncology, vol. 20, No. 5, Apr. 12, 2019, pp. 686-700.
Janssen research & Development, Llc "A Safety and Pharmacokinetics Study of Niraparib Plus an Androgen Receptor-Targeted Therapy in Men With Metastatic Castration-Resistant Prostate Cancer (BEDIVERE)", ClinicalTrials.gov, Oct. 5, 2016 (Oct. 5, 2016).
Jones et al., "A Poly(ADP-ribose) Polymerase (PARP) Inhibitor for the Treatment of Tumors with Defective Homologous Recombination", J. Med. Chem., Apr. 23, 2015, 58(8), 3302-3314.
Ratta R. et al., "PARP inhibitors as a new therapeutic option in metastatic prostate cancer: a systematic review", Prostate Cancer and Prostatic Diseases, 2020, May 4, 2020, vol. 23, pp. 549-560.
Saad et al., "Interim results of a phase Ib study of niraparib plus androgen receptor-targeted therapy in men with metastatic castration-resistant prostate cancer", Annals of Oncology, 2018, vol. 29, Supplement 8, 1 pp.
Chi et al., "Niraparib plus abiraterone acetate with prednisone in patients with metastatic castration-resistant prostate cancer and homologous recombination repair gene alterations: second interim analysis of the randomized phase III Magnitude trial," Annals of Oncology, Sep. 2023, vol. 34, Issue 9, 772-782, 23pp, (Supplemental Appendix attached).
Chi et al.,, "Niraparib and Abiraterone Acetate for Metastatic Castration-Resistant Prostate Cancer", J Clin Oncol., Mar. 23, 2023, vol. 41, No. 18, 3339-3351, 44pp, (Supplemental Appendix attached).
Armstrong et al., "Five-year Survival Prediction and Safety Outcomes with Enzalutamide in Men with Chemotherapy-naïve Metastatic Castration-resistant Prostate Cancer from the PREVAIL Trial", European Urology 78, 2020, 347-357.
De Simone et al., "Effect of binder and load solubility properties on HPMC granules produced by wet granulation process", J Drug Deliv Sci Tech, 2019, 513-520.
Guinney et al., "Prediction of overall survival for patients with metastatic castration-resistant prostate cancer: development of a prognostic model through a crowdsourced challenge with open clinical trial data", vol. 18, Jan. 2017, 132-142.
Halabi et al., "Updated Prognostic Model for Predicting Overall Survival in First-Line Chemotherapy for Patients With Metastatic Castration-Resistant Prostate Cancer", vol. 32, No. 7, Mar. 2014, 671-677.
Hoy, "Abiraterone Acetate: A Review of Its Use in Patients with Metastatic Castration-Resistant Prostate Cancer", 2013, 73:2077-2091.
Hwangbo et al., "Additivity predicts the efficacy of most approved combination therapies for advanced cancer", Nat Cancer. Dec. 2023;4(12):1693-1704.
Lin et al., "Prostate-specific antigen half-life: a new predictor of progressionfree survival and overall survival in Chinese prostate cancer patients", Asian Journal of Andrology, 2009, 11:443-450.
Sartor et al., "Metastatic Prostate Cancer", N Engl J Med 2018;378:645-657.

* cited by examiner

TREATMENT OF PROSTATE CANCER WITH A COMBINATION OF ABIRATERONE ACETATE, NIRAPARIB TOSYLATE MONOHYDRATE AND PREDNISONE

CROSS-REFERENCE TO RELATED APPLICATIONS

This application is the National Stage of International Patent Application No. PCT/EP2021/062180, filed May 7, 2021, which claims the benefit of European Patent Application No. 20173749.1, filed May 8, 2020; U.S. Provisional Application No. 63/142,919, filed Jan. 28, 2021; and U.S. Provisional Application No. 63/174,282, filed Apr. 13, 2021. The disclosures of the foregoing applications are incorporated herein by reference in their entireties for any and all purposes.

TECHNICAL FIELD OF THE INVENTION

The present disclosure relates to combinations of anti-cancer drugs, methods of treatment of prostate cancer with said combinations, and pharmaceutical formulations comprising said combinations.

BACKGROUND OF THE INVENTION

Prostate cancer is the most common non-cutaneous malignancy in men and the second leading cause of death in men from cancer in the western world.

Prostate cancer results from the uncontrolled growth of abnormal cells in the prostate gland. Once a prostate cancer tumor develops, androgens such as testosterone promote prostate cancer growth. At its early stages, localized prostate cancer is often curable with local therapy including, for example, surgical removal of the prostate gland and radiotherapy. However, when local therapy fails to cure prostate cancer, as it does in up to a third of men, the disease progresses into incurable metastatic disease (i.e., disease in which the cancer has spread from one part of the body to other parts).

Current therapeutic options for men with metastatic castration-resistant prostate cancer (mCRPC) that improve survival and limit progression include taxane-based chemotherapy, and androgen receptor-targeted agents such as apalutamide (ERLEADA®) and enzalutamide (XTANDI®).

Platinum-based chemotherapy has been tested in a number of clinical studies in molecularly unselected prostate cancer patients with limited results and significant toxicities.

More recently, abiraterone acetate (ZYTIGA®) plus prednisone has been approved for treating metastatic castrate resistant prostate cancer.

Niraparib is an orally available, highly selective poly (adenosine diphosphate [ADP]-ribose) polymerase (PARP) inhibitor, with activity against PARP-1 and PARP-2 deoxyribonucleic acid (DNA)-repair polymerases. Jones P, Wilcoxen K, Rowley M, Toniatti C. Niraparib: A Poly(ADP-ribose) Polymerase (PARP) Inhibitor for the Treatment of Tumors with Defective Homologous Recombination. J Med Chem. 2015 Apr. 23; 58(8):3302-3314.

PARPs are enzymes responsible for repair of DNA single-strand breaks (SSBs) through a process called base excision repair. PARP inhibition leads to an accumulation of unrepaired SSBs, which result in stalling and collapse of replication forks and, consequently, to double-stranded breaks (DSBs). Normally, DSBs are repaired through homologous recombination (HR). If not repaired, DSBs result in cell death. When tumor cells with DNA-repair defects involving the HR pathway (e.g., Breast Cancer genes [BRCA]-1/2) are treated with a PARP inhibitor, they are unable to efficiently and accurately repair DSBs, which creates a synthetic lethal condition. In men with metastatic castration-resistant prostate cancers (mCRPC), tumors with DNA-repair anomalies account for approximately 20% to 30% of the sporadic cancers.

There is a need for therapeutic options for prostate cancer patients who either do not respond initially or become refractory to the existing treatments. Importantly, there is an unmet need for therapeutic options for prostate cancer patients.

SUMMARY OF THE INVENTION

The present disclosure relates to a combination of abiraterone acetate and niraparib, which can be administered to a mammal, in particular a human, suffering from an androgen receptor (AR)-related disease or condition, in particular cancer, more in particular prostate cancer.

These pharmaceutical formulations are fixed dose combinations of abiraterone acetate and niraparib.

An objective of the present invention is to provide therapies against prostate cancer, including, among others, hormone-sensitive prostate cancer, hormone-naïve high-risk prostate cancer, castration-resistant prostate cancer, metastatic castration resistant prostate cancer (mCRPC), metastatic castration sensitive prostate cancer (mCSPC), non-metastatic castration resistant prostate cancer (nmCRPC), biochemical recurrent (BCR) prostate cancer, and localized prostate cancer (LPC).

An objective of the present invention is to provide free-dose combinations (FrDC) of abiraterone acetate and niraparib tosylate monohydrate; or fixed-dose combinations (FDC) comprising abiraterone acetate and niraparib tosylate monohydrate.

An objective of the present invention is to provide pharmaceutical formulations that support patient compliance, therapy adherence, and therapy efficiency.

An objective of the present invention is to provide pharmaceutical formulations that reduce the tablet burden of the patients, e.g., from six or four tablets of abiraterone acetate and niraparib tosylate monohydrate per day to three, or preferably two or one tablet(s) per day.

An objective of the present invention is to provide fixed-dose combination (FDC) pharmaceutical formulations with comparable or improved stability or shelf life to the drug dosage forms formulated separately.

An objective of the present invention is to provide fixed-dose combination pharmaceutical formulations which are bioequivalent to the drug dosage forms when administered in separate dosage forms.

An objective of the present invention is to provide fixed-dose combination pharmaceutical formulations with an immediate release profile for both abiraterone acetate and niraparib.

An objective of the present invention is to provide fixed-dose combination pharmaceutical formulations with a good content uniformity or homogeneous distribution of abiraterone acetate and niraparib tosylate monohydrate. In some aspects, the abiraterone acetate and niraparib tosylate monohydrate are homogeneously distributed within an intragranular phase. In some aspects, the abiraterone acetate and niraparib tosylate monohydrate are homogenously distributed within the dosage form, e.g., tablet. In some aspects, where abiraterone acetate and niraparib tosylate monohydrate are prepared in separate granules, the respective granules are homogenously distributed in a granule blend. Abiraterone acetate and niraparib tosylate monohydrate drug substances have different particles sizes ($d_{50}$ of 4-5 μm and $d_{50}$ around 50 μm, respectively), different bulk densities, and different contents (33% and 5-10% (w/w), respectively) in the fixed-dose combinations of the present invention. When blending these two drug substances as such, they are prone to segregation, which causes problems with homogeneity in the blend and therefore dosage control in individual tablets. Administering an FDC with accurate and consistent amounts of the two drug substances is critical for ensuring safety and efficacy.

Content uniformity may be impacted by formulation manufacturing conditions, such as the inlet air temperature, spray rate, inlet air flow during granulation, and loss on drying during granulation.

An objective of the present invention is to provide granules comprising abiraterone acetate and niraparib tosylate monohydrate with a good stratified content uniformity.

An objective of the present invention is to provide granules comprising abiraterone acetate and niraparib tosylate monohydrate with a desired particle size distribution, that may be expressed in values of $d_{10}$, $d_{50}$, and/or $d_{90}$. If the granules are too small, this could result in issues during compression when preparing tablets. If the granules are too large, this could result in differences in content uniformity and undesired segregation, issues with compression during tableting, and issues with the dissolution and bioavailability of the APIs.

An objective of the present invention is to provide an immediate release film-coated fixed-dose combination pharmaceutical formulation for oral administration, whose ingredients do not cause oxidative degradation of abiraterone acetate, an API known to be sensitive to such degradation. The presence of organic or inorganic impurities and/or degradants and/or metabolites if out of trend can have an impact on patient safety or efficacy of the therapy.

An objective of the present invention is to provide fixed-dose combination pharmaceutical formulations with comparable dissolution profiles for abiraterone acetate and niraparib tosylate monohydrate relative to each other. Such a dissolution profile can support use of a fixed-dose combination because both agents would be suitable for administration on the same schedule. Another objective of the present invention is to provide fixed-dose combination formulations with comparable or improved dissolution profiles for either one or both, and preferably both, active ingredients when compared to one or both of the respective drugs formulated separately, e.g., in their current commercially marketed formulations (such as abiraterone acetate tablets and niraparib tosylate monohydrate capsules). Dissolution profiles may be impacted by manufacturing conditions, such as the inlet air temperature, spray rate, inlet air flow during granulation, and by the tablet hardness.

An objective of the present invention is to provide fixed-dose combination pharmaceutical formulations with comparable or improved bioavailability for each drug when compared to the drugs dosed as separate formulations (e.g., in their currently marketed formulations, which are abiraterone acetate tablets and niraparib tosylate monohydrate capsules). Another objective of the present invention is to provide fixed-dose combination pharmaceutical formulations where the two active ingredients exhibit one or more comparable pharmacokinetic parameter relative to the separate formulations (e.g., similar or improved $T_{max}$ and/or $t_{1/2}$, or % $C_{max}$). Reduced bioavailability relative to single agent dosing, or bioavailability parameters that do not support the same dosing schedule for both agents would lead to low plasma levels and impact efficacy of the therapy and could require increasing the frequency of dosing, number of doses, or both.

An objective of the present invention is to provide an immediate release film-coated fixed-dose combination pharmaceutical formulation for oral administration comprising 500 mg of abiraterone acetate and either 50 mg or 100 mg of free base niraparib, in tosylate monohydrate form.

An objective of the present invention is to provide an immediate release film-coated fixed-dose combination pharmaceutical formulation for oral administration comprising 375 mg of abiraterone acetate and either 50 mg or 100 mg of free base niraparib, in tosylate monohydrate form.

An objective of the present invention is to provide an immediate release film-coated fixed-dose combination pharmaceutical formulation for oral administration comprising 250 mg of abiraterone acetate and either 50 mg or 100 mg of free base niraparib, in tosylate monohydrate form.

An objective of the present invention is to provide fixed-dose combination pharmaceutical formulations with comparable or increased efficacy (e.g., due to increased bioavailability at the same doses) when compared to the drugs dosed separately.

In view of the divergent physicochemical properties of abiraterone acetate (lipophilic and poorly bioavailable) and niraparib tosylate monohydrate (hydrophilic and moderately to highly bioavailable), it is also an objective of the present invention to provide a technical solution to formulators when compounding the two drugs together.

The present disclosure relates to a method for the treatment of prostate cancer in a male human patient comprising administering to the patient an effective amount of a pharmaceutical formulation comprising abiraterone acetate and niraparib tosylate monohydrate as described herein, plus a glucocorticoid, e.g., prednisone, hydrocortisone, dexamethasone, prednisolone, including methylprednisolone.

The present disclosure relates to a method for the treatment of mCRPC in a male human patient with mCRPC, the method comprising administering to the patient an effective amount of a pharmaceutical formulation comprising abiraterone acetate and niraparib tosylate monohydrate as described herein, plus prednisone. In an aspect, the mCRPC treatment is first-line (L1) treatment of mCRPC. In an aspect, the patient has not been treated with abiraterone acetate plus prednisone for more than 5 months. In an aspect, the patient is positive for homologous recombination deficiency (HRD), or the patient is not positive for HRD. In an aspect, the HRD status is detected by monoallelic or biallelic alterations in one or more DNA repair genes, including without being limited to, BRCA1 (Breast Cancer gene 1), BRCA2 (Breast Cancer gene 2), ATM (ataxia-telangiectasia mutated), FANCA (Fanconi Anemia Complementation Group A gene), PALB2 (Partner and Localizer of BRCA2 gene), CHEK2 (Checkpoint Kinase 2 gene), BRIP1 (BRCA1 Interacting Protein C-terminal Helicase 1 gene), HDAC2 (Histone deacetylase 2), or CDK12 (Cyclin Dependent Kinase 12). In an aspect, the patient has received gonadotropin releasing hormone agonists (GnRHa) therapy or has undergone bilateral orchiectomy, prior to the treatment with the pharmaceutical formulation, plus prednisone. In an aspect, GnRHa therapy continues during the treatment with the pharmaceutical formulation, plus prednisone, if not surgically castrated.

The present disclosure relates to a method for the treatment of mCSPC in a male human patient with mCSPC, such patient having deleterious germline or somatic homologous recombination repair (HRR) gene-mutated mCSPC, said method comprising administering to the patient an effective amount of a pharmaceutical formulation comprising abiraterone acetate and niraparib tosylate monohydrate as described herein, plus prednisone. In an aspect, the deleterious germline or somatic HRR gene mutation is in one or more genes, including without being limited to, BRCA1, BRCA2, BRIP1, CDK12, CHEK2, FANCA, PALB2, RAD51B (RAD51 paralog B), and RAD54L (RAD54-Like). In an aspect, the patient has undergone ADT prior to the treatment with the pharmaceutical formulation, plus prednisone. In an aspect, said ADT is a medical or surgical castration. In an aspect, said ADT started within 6 months, preferably at least 14 days, prior to the treatment with the pharmaceutical formulation, plus prednisone. In an aspect, the patient undergoes ADT during the treatment with the pharmaceutical formulation, plus prednisone. In an aspect, the patient has not undergone prior therapy with a next generation androgen signaling inhibitor therapy (e.g., abiraterone acetate, enzalutamide, apalutamide, darolutamide, nilutamide, flutamide, bicalutamide, and the like). In an aspect, the patient has received docetaxel or cabazitaxel prior to the treatment with the pharmaceutical formulation, plus prednisone. In an aspect, the patient has received radiation or surgical intervention, prior to the treatment with the pharmaceutical formulation, plus prednisone. In an aspect, the patient has received abiraterone acetate plus prednisone, prior to the treatment with the pharmaceutical formulation plus prednisone. In an aspect, the patient has received abiraterone acetate plus prednisone, during a month prior to the treatment with the pharmaceutical formulation plus prednisone. In an aspect, the patient has received treatments for localized prostate cancer, prior to the treatment with the pharmaceutical formulation plus prednisone. In an aspect, said treatments for localized prostate cancer have been completed at least 1 year prior to the treatment with the pharmaceutical formulation plus prednisone. In an aspect, said treatments for localized prostate cancer are up to 3 years of ADT including radiation therapy, prostatectomy, lymph node dissection, or systemic therapies.

The present disclosure relates to a method for the treatment of mCRPC in a male human patient with mCRPC, with or without DNA-repair gene defects (DRD) or HRD, and optionally with cyclin dependent kinase 12 (CDK12) pathogenic alterations, said method comprising administering to the patient an effective amount of a pharmaceutical formulation comprising abiraterone acetate and niraparib tosylate monohydrate as described herein, plus prednisone. In an aspect, the patient continues with GnRHa therapy during the treatment with the pharmaceutical formulation plus prednisone, if not surgically castrated. In an aspect, the patient has been exposed to anti-androgens selected from nilutamide, flutamide, bicalutamide, enzalutamide, apalutamide, darolutamide, and abiraterone acetate; prior to the treatment with the pharmaceutical formulation plus prednisone. In an aspect, said anti-androgens are washed-out prior to the treatment with the pharmaceutical formulation plus prednisone.

The present disclosure relates to a method for the treatment of high risk and/or lymph node positive prostate cancer in a male human patient with high risk and/or lymph node positive prostate cancer, said method comprising administering to the patient an effective amount of a pharmaceutical formulation comprising abiraterone acetate and niraparib tosylate monohydrate as described herein, plus prednisone and leuprorelin acetate, prior to, during, and after radiotherapy. In an aspect, said radiotherapy is stereotactic body radiotherapy (SBRT) or ultra-hypofractionated radiotherapy, with a total dose of about 37.5 to 40 grays (Gy).

The present disclosure relates to a method for the treatment of castration-naïve prostate cancer in a male human patient with castration-naïve prostate cancer, with or without metastases, said method comprising administering to the patient an effective amount of a pharmaceutical formulation comprising abiraterone acetate and niraparib tosylate monohydrate as described herein, plus prednisone. In an aspect, the patient continues with GnRHa therapy during the treatment with the pharmaceutical formulation plus prednisone, if not surgically castrated.

The present disclosure relates to a method for the treatment of biochemical recurrent prostate cancer in a male human patient with biochemical recurrent prostate cancer, said method comprising administering to the patient an effective amount of a pharmaceutical formulation comprising abiraterone acetate and niraparib tosylate monohydrate as described herein, plus prednisone. In an aspect, said biochemical recurrent prostate cancer is detected by: i) a prostate-specific antigen (PSA) rise of ≥2.0 ng/mL above the nadir; or ii) next generation imaging (NGI) including prostate-specific membrane antigen positron emission tomography (PSMA-PET). In an aspect, the patient is HRD biomarker positive, high risk, and/or with oligometastatic disease. In an aspect, the HRD biomarker positive is one or more of, without being limited to, BRCA1, BRCA2, ATM, BRIP1, CDK12, CDK17, CHEK2, FANCA, HDAC2, PALB2, PPP2R2A, RAD51B, and RAD54L.

The present disclosure relates to a method for the treatment of locally advanced prostate cancer in a male human patient with locally advanced prostate cancer and who is a candidate for primary radiotherapy, said method comprising administering to the patient an effective amount of a pharmaceutical formulation comprising abiraterone acetate and niraparib tosylate monohydrate as described herein, plus prednisone.

The present disclosure relates to a method for the treatment of mCRPC in a male human patient with mCRPC optionally having received prior chemotherapy comprising docetaxel or cabazitaxel, said method comprising administering to the patient an effective amount of a pharmaceutical formulation comprising abiraterone acetate and niraparib tosylate monohydrate as described herein, plus prednisone.

The present disclosure relates to a method for the treatment nmCRPC in a male human patient with nmCRPC, said method comprising administering to the patient an effective amount of a pharmaceutical formulation comprising abiraterone acetate and niraparib tosylate monohydrate as described herein, plus prednisone. In an aspect, the patient has a PSA doubling time equal to or less than 10 months and is HRD positive. In an aspect, the patient is HRD positive. In an aspect, the patient has high-risk BCR.

In the methods of treatment disclosed herein, said pharmaceutical formulation may be a free-dose combination (FrDC) of abiraterone acetate and niraparib tosylate monohydrate; or a fixed-dose combination (FDC) comprising abiraterone acetate and niraparib tosylate monohydrate. In an aspect, the FrDC or FDC comprise, each independently, about 50 mg eq. niraparib and about 500 mg abiraterone acetate; about 100 mg eq. niraparib and about 500 mg abiraterone acetate; about 50 mg eq. niraparib and about 375 mg abiraterone acetate; about 100 mg eq. niraparib and about 375 mg abiraterone acetate; about 50 mg eq. niraparib and about 250 mg abiraterone acetate; about 100 mg eq. niraparib and about 250 mg abiraterone acetate; about 33 mg eq. niraparib and about 333 mg abiraterone acetate; or about 67 mg eq. niraparib and about 333 mg abiraterone acetate. In an aspect, the FrDC or FDC are oral dosage forms. In an aspect, the oral dosage form is a tablet, a capsule, or a sachet.

In the methods of treatment disclosed herein, the fixed-dose combination (FDC) comprising abiraterone acetate and niraparib, preferably niraparib tosylate monohydrate, is as defined throughout the present disclosure.

The present disclosure relates to a pharmaceutical formulation comprising abiraterone acetate and niraparib tosylate monohydrate, as a combined preparation for simultaneous, separate or sequential use with prednisone, in treating prostate cancer in a patient, such as mCRPC, such as first-line (L1) mCRPC. In as aspect, the patient has not been treated with abiraterone acetate and prednisone for more than 5 months. In an aspect, the patient is positive for homologous recombination deficiency (HRD), or the patient is not positive for HRD. In an aspect, the HRD status is detected by monoallelic or biallelic alterations in one or more DNA repair genes, including without being limited to, BRCA1 (Breast Cancer gene 1), BRCA2 (Breast Cancer gene 2), ATM (ataxia-telangiectasia mutated), FANCA (Fanconi Anemia Complementation Group A gene), PALB2 (Partner and Localizer of BRCA2 gene), CHEK2 (Checkpoint Kinase 2 gene), BRIP1 (BRCA1 Interacting Protein C-terminal Helicase 1 gene), HDAC2 (Histone deacetylase 2), or CDK12 (Cyclin Dependent Kinase 12). In an aspect, the patient has received gonadotropin releasing hormone agonists (GnRHa) therapy or has undergone bilateral orchiectomy, prior to the treatment with the pharmaceutical formulation plus prednisone. In an aspect, the GnRHa therapy continues during the treatment with the pharmaceutical formulation plus prednisone, if not surgically castrated.

The present disclosure relates to a pharmaceutical formulation comprising abiraterone acetate and niraparib tosylate monohydrate, as a combined preparation for simultaneous, separate or sequential use with prednisone, in treating mCSPC in patients having deleterious germline or somatic homologous recombination repair (HRR) gene-mutated mCSPC. In an aspect, the deleterious germline or somatic HRR gene mutation is in one or more genes, including without being limited to, BRCA1, BRCA2, BRIP1, CDK12, CHEK2, FANCA, PALB2, RAD51B, and RAD54L. In an aspect, the patient has undergone ADT prior to the treatment with the pharmaceutical formulation plus prednisone. In an aspect, said ADT is medical or surgical castration. In an aspect, said ADT started within 6 months, preferably at least 14 days, prior to the treatment with the pharmaceutical formulation plus prednisone. In an aspect, the patient undergoes ADT during the treatment with the pharmaceutical formulation plus prednisone. In an aspect, the patient has not undergone prior therapy with a next generation androgen signaling inhibitor therapy (e.g., abiraterone acetate, enzalutamide, apalutamide, darolutamide, nilutamide, flutamide, bicalutamide, and the like). In an aspect, the patient has received docetaxel or cabazitaxel prior to the treatment with the pharmaceutical formulation plus prednisone. In an aspect, the patient has received radiation or surgical intervention, prior to the treatment with the pharmaceutical formulation plus prednisone. In an aspect, the patient has received abiraterone acetate plus prednisone, prior to the treatment with the pharmaceutical formulation plus prednisone. In an aspect, the patient has received abiraterone acetate plus prednisone, during a month prior to the treatment with the pharmaceutical formulation plus prednisone. In an aspect, the patient has received treatments for localized prostate cancer, prior to the treatment with the pharmaceutical formulation plus prednisone. In an aspect, said treatments for localized prostate cancer have been completed at least 1 year prior to the treatment with the pharmaceutical formulation plus prednisone. In an aspect, said treatments for localized prostate cancer are up to 3 years of ADT including radiation therapy, prostatectomy, lymph node dissection, or systemic therapies.

The present disclosure relates to a pharmaceutical formulation comprising abiraterone acetate and niraparib tosylate monohydrate, as a combined preparation for simultaneous, separate or sequential use plus prednisone, in treating mCRPC in patients with mCRPC, with or without DNA-repair gene defects (DRD) or HRD, and optionally with cyclin dependent kinase 12 (CDK12) pathogenic alterations. In an aspect, the patient continues with GnRHa therapy during the treatment with the pharmaceutical formulation plus prednisone, if not surgically castrated. In an aspect, the patient has been exposed to anti-androgens selected from nilutamide, flutamide, bicalutamide, enzalutamide, apalutamide, darolutamide, and abiraterone acetate; prior to the treatment with the pharmaceutical formulation plus prednisone. In an aspect, said anti-androgens are washed-out prior to the treatment with the pharmaceutical formulation plus prednisone.

The present disclosure relates to a pharmaceutical formulation comprising abiraterone acetate and niraparib tosylate monohydrate, as a combined preparation for simultaneous, separate or sequential use plus prednisone and leuprorelin acetate, in treating high risk and/or lymph node positive prostate cancer in patients having high risk and lymph node positive prostate cancer, prior to, during, and after radiotherapy. In an aspect, said radiotherapy is stereotactic body radiotherapy (SBRT) or ultra-hypofractionated radiotherapy, with a total dose of about 37.5 to 40 Gy.

The present disclosure relates to a pharmaceutical formulation comprising abiraterone acetate and niraparib tosylate monohydrate, as a combined preparation for simultaneous, separate or sequential use plus prednisone, in treating castration-naïve prostate cancer in patients having castration-naïve prostate cancer, with or without metastases. In an aspect, GnRHa therapy continues during the treatment with the pharmaceutical formulation plus prednisone, if not surgically castrated.

The present disclosure relates to a pharmaceutical formulation comprising abiraterone acetate and niraparib tosylate monohydrate, as a combined preparation for simultaneous, separate or sequential use plus prednisone, in treating biochemical recurrent prostate cancer in patients having biochemical recurrent prostate cancer. In an aspect, said biochemical recurrent prostate cancer is detected by: i) a prostate-specific antigen (PSA) rise of ≥2.0 ng/mL above the nadir; or ii) next generation imaging (NGI) including prostate-specific membrane antigen positron emission tomography (PSMA-PET). In an aspect, the patients are HRD biomarker positive, high risk, and/or with oligometastatic disease. In an aspect, the HRD biomarker positive is one or more of, without being limited to, BRCA1, BRCA2, ATM, BRIP1, CDK12, CDK17, CHEK2, FANCA, HDAC2, PALB2, PPP2R2A, RAD51B, and RAD54L.

The present disclosure relates to a pharmaceutical formulation comprising abiraterone acetate and niraparib tosylate monohydrate, as a combined preparation for simultaneous, separate or sequential use plus prednisone, in treating locally advanced prostate cancer in patients having locally advanced prostate cancer and who are candidates for primary radiotherapy.

The present disclosure relates to a pharmaceutical formulation comprising abiraterone acetate and niraparib tosylate monohydrate, as a combined preparation for simultaneous, separate or sequential use, plus prednisone, in treating mCRPC in patients having mCRPC optionally having received prior chemotherapy comprising docetaxel or cabazitaxel.

The present disclosure relates to a pharmaceutical formulation comprising abiraterone acetate and niraparib tosylate monohydrate, as a combined preparation for simultaneous, separate or sequential use, plus prednisone, in treating nmCRPC in patients having nmCRPC. In an aspect, the patients have a PSA doubling time equal to or less than 10 months and are HRD positive. In an aspect, the patients are HRD positive. In an aspect, the patients have high-risk BCR.

The pharmaceutical formulation for the uses disclosed herein may be a free-dose combination (FrDC) of abiraterone acetate and niraparib; or a fixed-dose combination (FDC) comprising abiraterone acetate and niraparib. The pharmaceutical formulation for the uses disclosed herein may be a FrDC of abiraterone acetate and niraparib tosylate monohydrate; or a FDC comprising abiraterone acetate and niraparib tosylate monohydrate. In an aspect, the FrDC or FDC comprise, each independently, about 50 mg niraparib eq. (equivalent to niraparib free base) and about 500 mg abiraterone acetate; about 100 mg niraparib eq. and about 500 mg abiraterone acetate; about 50 mg niraparib eq. and about 375 mg abiraterone acetate; about 100 mg niraparib eq. and about 375 mg abiraterone acetate; about 50 mg niraparib eq. and about 250 mg abiraterone acetate; about 100 mg niraparib eq. and about 250 mg abiraterone acetate; about 33 mg niraparib eq. and about 333 mg abiraterone acetate; or about 67 mg niraparib eq. and about 333 mg abiraterone acetate. In an aspect, the FrDC or FDC are oral dosage forms. In an aspect, the oral dosage form is a tablet, a capsule, or a sachet.

The fixed-dose combination (FDC) comprising abiraterone acetate and niraparib tosylate monohydrate (or niraparib) is as defined throughout the present disclosure.

The present disclosure relates to a granule composition comprising abiraterone acetate, niraparib, and a pharmaceutically acceptable carrier. The present disclosure relates to a pharmaceutical formulation, such as an oral dosage form, comprising the granule composition.

In an aspect, the granules consist essentially of abiraterone acetate, niraparib, and a pharmaceutically acceptable carrier. In an aspect, said granules have a particle size distribution with a $d_{50}$ of about 200 to about 500 μm, or of about 231 to about 396 μm; with a $d_{10}$ of about 50 to about 250 μm, or of about 93 to about 192 μm; and/or with a $d_{90}$ of about 500 to about 900 μm, or of about 616 to about 723 μm.

In an aspect, a first portion of the granules consists essentially of abiraterone acetate and a pharmaceutically acceptable carrier; and a second portion of the granules consists essentially of niraparib and a pharmaceutically acceptable carrier.

In an aspect, the niraparib is in the salt form of tosylate monohydrate, sulfate, benzenesulfate, fumarate, succinate, camphorate, mandelate, camsylate, lauryl sulfate, or a mixture of tosylate monohydrate and lauryl sulfate. In an aspect, the niraparib tosylate monohydrate is in crystal form. In an aspect, the abiraterone acetate is in crystal form. In an aspect, the present disclosure relates to a pharmaceutical formulation comprising niraparib lauryl sulfate and a pharmaceutically acceptable carrier. In an aspect, the present disclosure relates to a pharmaceutical formulation comprising a mixture of niraparib tosylate monohydrate and niraparib lauryl sulfate, and a pharmaceutically acceptable carrier.

In an aspect, the pharmaceutically acceptable carrier of the granule composition comprises a wetting agent, a diluent, a disintegrant, optionally a glidant, optionally a lubricant, and optionally a binder. In an aspect, the diluent is lactose, and said lactose is also used as a binder. In an aspect, the disintegrant is crospovidone.

The present disclosure further relates to a pharmaceutical formulation, e.g., an oral dosage form, comprising the granule composition described herein. In an aspect, the formulation or oral dosage form comprises about 50 mg niraparib eq. and about 500 mg abiraterone acetate; about 100 mg niraparib eq. and about 500 mg abiraterone acetate; about 50 mg niraparib eq. and about 375 mg abiraterone acetate; about 100 mg niraparib eq. and about 375 mg abiraterone acetate; about 50 mg niraparib eq. and about 250 mg abiraterone acetate; about 100 mg niraparib eq. and about 250 mg abiraterone acetate; about 33 mg niraparib eq. and about 333 mg abiraterone acetate; or about 67 mg niraparib eq. and about 333 mg abiraterone acetate.

In an aspect, the oral dosage form is a tablet, wherein the pharmaceutically acceptable carrier comprises a wetting agent, a diluent, a disintegrant, a glidant, a lubricant, optionally a binder, and optionally a coating material. In an aspect, the wetting agent is sodium lauryl sulfate (SLS) and is present in the dosage form in a percentage from about 3 to 6% (w/w). In an aspect, the wetting agent is SLS and is present in the final dosage forms in a by weight ratio versus abiraterone acetate of about 0.05:1 to 0.2:1 (SLS:abiraterone acetate), preferably about 0.1:1, more preferably about 0.11:1, about 0.12:1, or about 0.123:1. In an aspect, the SLS is present both in the intragranular and extragranular phases of the tablet. In an aspect, the disintegrant is crospovidone and is present both in the intragranular and extragranular phases of the tablet. In as aspect, the diluent of the extragranular phase is silicified microcrystalline cellulose. In an aspect, the tablet has a hardness of 250 to 350 N. In an aspect, the tablet has a stratified content uniformity from 75% to 125%, or from 90% to 110%. In an aspect, the tablet has a blend uniformity with a relative standard deviation up to 3%.

In an aspect, the tablet comprises about 500 mg of abiraterone acetate and about 50 mg of niraparib eq.; and wherein (i) greater than 40%, or about 50%, of abiraterone acetate dissolves after 5 minutes, (ii) greater than 75%, or about 80 or 81%, of abiraterone acetate dissolves after 10 minutes, (iii) greater than 85%, or about 89 or 90% of abiraterone acetate dissolves after 15 minutes, (iv) greater than 87%, or about 92%, of abiraterone acetate dissolves after 20 minutes; (v) greater than 90%, or about 95%, of abiraterone acetate dissolves after 30 minutes, (vi) greater than 91%, or about 96%, of abiraterone acetate dissolves after 45 minutes, (vii) greater than 92%, or about 97%, of abiraterone acetate dissolves after 60 minutes, (viii) greater than 93%, or about 98%, of abiraterone acetate dissolves after 90 minutes, or (ix) greater than 93%, or about 98%, of abiraterone acetate dissolves after 120 minutes; when measured by the USP Paddle method at 75 rpm in 900 mL of an aqueous solution comprising 0.05 mM sodium phosphate buffer with 0.25% (w/v) sodium lauryl sulfate at pH 4.5 and a temperature of 37.0±0.5° C.

In an aspect, the tablet comprises about 500 mg of abiraterone acetate and about 100 mg of niraparib eq.; and wherein (i) greater than 36%, or about 41%, of abiraterone acetate dissolves after 5 minutes, (ii) greater than 67%, or about 72%, of abiraterone acetate dissolves after 10 minutes, (iii) greater than 76%, or about 81%, of abiraterone acetate dissolves after 15 minutes, (iv) greater than 81%, or about 86%, of abiraterone acetate dissolves after 20 minutes, (v) greater than 85 or 86%, or about 90 or 91%, of abiraterone acetate dissolves after 30 minutes, (vi) greater than 90%, or about 95%, of abiraterone acetate dissolves after 45 minutes, (vii) greater than 90 or 91%, or about 95 or 96%, of abiraterone acetate dissolves after 60 minutes, (viii) greater than 93%, or about 98%, of abiraterone acetate dissolves after 90 minutes, or (ix) greater than 94%, or about 99%, of abiraterone acetate dissolves after 120 minutes; when measured by the USP Paddle method at 75 rpm in 900 mL of an aqueous solution comprising 0.05 mM sodium phosphate buffer with 0.25% (w/v) sodium lauryl sulfate at pH 4.5 and a temperature of 37.0±0.5° C.

In an aspect, the tablet comprises about 500 mg of abiraterone acetate and about 50 mg of niraparib eq.; and wherein (i) greater than 30 or 35%, or about 39 or 40%, of niraparib dissolves after 5 minutes, (ii) greater than 79 or 80%, or about 84 or 85%, of niraparib dissolves after 10 minutes, (iii) greater than 90%, or about 95%, of niraparib dissolves after 15 minutes, (iv) greater than 92%, or about 97%, of niraparib dissolves after 20 minutes, (v) greater than 93%, or about 98%, of niraparib dissolves after 30 minutes, (vi) greater than 93%, or about 98%, of niraparib dissolves after 45 minutes, (vii) greater than 93%, or about 98%, of niraparib dissolves after 60 minutes, (viii) greater than 93%, or about 98%, of niraparib dissolves after 90 minutes, or (ix) greater than 93%, or about 98%, of niraparib dissolves after 120 minutes; when measured by the USP Paddle method at 75 rpm in 900 mL of an aqueous solution comprising 0.05 mM sodium phosphate buffer with 0.25% (w/v) sodium lauryl sulfate at pH 4.5 and a temperature of 37.0±0.5° C.

In an aspect, the tablet comprises about 500 mg of abiraterone acetate and about 100 mg of niraparib eq.; and wherein (i) greater than 23%, or about 28%, of niraparib dissolves after 5 minutes, (ii) greater than 64%, or about 69%, of niraparib dissolves after 10 minutes, (iii) greater than 80 or 81%, or about 85 or 86%, of niraparib dissolves after 15 minutes, (iv) greater than 87%, or about 92%, of niraparib dissolves after 20 minutes, (v) greater than 90%, or about 95%, of niraparib dissolves after 30 minutes, (vi) greater than 91%, or about 96%, of niraparib dissolves after 45 minutes, (vii) greater than 92%, or about 97%, of niraparib dissolves after 60 minutes, (viii) greater than 92%, or about 97%, of niraparib dissolves after 90 minutes, or (ix) greater than 92%, or about 97%, of niraparib dissolves after 120 minutes; when measured by the USP Paddle method at 75 rpm in 900 mL of an aqueous solution comprising 0.05 mM sodium phosphate buffer with 0.25% (w/v) sodium lauryl sulfate at pH 4.5 and a temperature of 37.0±0.5° C.

In an aspect, the tablet dosage forms are bioequivalent, when administered orally on an equivalent dose basis, to free-dose combinations of abiraterone acetate and niraparib (e.g., wherein one or more pharmacokinetic parameters are within 20% or within 10% or within 5% of the respective values after dosing with free-dose combinations or single agents).

In an aspect, the oral dosage form is a capsule or a sachet, optionally further comprising a diluent.

In an aspect, the oral dosage form is a fixed-dose combination (FDC).

The present disclosure also relates to the pharmaceutical formulation or oral dosage form described herein, for use in the treatment of prostate cancer in a patient. Similarly, the present disclosure also relates to a method of treatment of prostate cancer in a patient, said method comprising administering to the patient said pharmaceutical formulation or oral dosage form.

In an aspect, the prostate cancer is metastatic prostate cancer, advanced prostate cancer, regional prostate cancer, locally advanced prostate cancer, localized prostate cancer, non-metastatic prostate cancer, non-metastatic advanced prostate cancer, non-metastatic regional prostate cancer, non-metastatic locally advanced prostate cancer, non-metastatic localized prostate cancer, hormone-naïve prostate cancer, chemotherapy-naïve prostate cancer, castration-naïve cancer with or without metastases, radiation-naïve prostate cancer, castration-resistant prostate cancer (CRPC), non-metastatic CRPC (nmCRPC), localized CRPC, locally advanced CRPC, regional CRPC, advanced CRPC, metastatic CRPC (mCRPC), mCRPC in patients having biallelic DNA-repair gene defect (DRD) or HRD; mCRPC in patients having monoallelic DRD or HRD; mCRPC in patients having no DRD or HRD; mCRPC in patients having DRD or HRD and having received taxane and/or androgen receptor-targeted therapy, mCRPC in patients having received docetaxel or cabazitaxel; CRPC in patients having received hormone therapy (for example enzalutamide, darolutamide, apalutamide), CRPC in patients having received taxane therapy (for example docetaxel, mitoxantrone, cabazitaxel), chemotherapy-naïve CRPC, chemotherapy-naïve mCRPC, hormone-naïve CRPC, hormone-naïve mCRPC, CRPC with progression, CRPC with visceral metastases, CRPC with visceral metastases in patients having received hormone therapy (for example enzalutamide, darolutamide, apalutamide), CRPC with visceral metastases in patients having received taxane therapy (for example docetaxel, mitoxantrone, cabazitaxel), CRPC with visceral metastases and progression, castration-sensitive prostate cancer (CSPC), non-metastatic CSPC (nmCSPC), localized CSPC, locally advanced CSPC, regional CSPC, advanced CSPC, metastatic CSPC (mCSPC), chemotherapy-naïve CSPC, chemotherapy-naïve mCSPC, hormone-naïve CSPC, hormone-naïve mCSPC, hormone-sensitive prostate cancer (HSPC), hormone-dependent prostate cancer, androgen-dependent prostate cancer, androgen-sensitive prostate cancer, biochemically relapsed HSPC, metastatic HSPC (mHSPC), hormone-resistant prostate cancer (HRPC), non-metastatic HRPC (nmHRPC), localized HRPC, locally advanced HRPC, regional HRPC, advanced HRPC, metastatic HRPC (mHRPC), recurrent prostate cancer, prostate cancer with prostate specific antigen (PSA) persistence or recurrence after prostatectomy with or without distant metastases, radiation-resistant prostate cancer, and any combination thereof. In an aspect, the patient has first-line (L1) mCRPC and is positive for DRD or HRD. In an aspect, the patient has deleterious germline or somatic homologous recombination repair (HRR) gene-mutated mCSPC. In an aspect, the patient has mCRPC or CRPC with visceral metastases, with or without DNA-repair gene defects (DRD), and optionally with cyclin dependent kinase 12 (CDK12) pathogenic alterations. In an aspect, the patient has high-risk localized prostate cancer.

In an aspect, the patient is in a risk group selected from very low, low, intermediate favorable, intermediate unfavorable, high, very high, and regional. In an aspect, the medical use or method of treatment comprises administering about 666 to about 1500 mg/day of abiraterone acetate; administering about 999 to about 1500 mg/day of abiraterone acetate; administering about 666 mg/day of abiraterone acetate; or administering about 1000 mg/day of abiraterone acetate. In an aspect, the medical use or method of treatment comprises administering about 33 to about 300 mg/day of niraparib eq.; administering about 100 to about 200 mg/day of niraparib eq.; administering about 66 mg/day of niraparib eq.; administering about 100 mg/day of niraparib eq.; administering about 134 mg/day of niraparib eq.; or administering about 200 mg/day eq. of niraparib. In an aspect, the medical use or method of treatment comprises administering 1, 2, or 3 oral dosage forms per day. In an aspect, the medical use or method of treatment comprises administering the oral dosage form(s) once a day (q.d.) or two times a day (b.i.d.); preferably once a day at least 1 hour before a meal or at least two hours after a meal. In an aspect, the medical use or method of treatment comprises administering separately about 1 to about 60 mg/day of prednisone; about 5 to about 15 mg/day of prednisone; about 9 to about 11 mg/day of prednisone; about 10 mg/day of prednisone; about 5 mg/day of prednisone; or about 5 mg/day of prednisone.

The present disclosure also relates to a process for preparing certain of the granule compositions disclosed herein, comprising the steps of:

(a) preparing a binder solution comprising a wetting agent;
(b) blending the binder solution of step (a) with abiraterone acetate, niraparib, and a diluent, optionally in the presence of a disintegrant;
(c) wet granulating the blend obtained from step (b);
(d) drying the product obtained from step (c).

In an aspect, the binder solution comprises a binder, the wetting agent and a solvent. In an aspect, the inlet air temperature during the wet granulating of step (c), is from 25° C. to 65° C. In an aspect, the spray rate during the wet granulating of step (c), is from 190 to 300 g/min. In an aspect, the inlet air flow during the wet granulating of step (c), is from 800 to 1300 $m^3/h$.

The present disclosure also relates to a process for preparing certain of the granule compositions disclosed herein, comprising the steps of:

(a) blending abiraterone acetate, niraparib, a wetting agent, and a diluent, optionally in the presence of a disintegrant and a lubricant;
(b) dry-granulating the blend obtained from step (a);
(c) milling the dry-granulated product obtained from step (b);
(d) optionally blending the product obtained from step (c), with a wetting agent, a diluent, a disintegrant, and a glidant.

The present disclosure also relates to a process for preparing certain of the granule compositions disclosed herein, comprising the steps of:

a) blending niraparib with a diluent, optionally in the presence of a disintegrant, a glidant, and a lubricant;
b) dry-granulating the blend obtained from step (a);
c) milling the dry-granulated blend obtained from step (b);
d) preparing a binder solution comprising a wetting agent;
e) blending the binder solution of step (d) with abiraterone acetate and a diluent, optionally in the presence of a disintegrant;
f) wet granulating the blend obtained from step (e);
g) drying the product obtained from step (f);
h) blending the granule blends obtained from steps (c) and (g), optionally in the presence of a wetting agent, a diluent, a disintegrant, a lubricant, and a glidant;

wherein steps d)-g) may be performed before, or in parallel, to steps a)-c).

In an aspect, the obtained granule composition is further compressed into a tablet optionally with a lubricant. In an aspect, the process further comprises preparing a coating suspension and coating the tablet with said suspension.

In an aspect, the obtained granule composition is further dosed into a capsule or sachet, optionally with a diluent.

FIGURES

FIG. 1: Flowchart of a manufacturing process and in-process controls for wet co-granulation of abiraterone acetate and niraparib tosylate monohydrate.

Figure 2:
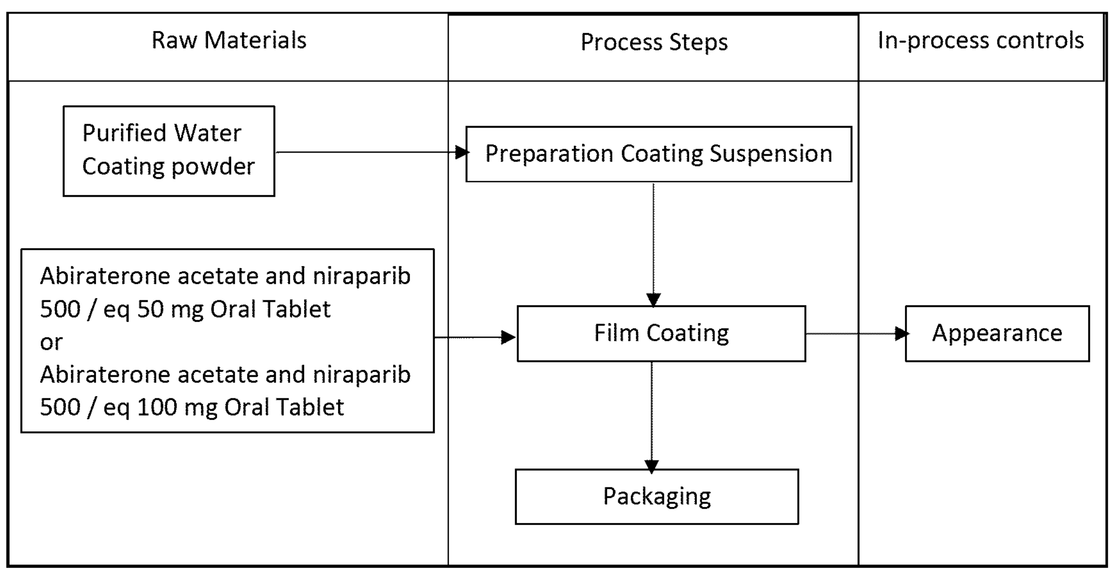

FIG. 2: Flowchart of a manufacturing process and in-process controls for coating tablets comprising abiraterone acetate and niraparib tosylate monohydrate.

Figure 3:
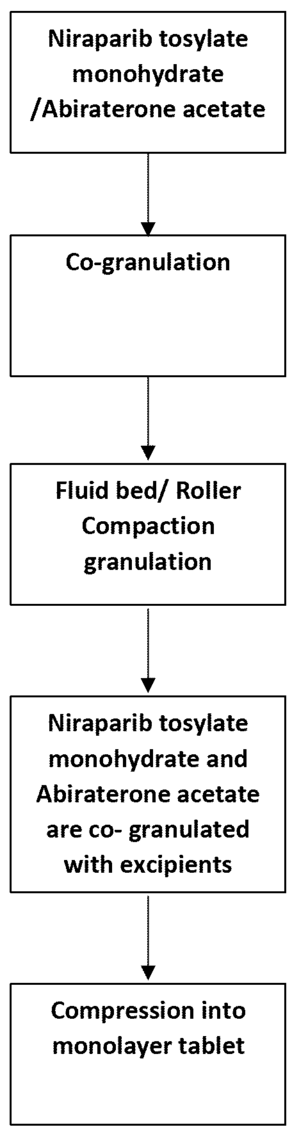

FIG. 3: Flowchart of a manufacturing process with dry co-granulation of abiraterone acetate and niraparib tosylate monohydrate and compression into tablets.

Figure 4:
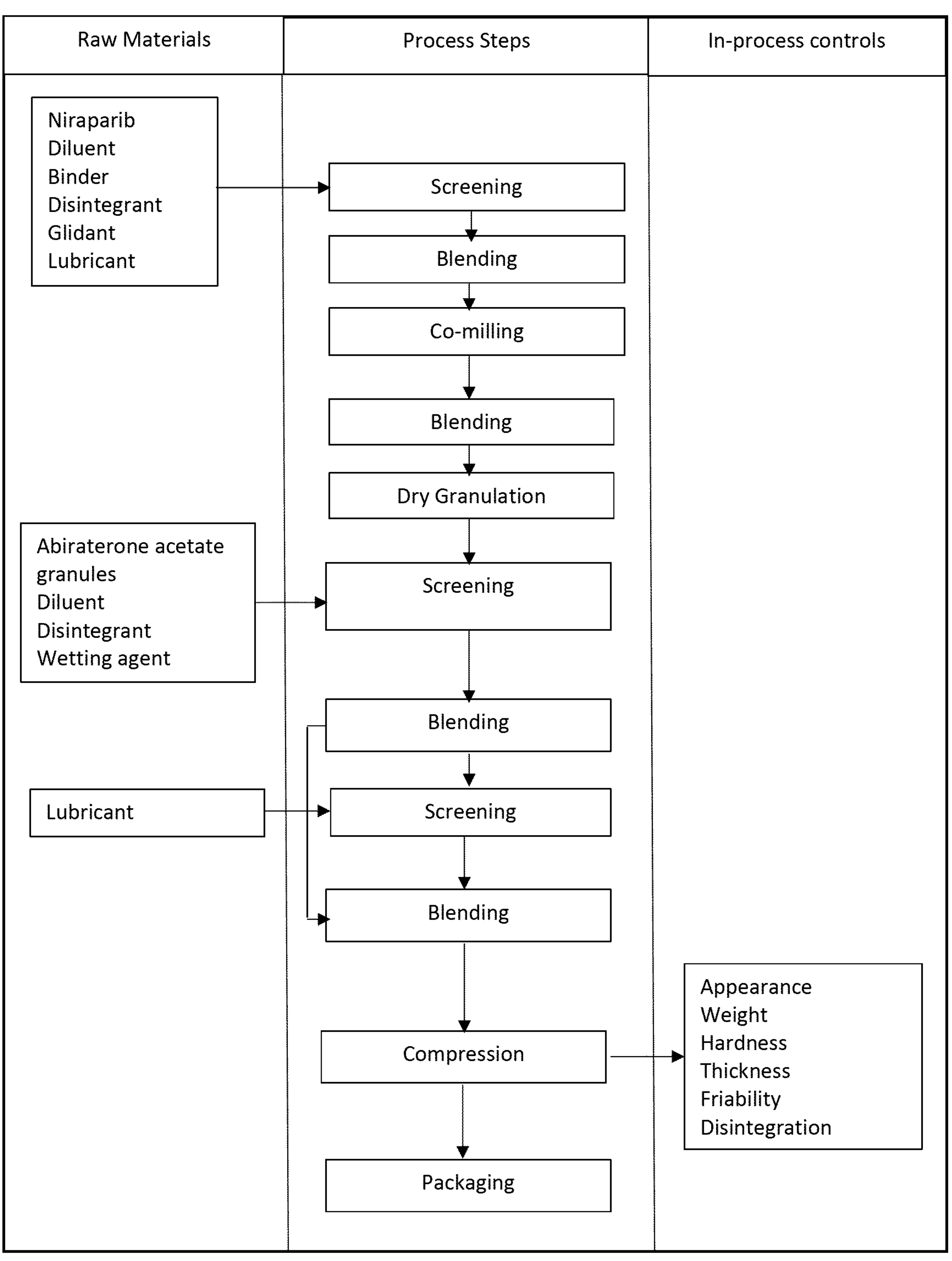

FIG. 4: Flowchart of a manufacturing process and in-process controls for dry granulation of niraparib tosylate monohydrate, and blending with granules of abiraterone acetate, the latter prepared by wet granulation.

Figure 5A:
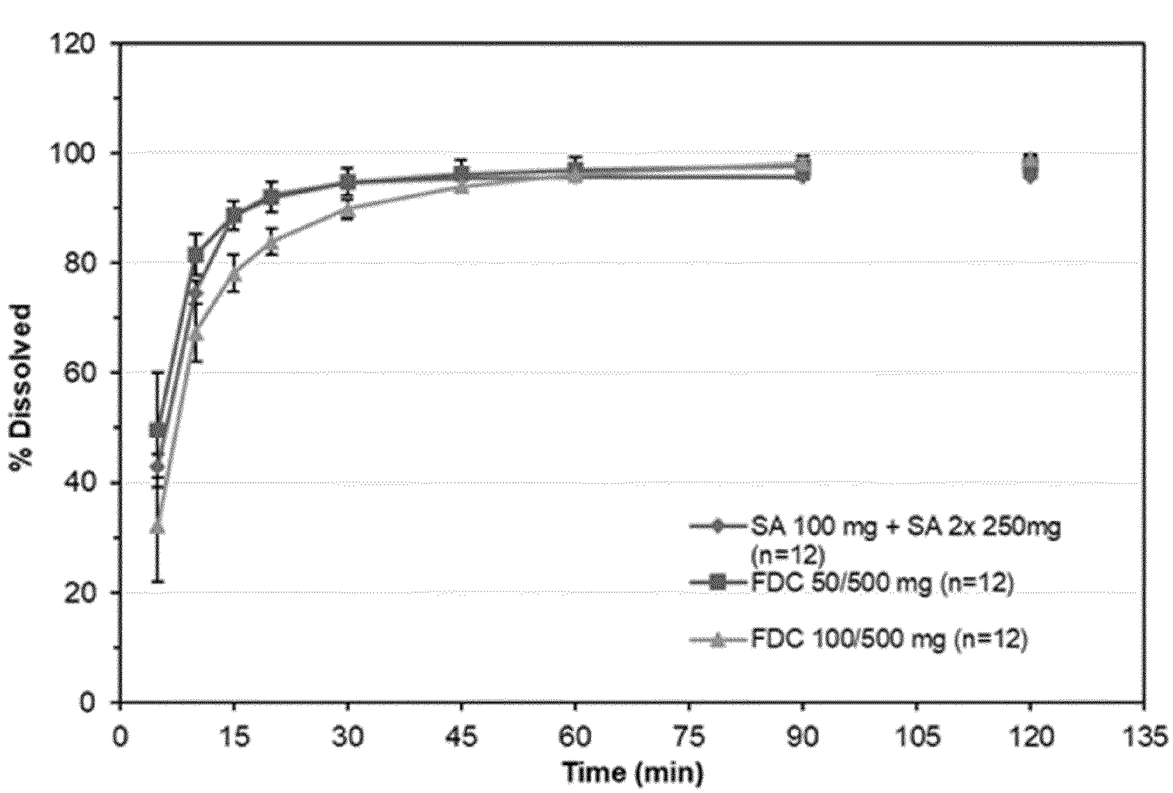

FIG. 5A: In vitro dissolution curves of abiraterone acetate from i) a combination of single agents being one capsule of 100-mg eq. niraparib, in tosylate monohydrate form, and 2 tablets of 250-mg abiraterone acetate; ii) a FDC tablet with the composition of Table 2 (50-mg eq. niraparib, in its tosylate monohydrate form, and 500-mg abiraterone acetate; and a iii) a FDC tablet with the composition of Table 4 (100-mg eq. niraparib, in its tosylate monohydrate form, and 500-mg abiraterone acetate).

Figure 5B:
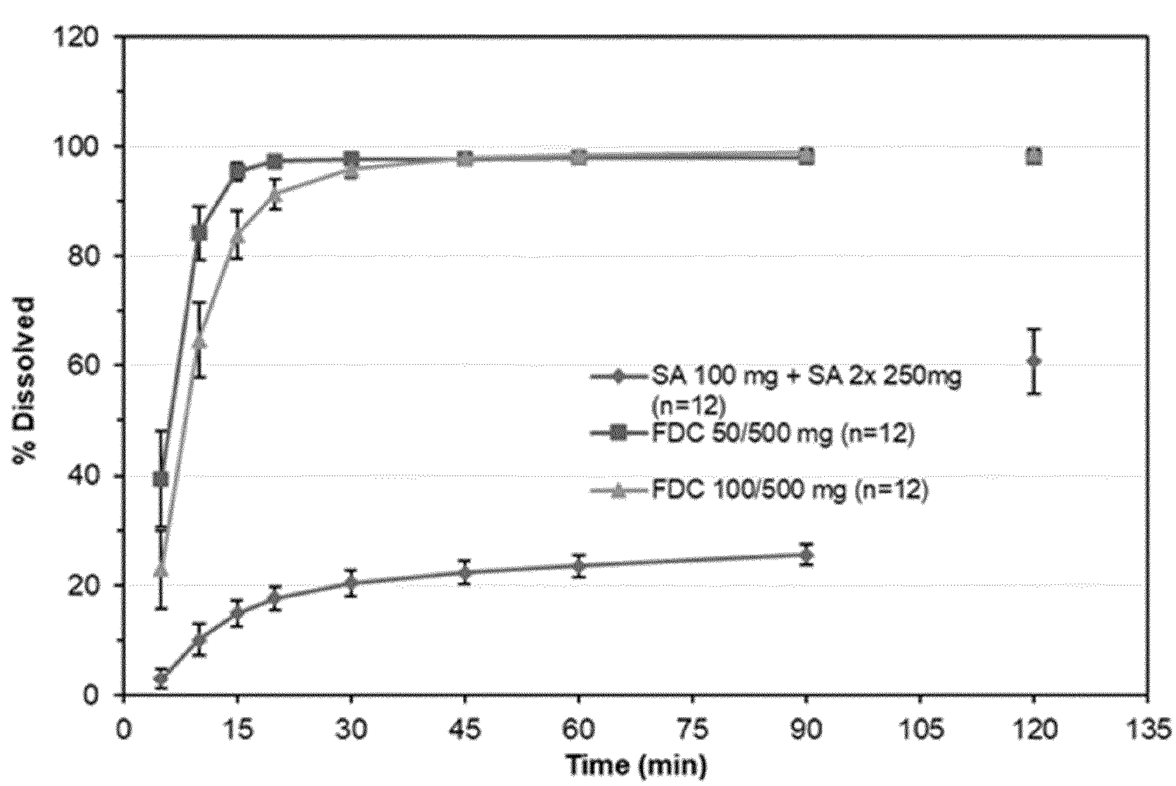

FIG. 5B: In vitro dissolution curves of niraparib from i) a combination of single agents being one capsule of 100-mg eq. niraparib, in its tosylate monohydrate form, and 2 tablets of 250-mg abiraterone acetate; ii) a FDC tablet with the composition of Table 2 (50-mg eq. niraparib, in its tosylate monohydrate form, and 500-mg abiraterone acetate); and iii) a FDC tablet with the composition of Table 4 (100-mg eq. niraparib, in its tosylate monohydrate form, and 500-mg abiraterone acetate).

Figure 6:
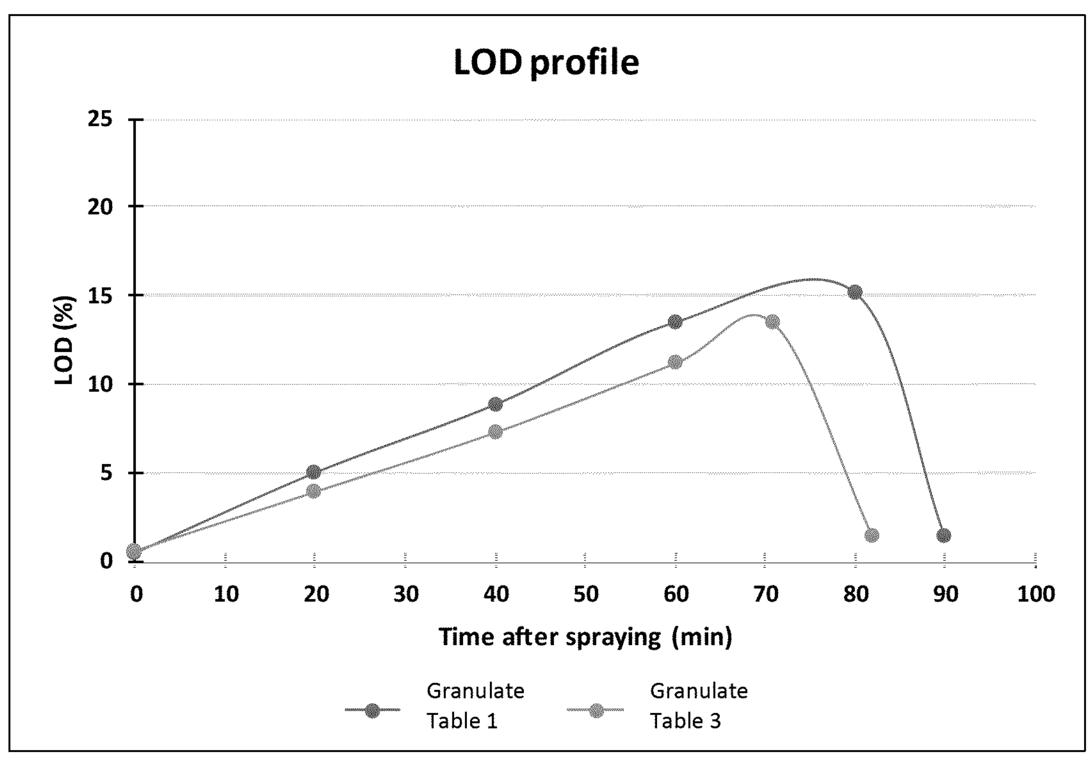

FIG. 6: Loss-on-drying (LOD) profiles for the granulates of the compositions of Table 1 and Table 3.

Figure 7:
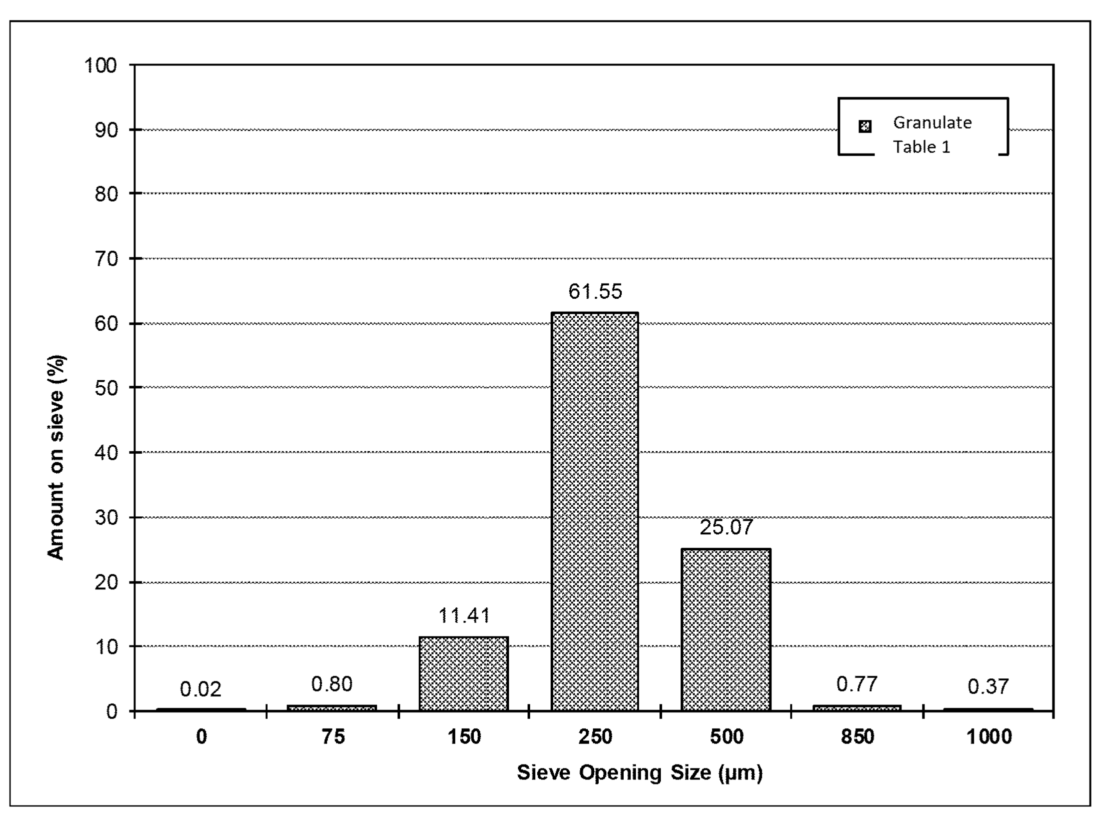

FIG. 7: Sieve analysis of the granulate of Table 1.

Figure 8:
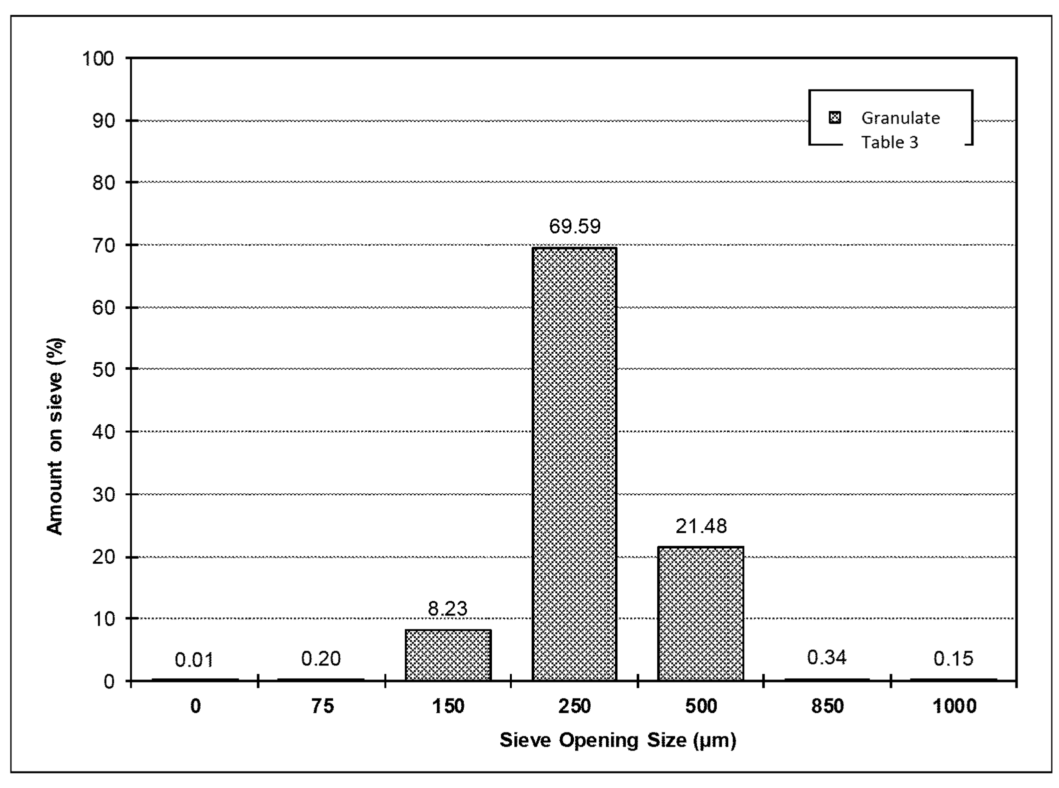

FIG. 8: Sieve analysis of the granulate of Table 3.

DETAILED DESCRIPTION

The present inventions may be understood more readily by reference to the following detailed description, taken in connection with the accompanying examples, which form a part of this disclosure. It is to be understood that these inventions are not limited to the specific products, methods, conditions or parameters described and/or shown herein, and that the terminology used herein is for the purpose of describing particular embodiments by way of example only and is not intended to be limiting of the claimed inventions.

The entire disclosures of each patent, patent application, and publication cited or described in this document are hereby incorporated herein by reference.

Definitions

As employed above and throughout the disclosure, the following terms and abbreviations, unless otherwise indicated, shall be understood to have the following meanings.

In the present disclosure the singular forms "a,", "an," and "the" include the plural reference, and reference to a given numerical value includes at least that value, unless the context clearly indicates otherwise. Thus, for example, a reference to "an ingredient" is a reference to one or more of such ingredients and equivalents thereof known to those skilled in the art, and so forth. Furthermore, when indicating that a certain element "may be" X, Y, or Z, it is not intended by such usage to exclude in all instances other choices for the element.

When values are expressed as approximations, by use of the antecedent "about," it will be understood that the particular value forms another embodiment. As used herein, "about X" (where X is a numerical value) preferably refers to ±10% of the recited value, inclusive. For example, the phrase "about 8" refers to a value of 7.2 to 8.8, inclusive; as another example, the phrase "about 8%" refers to a value of 7.2% to 8.8%, inclusive. Where present, all ranges are inclusive and combinable. For example, when a range of "1 to 5" is recited, the recited range should be construed as including ranges "1 to 4", "1 to 3", "1-2", "1-2 & 4-5", "1-3 & 5", and the like. In addition, when a list of alternatives is positively provided, such a listing can also include embodiments where any of the alternatives may be excluded. For example, when a range of "1 to 5" is described, such a description can support situations whereby any of 1, 2, 3, 4, or 5 are excluded; thus, a recitation of "1 to 5" may support "1 and 3-5, but not 2", or simply "wherein 2 is not included."

The term "immediate release" when used in the context of dosage forms (such as pharmaceutical formulations, free-dose combinations, fixed-dose combinations, granules, tablets, capsules, and the like), refers to the rapid disintegration and dissolution of said dosage forms to release the active pharmaceutical ingredients comprised in said dosage forms. The immediate release dosage forms dissolve or disintegrate in the stomach within a short period of time, and provide rapid dissolution and absorption of the active pharmaceutical ingredients, which may produce rapid onset of action.

As used herein, and unless otherwise defined, the terms "treat," "treating" and "treatment" include the eradication, removal, modification, management or control of a tumor or primary, regional, or metastatic cancer cells or tissue, in particular prostate cancer cells or tissue, and the minimization or delay of the spread of cancer, in particular prostate cancer. The minimization or delay of the spread of cancer includes inhibition of the progress of cancer, a reduction in the rate of progress of cancer, or a halt in the rate of progress of cancer.

As used herein, and unless otherwise defined, the phrase "therapeutically effective amount" or "effective amount" means an amount of the therapeutic agent effective for treating a prostate cancer.

As used herein, and unless otherwise defined, the phrase "safe therapeutic" means an amount of the therapeutic agent that is safe for treating a prostate cancer.

The term "pharmaceutically acceptable" means that which is generally safe, non-toxic and neither biologically nor otherwise undesirable and includes that which are acceptable for human pharmaceutical use as well as veterinary use.

The terms "formulation" and "composition" may be used interchangeably in the present disclosure. Both "formulation" and "composition" refer to at least combining two or more components, either as fixed-dose combinations or as free-dose combinations. As such the term "a pharmaceutical formulation" refers to fixed-dose combinations and free-dose combinations. The two or more components encompass herein at least 1) abiraterone acetate; and 2) niraparib, and any pharmaceutically acceptable salt, solvate, and hydrate forms thereof, for example niraparib tosylate monohydrate. The additional components are usually excipients.

As used herein, a "fixed-dose combination" (FDC) are formulations or compositions that include two or more active ingredients combined in a single dosage form. Herein, the two active ingredients are 1) abiraterone acetate; and 2) niraparib, and any pharmaceutically acceptable salt, solvate, and hydrate forms thereof, for example niraparib tosylate monohydrate.

In contrast, a "free-dose combination" (FrDC) are formulations or compositions that include two or more active ingredients combined in separate dosage forms. Herein, the two active ingredients are 1) abiraterone acetate; and 2) niraparib, and any pharmaceutically acceptable salt, solvate, and hydrate forms thereof, for example niraparib tosylate monohydrate.

The terms "excipient" and carrier" are used interchangeably in the present disclosure. The European Pharmacopoeia (Ph. Eur.) defines an excipient as "any component, other than the active substance(s), present in a medicinal product or used in the manufacture of the product. The intended function of an excipient is to act as the carrier (vehicle or basis) or as a component of the carrier of the active substance(s) and, in so doing, to contribute to product attributes such as stability, biopharmaceutical profile, appearance and patient acceptability and to the ease with which the product can be manufactured. Usually, more than one excipient is used in the formulation of a medicinal product." The terms vehicle and basis are further defined in the same pharmacopoeia: "A vehicle is the carrier, composed of one or more excipients, for the active substance(s) in a liquid preparation" and "A basis is the carrier, composed of one or more excipients, for the active substance(s) in semi-solid and solid preparations."

"Granules", "granulate", or "granulated particles" are defined herein as particles containing one or more active pharmaceutical ingredients (API) and at least one pharmaceutically acceptable carrier, that are formed by granulation. A granule composition according to the present disclosure comprises two APIs and at least one pharmaceutically acceptable carrier. A portion of the granule composition, i.e., a first portion of granules, may consist essentially of one API and at least one pharmaceutically acceptable carrier, and another portion of the granule composition, i.e., a second portion of granules, may consist essentially of another API and at least one pharmaceutically acceptable carrier. In another aspect, each and all of the portions of the granule composition, i.e. each and all of the granules, comprise two APIs and at least one pharmaceutically acceptable carrier.

Abiraterone Acetate

Abiraterone acetate is a compound of formula:

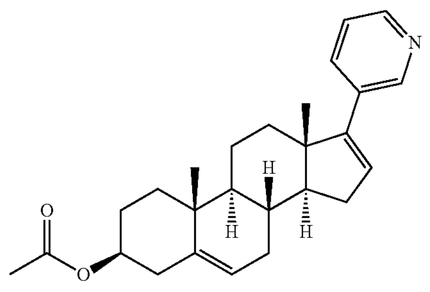

and is a prodrug of abiraterone, which is a potent selective, orally active inhibitor of the key enzyme in testosterone synthesis, 17α-hydroxylase-C17,20-lyase, also known as steroid 17α-monooxygenase inhibitor or Human Cytochrome P45017α. Suppression of testosterone synthesis has been demonstrated with abiraterone acetate in patients with prostate cancer. The compound was disclosed in WO 93/20097 (A1). In some aspects, abiraterone acetate is used herein in crystalline form.

Abiraterone acetate plus prednisone is approved for use in metastatic castration-resistant prostate cancer (mCRPC) and metastatic hormone-sensitive prostate cancer (mHSPC). Abiraterone acetate tablets are currently on the market as 250 or 500 mg oral tablets.

Niraparib

Niraparib, or 2-[4-[(3S)-piperidin-3-yl]phenyl]-2H-indazole-7-carboxamide, is an orally available highly selective poly(adenosine diphosphate [ADP]-ribose) polymerase (PARP) inhibitor, with activity against PARP-1 and PARP-2 deoxyribonucleic acid (DNA)-repair polymerases. The preparation of niraparib is described in U.S. Pat. Nos. 8,071,623 and 8,436,185, both of which are incorporated herein by reference.

The currently marketed capsule formulation (ZEJULA) contains 159.4 mg niraparib tosylate monohydrate (equivalent (eq.) to 100 mg niraparib free base) as the active ingredient. The inactive ingredients in the capsule fill include magnesium stearate and lactose monohydrate.

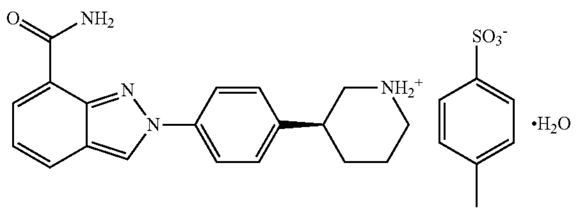

As used herein, the term "niraparib" means any of the free base compound (2-[4-[(3S)-piperidin-3-yl]phenyl]-2H-indazole-7-carboxamide), a salt form, including pharmaceutically acceptable salts, of 2-[4-[(3S)-piperidin-3-yl]phenyl]-2H-indazole-7-carboxamide (e.g., 4-methylbenzenesulfonic acid; 2-[4-[(3S)-piperidin-3-yl]phenyl]-2H-indazole-7-carboxamide), and/or a solvated form, including a hydrated form, thereof (e.g., 2-[4-[(3S)-piperidin-3-yl]phenyl]-2H-indazole-7-carboxamide tosylate monohydrate). Such forms may be individually referred to as "niraparib free base", "niraparib tosylate" and "niraparib tosylate monohydrate", respectively. Unless otherwise specified, the term "niraparib" includes all crystals, polymorphs, pseudopolymorphs, hydrates, monohydrates, anhydrous forms, solvates, salt forms, and combinations thereof, if applicable, of the compound 2-[4-[(3S)-piperidin yl]phenyl]-2H-indazole-7-carboxamide. Examples of salts include, without being limited to, tosylate or 4-methylbenzenesulfonate, sulfate, benzenesulfate, fumarate, succinate, camphorate, mandelate, camsylate, and lauryl sulfate. In a particular aspect, the term "niraparib" refers to niraparib tosylate monohydrate.

The term "niraparib" also encompasses the amorphous and the crystal polymorphs of this compound, and the hydrates, ansolvates, and solvates thereof. Examples of polymorphs are described in WO 2018/183354 A1, which is incorporated herein by reference. Crystal Form I of 2-[4-[(3S)-piperidin-3-yl]phenyl]-2H-indazole-7-carboxamide tosylate monohydrate is characterized by at least one X-ray diffraction pattern reflection selected from a 20 value of 9.5±0.2, 12.4±0.2, 13.2±0.2, 17.4±0.2, 18.4±0.2, 21.0±0.2, 24.9±0.2, 25.6±0.2, 26.0±0.2, and 26.9±0.2. Crystal Form II of 2-[4-[(3S)-piperidin-3-yl]phenyl]-2H-indazole-7-carboxamide tosylate non-stoichiometric hydrate is characterized by at least one X-ray diffraction pattern reflection selected from a 20 value of 9.7±0.3, 12.8±0.3, 17.9±0.3, 19.7±0.3, and 21.8±0.3. Crystal Form III of 2-[4-[(3S)-piperidin-3-yl]phenyl]-2H-indazole-7-carboxamide tosylate anhydrous form is characterized by at least one X-ray diffraction pattern reflection selected from a 2θ value of 17.8±0.2, 19.0±0.2, or 22.8±0.2. Crystal Form I is preferred. More examples of polymorphs are described in WO 2020/072797 A1, which is incorporated herein by reference.

The term "niraparib eq." or "niraparib equivalent" refers to the free base dose amount of niraparib.

Preparation of Dosage Forms

The dosage forms of the present disclosure may be prepared according to the scheme of FIGS. 1 and 2. A binder solution comprising purified water, binder (for example hypromellose), and a wetting agent (for example sodium lauryl sulfate) is prepared by mixing with a stirrer/mixer. Abiraterone acetate, niraparib tosylate monohydrate, diluent (for example lactose monohydrate), and disintegrant (for example crospovidone) are screened, blended (blend nr. 1), and added to the binder solution. Wet granulation, including warming, spraying and drying, is performed. Moisture content and particle size distribution are measured for compliance with quality requirements. Following, a mixture of diluent (for example silicified microcrystalline cellulose), disintegrant (for example crospovidone), wetting agent (for example sodium lauryl sulfate), and glidant (for example colloidal anhydrous silica) are screened and blended with the previously obtained granulated material (blend nr. 2). Lubricant (for example magnesium stearate) is screened and added to blend nr. 2, which is finally blended (blend nr. 3), compressed into tablets, and packaged. During compression, the appearance, weight, hardness, thickness, friability, and disintegration of the tablets are measured for compliance with quality requirements.

Following, a coating suspension comprising purified water and a coating powder (for example Opadry® AMB II, for example Opadry® AMB II 88A220039 yellow) is prepared. The previously obtained tablets comprising abiraterone acetate and niraparib tosylate monohydrate are film coated with the coating suspension. Appearance of the obtained coated tablets is measured for compliance with quality requirements. Tablets are then packaged, e.g., in blister packs or bottles.

In another aspect, the dosage forms of the present disclosure may be prepared as depicted in FIG. 3 and FIG. 2. Abiraterone acetate and niraparib tosylate monohydrate are co-granulated with suitable excipients by means of fluid bed granulation or by means of roller compaction granulation. The granulated material is then compressed into monolayer tablets.

Following, a coating suspension comprising purified water and a coating powder (for example Opadry® AMB II, for example Opadry® AMB II 88A220039 yellow) is prepared. The previously obtained tablets comprising abiraterone acetate and niraparib tosylate monohydrate are film coated with the coating suspension. Appearance of the obtained coated tablets is measured for compliance with quality requirements. Tablets are then packaged, e.g., in blister packs or bottles.

Yet in another aspect, the dosage forms of the present disclosure may be prepared as depicted in FIG. 4 and FIG. 2. Niraparib tosylate monohydrate, a diluent (for example lactose monohydrate and microcrystalline cellulose), a binder (for example povidone K30), a disintegrant (for example crospovidone), a glidant (for example colloidal anhydrous silica), and a lubricant (for example magnesium stearate) are screened, blended, co-milled, blended again, and dry granulated (dry granule composition nr. 1). Abiraterone acetate, a diluent (for example lactose monohydrate), and a disintegrant (for example croscarmellose sodium) are mixed and optionally sieved. A binder solution comprising a binder (for example Hypromellose), a wetting agent (for example sodium lauryl sulfate) and purified water, is prepared and added to the mixture of abiraterone acetate, diluent and disintegrant. Abiraterone acetate granules are then formed by fluid bed granulation and subsequently dried (wet granule composition nr. 2). The wet granule composition nr. 2, a diluent (for example silicified microcrystalline cellulose), a disintegrant (for example crospovidone), a wetting agent (for example sodium lauryl sulfate), and a glidant (colloidal anhydrous silica) is added to the dry granule composition nr. 1, and the resulting mixture is screened and blended. Lubricant (for example magnesium stearate) is added to the previous blend, and the resulting mixture is further screened, blended, compressed into tablets, and packaged. During compression, the properties of the tablets including appearance, weight, hardness, thickness, friability, and disintegration, are measured for compliance with quality requirements. Following, a coating suspension comprising purified water and a coating powder (for example Opadry® AMB II, for example Opadry® AMB II 88A220039 yellow) is prepared. The previously obtained tablets comprising abiraterone acetate and niraparib tosylate monohydrate are film coated with the coating suspension. Appearance of the obtained coated tablets is measured for compliance with quality requirements. Tablets are then packaged, e.g., in blister packs or bottles.

Granulation

Granulation is a process of enlargement of powdered particles to form grain-like agglomerates. The granules formed from the particles of the active pharmaceutical ingredient(s) (API(s)) and excipient mix are further processed effectively into solid dosage forms, such as tablets and capsules, or multiparticulates, such as pellets, beads, or spheroids to be filled into capsules or packed as sprinkle formulations, for example.

Abiraterone acetate and niraparib may be co-granulated. Alternatively, granules of each of 1) abiraterone acetate, and 2) niraparib, may be prepared separately and later mixed or blended, and further processed.

Co-granulation is practically achieved by bringing the two drugs into contact with each other, and with one or more excipients like a binder solution, and subjecting the entire mix to granulation. Alternatively, each of the drugs is brought into contact with one or more excipients creating separate mixes, each of the mixes is then brought together and put into contact with a binder solution.

Abiraterone acetate and niraparib may be dry-granulated or wet-granulated before further processing, like tableting or encapsulating.

In an aspect, abiraterone acetate and niraparib may be co-granulated by wet granulation and further processed. In an aspect, abiraterone acetate and niraparib may be co-granulated by dry granulation and further processed. In an aspect, abiraterone acetate is wet granulated and niraparib is dry granulated and the resulting granules blended and further processed. In an aspect, abiraterone acetate is dry granulated and niraparib is wet granulated and the resulting granules blended and further processed.

Wet Granulation

As used herein, the term "wet granulation" refers to the general process of using a granulation liquid in the granulation process to subsequently form granules, as discussed in Remington: The Science and Practice of Pharmacy, 20th Edition (2000), Chapter 45, which is hereby incorporated by reference.

Wet granulation usually includes the steps of mixing; wetting and kneading, i.e., wet massing; granulating; drying; and sieving. These steps are discussed in more detail below.

The wet granulation process begins with the formation of a powder blend of the therapeutic compound or compounds and at least one pharmaceutically acceptable excipient by mixing with, e.g., pharmaceutical granulation equipment, the ingredients (i.e., bringing into intimate proximity) in a suitable container, so as to form a mixture. Examples of pharmaceutical granulation equipment include but are not limited to, shear granulators (e.g., Hobart, Collette, Beken) in combination with an oscillating granulator; high-speed mixers/granulators (e.g., Diosna, Fielder, Collette-Gral); and fluidized-bed granulators (e.g., Aeromatic, Glatt) with a subsequent sieving equipment. Excipients useful for initially mixing with the therapeutic compound include, e.g., binders, fillers, disintegrants, diluents, wetting agents and any combinations of the foregoing.

The next step is wet massing the powder blend by adding a granulation liquid while agitating or kneading the powder blend until the powder blend is wetted with the granulation liquid to form a wet mass. For example, 10-30% (w/w) granulation liquid is added to the powder blend. Alternatively, 10-25% (w/w), e.g., 20-25%, granulation liquid can be added to the powder blend. The granulation liquid, for example, is pharmaceutically acceptable and volatile. Examples of suitable granulation liquids include, but are not limited to, water, organic solvents (e.g., methanol, ethanol, isopropanol, acetone) either alone or in combination. An example of a combination granulation liquid includes water, ethanol and isopropanol together.

Alternatively, the wet granulation process may begin with the therapeutic compound or compounds as a powder by itself. During wet massing, the granulation liquid that is introduced to the powder is a solvent containing a dissolved excipient, e.g., a binder. Irrespective of how wet-massing takes place, a pharmaceutical composition containing the therapeutic compound and at least one pharmaceutically acceptable excipient is wetted by the granulation liquid. In one example, water is used as the granulation liquid.

The wet mass is optionally sieved forming moist, or damp, granulates. The wet mass, e.g., can be sieved through a mesh, such as a 5, 4, 3, 2, or 1 mm screens, preferably from 1 to 2 mm screen. One of ordinary skill in the art can select the appropriate size of the screen to form the most appropriate granulate size.

Alternatively, a comminuting mill can be used in lieu of the screen or sieve. Examples of a comminuting mill include, but are not limited to, a Stokes oscillator, a Colton rotary granulator, a Fitzpatrick comminuting mill, a Stokes tornado mill.

Also, alternatively, a high-speed mixer equipped with, e.g., a chopper blade, can be used to replace either the screen or the comminuting mill. This, e.g., allows the wet massing, granulating, and the milling to be combined into a single step.

Other wet granulation methods that can be employed include high-shear granulation and twin-screw granulation. High-shear granulation involves adding a binder solution to a powder, which is often a mixture of API(s) and one or more excipients, and granulating the resulting mixture with blending tools and a chopper. The powder agglomerates into larger granules, held together by the binder. Twin screw granulation may be accomplished with twin-screw extruders available in the market such as those manufactured by Leistritz Extrusionstechnik GmbH—NANO 16, Thermo Fisher Scientific—Pharma 16 TSG). The ConsiGma™ system from GEA Pharma Systems is a complete continuous package comprising some or all of blending, twin-screw granulation, drying (semi-continuous), milling and tableting.

The moist granulates, for example, are subsequently dried. For example, the moist granulates can be collected on trays and transferred to a drying oven. Alternatively, the moist granulates can be placed in a drying cabinet with circulating air current and thermostatic heat control. Yet another option is to dry the moist granulates in a fluidized-bed drier. In this example, the moist granulates are suspended and agitated in a warm air stream such that the moist granulates are maintained in motion. For example, the temperature can be from about room temperature to about 90° C., e.g., 70° C. The moist granulates are dried to a loss on drying ("LOD") value preferably less than or equal to about 3% or 2%, e.g., less than 2.6%, less than 2%, e.g., 1-2%, by weight of the composition. Drying can take place within or apart from the pharmaceutical granulation equipment.

The granules comprising abiraterone acetate and niraparib tosylate monohydrate, prepared by the wet granulation of the present invention, achieve an improved LOD between 1 and 2%. If the LOD would be too low, the granules could result later in compression problems during tableting. If too high, the granules could have stability issues.

Subsequent to drying, the granulates can be further sieved, i.e., dry screened, alone or in combination with at least one excipient. This typically results in a more uniform particle size of the granulate, preparing the granulates for further processing into a solid oral dosage form. Standard equipment like Quadro comil may be used at a fixed rotational speed (rpm) to screen the dried granules to produce material with desired particle size and free from agglomerates. The rotational speed may be from 5 to 15 rpm, preferably from 8 to 10 rpm.

In one way of preparation by wet granulation, for instance by fluid bed granulation, a binder solution is created by dissolving a binder, wetting agent, and purified water until a clear solution is obtained. The therapeutic compounds, optionally mixed with a diluent and disintegrant are transferred into a suitable wet granulation equipment, and the resulting mass is warmed up while fluidizing. The binder solution is sprayed completely upon the mass using the wet granulation technique. The resulting granulate is dried after spraying while fluidizing. The dried powder is collected and packed in bags, for instance aluminum bags.

In another way of preparation, the therapeutic compound (s) may be wet-granulated in a fluid bed granulator, such as for example, a GEA Sirocco 300 or a Niro Aeromatic D600, resulting in the drug granulates. The inlet air temperature of the fluid bed may vary from 25° C. to 80° C. or from 25° C. to 70° C., preferably from 25° C. to 65° C.; the outlet air temperature may vary from 25° C. to 50° C., from 20° C. to 50° C., or from 25° C. to 80° C.; the inlet air flow may range from 500 to 2200 $m^3$/h, from 2000 to 3000 $m^3$/h, from 800 to 1300 $m^3$/h, or from 500 to 4500 $m^3$/h; the solution flow rate or spray rate may range depending on the batch size and equipment capacity from 170 to 4200 g/min, from 190 to 300 g/min, from 400 to 900 g/min, or between 0.200 to 2 kg/min; the atomizing air pressure may range from 2-6 bar, from 3 to 4 bar, or from 1.00 to 5.00 bar. In an example, the abiraterone acetate and niraparib or niraparib tosylate monohydrate may be wet-granulated with a binder solution comprising a solvent, such as for example, water, a binder, such as for example, a polymer, e.g., hypromellose, and a wetting agent, such as for example, sodium lauryl sulfate. In an example, prior to being granulated with a binder solution, the abiraterone acetate may be mixed with a suitable diluent, such as for example, lactose monohydrate, and a suitable disintegrant, such as for example, crospovidone.

Dry Granulation

The term "dry granulation" means the process of blending therapeutic compound(s) with at least one excipient. The blend is then compressed, or compacted, to form a compressed material or "compact". This material is then broken apart by crushing, grinding or cutting into dry granulated particles. Optionally, the particles may be further processed, like further mixing with additional excipients. Crushing, grinding, or cutting processes involve an operation that reduces the size of the compressed material such as accomplished by milling or by other operations known to those skilled in the art.

A "compact" is a compressed material formed by processing the therapeutic compound or compounds and optional excipients by slugging or by roller compaction.

For preparing the blend, the components are weighed and placed into a blending container. Blending is performed for a period of time to produce a homogenous blend using suitable mixing equipment. Optionally, the blend is passed through a mesh screen to de-lump the blend. The screened blend may be returned to the blending container and blended for an additional period of time. Lubricant may then be added, and the blend mixed for an additional period of time. The blend is then compressed, or compacted, to form a compact. Prior to compression, the blend may be subjected to a precompression step such as on a rotary tablet press. Compression of the blend to form granules may be accomplished by techniques known in the art including slugging where the blend is introduced into dies comprising one or more punch faces that are installed on a press such as a tablet press and pressure is applied to the blend by the movement of one or more punch faces in the die. Dry granulation may also be performed by means of a roller compactor. A roller compactor generally incorporates two or more rollers adjacent and parallel to each other with a fixed or adjustable gap between the rollers. A hopper or other feeding device deposits blend between the moving rollers which act to compact the blend into a compacted material. Roller compactors are typically equipped with dividers that cut or otherwise divide the compacted material emerging from the roller compactor into ribbons. An example of a roller compactor is TF-Mini Roller Compactor (Vector Corporation, Marion, IA, Freund).

The compact is then broken apart to form granules, typically by suitable mechanical means, such as by crushing, grinding or cutting. For example, granules may be formed from a compact by milling. Milling involves subjecting the granules to a shear force such that the desired particle size of the granulation is achieved. The milling step may range from an aggressive process where the particle size is reduced significantly to a non-aggressive process where the particle size is not reduced significantly, but merely done to de-lump or break up larger clumps of granulation.

In the pharmaceutical industry, milling is often used to reduce the particle size of solid materials. Many types of mills are available including pin mills, hammer mills and jet mills. One of the most commonly used types of mill is the hammer mill. The hammer mill utilizes a high-speed rotor to which a number of fixed or swinging hammers are attached.

The hammers can be attached such that either the knife face or the hammer face contacts the material. As material is fed into the mill, it impacts on the rotating hammers and breaks up into smaller particles. A screen is located below the hammers, which allows the smaller particles to pass through the openings in the screen. Larger particles are retained in the mill and continue to be broken up by the hammers until the particles are fine enough to flow through the screen. The material may optionally be screened. In screening, material is placed through a mesh screen or series of mesh screens to obtain the desired particle size.

Excipients

The formulations of the disclosure, including granules and final dosage forms like tablets, may comprise one or more conventional excipients (pharmaceutically acceptable carrier) such as disintegrants, diluents, binders, buffering agents, lubricants, glidants, thickening agents, sweetening agents, flavors, and colors. Some excipients can serve multiple purposes. In an aspect, the formulations of the present disclosure include a disintegrant, a diluent or filler, a lubricant and glidant. In an aspect, the formulations of the present disclosure include a disintegrant, a diluent or filler, a lubricant, glidant, a wetting agent and a binder. In an aspect, the formulations of the present disclosure include a disintegrant, a diluent or filler, a lubricant, glidant, a wetting agent and a binder, wherein the wetting agent or part of it, and the binder are present in granules of abiraterone acetate and niraparib. In an aspect, the formulations of the present disclosure include a disintegrant, a diluent or filler, a lubricant, glidant, a wetting agent and a binder, wherein the wetting agent or part of it, the binder, and the disintegrant or part of it, are present in granules of abiraterone acetate and niraparib. In an aspect, the formulations of the present disclosure include a disintegrant, a diluent or filler, a lubricant, glidant, a wetting agent and a binder, wherein the wetting agent or part of it, the binder, the diluent, and the disintegrant or part of it, are present in granules of abiraterone acetate and niraparib. In an aspect, the formulations of the present disclosure include a disintegrant, a diluent or filler, a lubricant, glidant, and a wetting agent, wherein the wetting agent or part of it is present in granules of abiraterone acetate and niraparib.

In an aspect, the formulations of the present disclosure comprise an intragranular phase and an extragranular phase.

In an aspect, the intragranular phase comprises the APIs, a diluent or filler, a disintegrant, a wetting agent, and a binder. In an aspect, the intragranular phase comprises the APIs, a diluent or filler, a disintegrant, a wetting agent, a glidant, and a lubricant.

In an aspect, the extragranular phase comprises a diluent or filler, a disintegrant, a wetting agent, a glidant, and a lubricant.

In an aspect, the intragranular and extragranular phases comprise a disintegrant, e.g., crospovidone. The presence of disintegrant both in the intragranular and extragranular phases improves disintegration of the tablet and the granules, thereby increasing dissolution of the APIs in the body, eventually increasing the bioavailability of the APIs.

Suitable wetting agents may be selected from anionic, cationic or non-ionic surface-active agents or surfactants. Suitable anionic surfactants include those containing carboxylate, sulfonate, and sulfate ions, such as sodium lauryl sulfate (SLS), sodium laurate, dialkyl sodium sulfosuccinates particularly bis-(2-ethylhexyl) sodium sulfosuccinate, sodium stearate, potassium stearate, sodium oleate and the like. Suitable cationic surfactants include those containing long chain cations, such as benzalkonium chloride, bis-2-hydroxyethyl oleyl amine or the like. Suitable non-ionic surfactants include polyoxyethylene sorbitan fatty acid esters, fatty alcohols such as lauryl, cetyl and stearyl alcohols; glyceryl esters such as the naturally occurring mono-, di-, and tri-glycerides; fatty acid esters of fatty alcohols and other alcohols such as propylene glycol, polyethylene glycol, sorbitan, sucrose, and cholesterol. In an aspect, the wetting agent is sodium lauryl sulfate.

The amount of wetting agent in the tablets or pharmaceutical formulations according to the present disclosure may conveniently range from about 0.5 to about 8% (w/w) and preferably range from about 1 to 7% (w/w) or from about 2 to 6% (w/w) or from about 3 to 6% (w/w). In an aspect, the wetting agent is sodium lauryl sulfate and is present in the final dosage forms in a percentage of about 3.1, about 3.2, about 3.3, about 3.4, about 3.5, about 3.6, about 3.7, about 3.8, about 3.85, about 3.9, about 4.00, about 4.07, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, or about 5.9% by weight.

In an aspect, the wetting agent is sodium lauryl sulfate and is present in the granule composition in a by weight ratio versus abiraterone acetate of about 0.005:1 to 0.02:1 (SLS: abiraterone acetate), preferably about 0.01:1, more preferably about 0.0112:1.

In an aspect, the wetting agent is sodium lauryl sulfate and is present in the final dosage forms in a by weight ratio versus abiraterone acetate of about 0.05:1 to 0.2:1 (SLS: abiraterone acetate), preferably about 0.1:1, more preferably about 0.11:1, about 0.12:1 or about 0.123:1.

Suitable disintegrants are those that have a large coefficient of expansion. Examples of pharmaceutically acceptable disintegrants include, but are not limited to, starches, clays, celluloses, alginates, gums, hydrophilic, insoluble or poorly water-soluble crosslinked polymers such as crospovidone (crosslinked polyvinylpyrrolidone, e.g., commercially available as Kollidon CL-F and Polyplasdone XL-10) and croscarmellose sodium (crosslinked sodium carboxymethylcellulose). The disintegrant may be present in the tablets or pharmaceutical formulations in an amount from about 1 to about 20% (w/w), preferably from about 2 to about 10% (w/w), in particular from about 3 to 9%, or from about 5 to 9% (w/w).

For the granule compositions of the present invention and the oral dosage forms comprising these granule compositions, excipients that can dissociate into ions are less preferred although an exception is made with sodium lauryl sulfate (wetting agent) and magnesium stearate (lubricant), in the formulations disclosed herein. In particular embodiments, the disintegrant is a non-ionizable disintegrant, such as crospovidone.

A variety of materials may be used as diluents or fillers. Examples are lactose monohydrate, anhydrous lactose, sucrose, dextrose, mannitol, sorbitol, starch, cellulose (e.g., microcrystalline cellulose (Avicel™), silicified microcrystalline cellulose), dihydrated or anhydrous dibasic calcium phosphate, and others known in the art, and mixtures thereof (e.g., spray-dried mixture of lactose monohydrate (75%) with microcrystalline cellulose (25%), which is commercially available as MicroceLac®). Preferred is microcrystalline cellulose, silicified microcrystalline cellulose, or lactose monohydrate. Lactose monohydrate is usually characterized as a diluent or filler but it has also binding properties that are particularly useful for the granulation of the intragranular phase. The amount of diluent or filler in the tablets or pharmaceutical formulations according to the present disclosure may conveniently range from about 20% to about 70% (w/w) and preferably ranges from about 20% to about 60% (w/w), or from about 25% to about 35% (w/w), or from about 25% to about 30% (w/w). Preferably the diluent silicified microcrystalline cellulose is used in the extra-granular phase. Preferably a tablet FDC comprises an extragranular phase containing from about 25% to about 30% (w/w) of silicified MCC HD90. This content of silicified MCC HD90 provides an optimal compression profile of the tablet, decreasing its friability and abrasion.

Examples of pharmaceutically acceptable binders include, but are not limited to, starches; celluloses and derivatives thereof, e.g., microcrystalline cellulose, e.g., AVICEL PH from FMC (Philadelphia, PA), hydroxypropyl cellulose, hydroxyethyl cellulose and hydroxylpropylmethyl cellulose, e.g., METHOCEL from Dow Chemical Corp. (Midland, MI); sucrose; dextrose; corn syrup; polysaccharides; and gelatin. The binder, e.g., may be present in an amount from about 0.5% to about 5%, e.g., 0.5 to 3% by weight of the formulation. Preferably the binder is hypromellose of low viscosity grade, e.g., HPMC 2910 15 mPa·s.

Lubricants and glidants can be employed in the manufacture of certain dosage forms and will usually be employed when producing tablets. Examples of lubricants and glidants are hydrogenated vegetable oils, e.g., hydrogenated cottonseed oil, magnesium stearate, stearic acid, sodium lauryl sulfate, magnesium lauryl sulfate, colloidal silica, colloidal anhydrous silica talc, mixtures thereof, and others known in the art. Interesting lubricants are magnesium stearate, and mixtures of magnesium stearate with colloidal anhydrous silica. A preferred lubricant is magnesium stearate. A preferred glidant is colloidal anhydrous silica. Glidants generally comprise 0.2 to 5.0% of the total weight of the composition, in particular the total tablet weight, in particular 0.25 to 1.5%, more in particular 0.3 to 1.0% (w/w). Lubricants, like magnesium stearate, generally comprise 0.2 to 5.0% of the total tablet weight, in particular 0.5 to 2.5%, more in particular 0.5 to 2.0%, for example about 1.0%, about 1.25%, or about 1.5% (w/w).

Final Pharmaceutical Formulations

The granulates may be formulated with excipients into oral dosage forms, solid oral dosage forms, tablets, pills, lozenges, caplets, hard or soft capsules, sachets, troches, aqueous or oily suspensions, dispersible powders or granules, granulates.

Compositions intended for oral use may be prepared according to any method known in the art for the manufacture of pharmaceutical compositions and such compositions may contain one or more agents selected from the group consisting of sweetening agents, flavoring agents, coloring agents and preserving agents in order to provide pharmaceutically elegant and palatable preparations.

Tablets contain the active ingredients in admixture with non-toxic pharmaceutically acceptable excipients which are suitable for the manufacture of tablets. These excipients may be, for example, inert diluents, such as calcium carbonate, sodium carbonate, lactose monohydrate, silicified microcrystalline cellulose, calcium phosphate or sodium phosphate; granulating and disintegrating agents, for example, crospovidone, microcrystalline cellulose, sodium croscarmellose, corn starch, or alginic acid; binding agents, for example, starch, gelatin, polyvinyl-pyrrolidone or acacia; lubricating agents, for example, magnesium stearate, stearic acid or talc; and glidants like colloidal anhydrous silica.

To make, e.g., a tablet, the granules are combined or blended with at least one excipient, e.g., a lubricant, to form a mixture. The blending can be accomplished using any conventional pharmaceutical equipment, e.g., a V-blender.

Furthermore, any additional excipients used can be sieved separately from the granules or concurrently with the sieving of the granules as described in the afore-mentioned dry sieving step. One of ordinary skill in the art will appreciate the necessary particle size of each component that is necessary for the particular pharmaceutical composition being formulated.

The blended mixture can, e.g., be subsequently compacted into a tablet (e.g., by using a tablet press) or encapsulated into a capsule. The tablet hardness is preferably in a range of 250 to 350 N. The solid oral dosage forms may be subject to further conventional processing as known to one of ordinary skill in the art, e.g., imprinting, embossing or coating.

The tablets may be uncoated or they may be coated by known techniques. Tablets of the present disclosure may further be film-coated e.g. to improve taste, to provide ease of swallowing and an elegant appearance. Many suitable polymeric film-coating materials are known in the art. In an aspect, the film-coating material is Opadry® AMB II 88A170010 beige, Opadry® AMB II 88A210027 green, Opadry® AMB II 88A620004 yellow, Opadry® AMB II 88A220039 yellow, Opadry® QX 321A220006 yellow, or Opadry® II 32F220009. The film-coating material is usually mixed with purified water Ph. Eur to form a coating suspension. Preferred coating suspensions are those in which the film-coating material is Opadry® AMB II 88A170010 beige, Opadry® AMB II 88A210027 green, and Opadry® AMB II 88A620004 yellow, because the resulting coated tablets show no scuffing. Other suitable film-forming polymers also may be used herein, including, hydroxypropylcellulose, hydroxypropyl methylcellulose (HPMC), especially HPMC 2910 5 mPa·s, and acrylate-methacrylate copolymers. A preferred film-coating material is a water permeable film-coating material, such as for example the HPMC coating Opadry II 32F220009. Besides a film-forming polymer, the film coat may further comprise a plasticizer (e.g., propylene glycol) and optionally a pigment (e.g., titanium dioxide). The film-coating suspension may also contain talc as an anti-adhesive. In tablets according to the present disclosure, the film coat in terms of weight preferably accounts for about 5% (w/w) or less of the total tablet weight.

In order to facilitate the swallowing of such a formulation by a mammal, it is advantageous to give the formulations, in particular tablets, an appropriate shape. A film coat on the tablet may further contribute to the ease with which it can be swallowed. In an aspect of the present disclosure the tablet may be an oblong shaped tablet, in particular an oblong shaped tablet with a length of ≤19 mm.

Other excipients such as coloring agents and pigments may also be added to the formulations of the present disclosure. Coloring agents and pigments include titanium dioxide and dyes suitable for food. A coloring agent is an optional ingredient in the formulation of the present disclosure, but when used the coloring agent can be present in an amount from about 1 to about 6% by weight based on the total tablet weight, for example from about 2 to about 5%, from about 3 to about 4%, or up to 3.5% by weight based on the total tablet weight.

Flavors are optional in the formulation and may be chosen from synthetic flavor oils and flavoring aromatics or natural oils, extracts from plants leaves, flowers, fruits and so forth and combinations thereof. These may include cinnamon oil, oil of wintergreen, peppermint oils, bay oil, anise oil,

*eucalyptus*, or thyme oil. Also useful as flavors are vanilla, citrus oil, including lemon, orange, grape, lime and grapefruit, and fruit essences, including apple, banana, pear, peach, strawberry, raspberry, cherry, plum, pineapple, apricot and so forth, The amount of flavor may depend on a number of factors including the organoleptic effect desired. Generally, the flavor will be present in an amount from about 0% to about 3% (w/w).

Formulations for oral use may also be presented as hard gelatin or HPMC capsules wherein the active ingredients are mixed with an inert solid diluent, for example, calcium carbonate, calcium phosphate or kaolin, or as soft gelatin capsules wherein the active ingredients are mixed with water soluble carrier or an oil medium, for example, peanut oil, liquid paraffin, or olive oil.

Aqueous suspensions contain the granules with the therapeutic compounds in admixture with excipients suitable for the manufacture of aqueous suspensions. Such excipients are suspending agents, for example, sodium carboxymethylcellulose, methylcellulose, hydroxypropylmethyl-cellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example, polyoxyethylene stearate, or condensation products of ethylene oxide with long chain aliphatic alcohols, for example, heptadecaethyleneoxycetanal, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example, polyethylene sorbitan monooleate. The aqueous suspensions may also contain one or more preservatives, for example, ethyl, or n-propyl p-hydroxybenzoate, one or more coloring agents, one or more flavoring agents, and one or more sweetening agents, such as sucrose, saccharin or aspartame.

Oily suspensions may be formulated by suspending the granules with the therapeutic compounds in a vegetable oil, for example, *arachis* oil, olive oil, sesame oil or coconut oil, or in mineral oil such as liquid paraffin. The oily suspensions may contain a thickening agent, for example, beeswax, hard paraffin or cetyl alcohol. Sweetening agents such as those set forth above, and flavoring agents may be added to provide a palatable oral preparation. These compositions may be preserved by the addition of an antioxidant such as butylated hydroxyanisol or alpha-tocopherol.

Dispersible powders and granules suitable for preparation of an aqueous suspension by the addition of water provide the active ingredients in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present. These compositions may be preserved by the addition of an antioxidant such as ascorbic acid.

At first instance, with the present disclosure pharmaceutical formulations for oral administration such as tablets and capsules are envisaged, but the pharmaceutical formulations of the present disclosure can also be used for rectal administration. Preferred formulations are those adapted for oral administration shaped as a tablet. They can be produced by conventional tableting techniques with conventional ingredients or excipients (pharmaceutically acceptable carrier) and with conventional tableting machines.

Methods of Treatment and Medical Uses

The methods for treating a prostate cancer, or the medical uses of the pharmaceutical formulations comprise, consist of and/or consist essentially of, administering to a patient in need thereof a therapeutically effective amount of the PARP inhibitor niraparib, a therapeutically effective amount of the CYP17 inhibitor abiraterone acetate, and optionally a therapeutically effective amount of another drug, for example a glucocorticoid, for example prednisone.

The methods for treating a prostate cancer, or the medical uses of the pharmaceutical formulations comprise, consist of and/or consist essentially of, administering to a patient in need thereof a free-dose combination (FrDC) or fixed-dose combination (FDC) of niraparib and abiraterone acetate. The methods for treating a prostate cancer, or the medical uses of the pharmaceutical formulations comprise, consist of and/or consist essentially of, administering to a patient in need thereof the afore-mentioned free-dose combination or fixed-dose combination, plus a glucocortidoid, for example prednisone.

The methods of treatment and medical uses disclosed herein comprise administering to a patient in need thereof, oral dosage forms as defined in the present disclosure, said oral dosage forms comprising a granule composition comprising abiraterone acetate, niraparib, and a pharmaceutically acceptable carrier. These oral dosage forms and granule compositions constitute the FDCs.

Also disclosed are dosage regimens of the oral dosage forms disclosed herein, said dosage regimens comprising, consisting of and/or consisting essentially of, administering the FDC of niraparib and abiraterone acetate, and optionally plus a glucocorticoid, for example prednisone, in a total amount that is therapeutically effective for the treatment of prostate cancer in a human patient.

The present disclosure also discloses kits comprising, consisting of, and/or consisting essentially of, a free-dose combination or a fixed-dose combination comprising niraparib and abiraterone acetate, and an instruction print for administering the free-dose combination or fixed-dose combination to a human patient having a prostate cancer.

The kits may comprise, consist, and/or consist essentially of, a free-dose combination or a fixed-dose combination comprising niraparib and abiraterone acetate, a separate composition that comprises a glucocorticoid, for example prednisone; and an instruction print for administering the free-dose combination or fixed-dose combination to a human patient having a prostate cancer.

Where a particular reference is made "prednisone" in the present disclosure, one of ordinary skill will recognize that prednisone may be substituted with a different glucocorticoid, such as prednisolone, hydrocortisone, methyl prednisolone, or dexamethasone. The person skilled in the art will know how to exchange prednisone with these other drugs and adjust their dosage, if necessary.

Particular suitable glucocorticoids include but are not limited to, (1) dexamethasone (e.g., Decadron, oral; Decadron-LA injection, etc.), (2) prednisolone (e.g., Delta-CORTEF®, prednisolone acetate (ECONOPRED®), prednisolone sodium phosphate (HYDELTRASOL®), prednisolone tebutate (HYDELTRA-TBA®, etc.)), (3) prednisone (DELTASONE®, etc.), or (4) methylprednisolone (e.g., MEDROL®), and combinations thereof. See, e g., Goodman & Gilman's The Pharmacological Basis of Therapeutics, 10th edition 2001.

The formulations described herein may be used in methods of treating prostate cancer patients with negative biomarker status. The formulations described herein may be used in methods of treating prostate cancer patients with positive biomarker status.

The formulations described herein may be used in methods of treating prostate cancer patients with homologous recombination deficiency (HRD) positive biomarker status. HRD is also referred to as homologous recombination repair (HRR) defects and can result from DNA repair gene defects (DRD). Said HRD—or HRR defects—positive status may be detected by evaluating somatic or germline alterations, or by evaluating genome-wide loss of heterozygosity (LOH), or homozygous deleterious changes in DNA repair genes. HRD—or HRR defects—positive status is also a synonym for PARP biomarker positive status.

The positive biomarker status may be HRD-positive status. The negative biomarker status may be HRD-negative status. HRD status may be evaluated by either a plasma- (Resolution Bioscience) or tissue-based test (Foundation Medicine), particularly by detecting circulating plasma DNA or circulating tumor cells. HRD positive status may be defined as having monoallelic or biallelic alterations in one or more DNA repair genes, including without being limited to, BRCA1 (Breast Cancer gene 1), BRCA2 (Breast Cancer gene 2), ATM (ataxia-telangiectasia mutated), FANCA (Fanconi Anemia Complementation Group A gene), PALB2 (Partner and Localizer of BRCA2 gene), CHEK2 (Checkpoint Kinase 2 gene), BRIP1 (BRCA1 Interacting Protein C-terminal Helicase 1 gene), HDAC2 (Histone deacetylase 2), CDK12 (Cyclin Dependent Kinase 12), RAD51B (RAD51paralog B), RAD54L (RAD54-Like), CDK17 (Cyclin Dependent Kinase 17), or PPP2R2A (protein phosphatase 2 regulatory subunit B alpha).

Gene expression profile analysis and protein biomarkers may also be used to risk-stratify patients with prostate cancer to guide treatment decisions. Commercially available tests include Prolaris® (Myriad Genetics, Salt Lake City, UT); OncotypeDx® Prostate Cancer Assay (Genomic Health, Redwood City, CA); ProMark™ Protein Biomarker Test/ProMark™ Risk Score (Metamark Genetics, Cambridge, MA); FoundationOne® CDx (Foundation Medicine, Cambridge, MA); FoundationOne® Liquid CDx (Foundation Medicine, Cambridge, MA); Canis Molecular Intelligence (Canis Life Sciences, Irving, TX); Guardant360 (Guardant Health Inc., Redwood City, CA); ProstateNext® (Ambry Genetics, Aliso Viejo, CA); Color Hereditary Cancer Test (Color Genomics, Burlingame, CA); Invitae Prostate Cancer Panel (Invitae Corp., San Francisco, CA); Prostate Gene (GeneHealth, Cambridge, UK); Myriad myRisk® Hereditary Cancer Test (Myriad Genetics Inc., Salt Lake City, UT) and Decipher® Prostate Cancer Test (GenomeDx Biosciences, San Diego, CA), this latter based on the expression pattern of 22 RNA markers in biopsy or radical prostatectomy specimens. Prolaris®, OncotypeDx®, and Decipher® are tissue-based gene expression tests.

The formulations described herein may be used in methods of treating prostate cancer patients with biochemical recurrence (BCR) or biochemical failure (BF). BCR or BF may be defined by a rise in prostate-specific antigen (PSA) without evidence of disease on imaging. For patients who have received primary radiotherapy, BCR is currently defined as a PSA rise of ≥2.0 ng/mL above the nadir ("Phoenix criteria"). For patients who have received primary surgery, BCR is currently defined as a confirmed PSA rise of ≥2.0 ng/mL above the nadir.

Next generation imaging (NGI), e.g. prostate-specific membrane antigen positron emission tomography (PSMA-PET), may be used to detect lesions not visible on conventional imaging or below the Phoenix threshold, i.e. PSA rise <2.0 ng/mL. NGI may for instance classify some patients with localized prostate cancer, BCR, nmCRPC, or nmHRPC as having metastatic prostate cancer.

The formulations described herein may be used in methods of treating prostate cancer patients with BCR or BF, and which are HRD biomarker positive and/or high risk. The HRD biomarker positive may be at least one of BRCA1, BRCA2, ATM, BRIP1, CDK12, CDK17, CHEK2, FANCA, HDAC2, PALB2, PPP2R2A, RAD51B, and RAD54L.

The formulations described herein may be used in methods of treating BCR or BF, oligometastatic disease, or localized prostate cancer in a patient, which may be detected by conventional imaging.

The formulations described herein may be used in methods of treating BCR or BF, oligometastatic disease, or localized prostate cancer in a patient, which may be detected by NGI.

The formulations described herein may be used in methods of treating patients with locally advanced prostate cancer who are candidates for primary radiotherapy.

The formulations described herein may be used in methods of treating cancer patients, particularly CRPC patients, with circulating tumor cells testing negative for the androgen receptor splice variant 7 (AR-V7). The formulations described herein may be used in methods of treating cancer patients, particularly CRPC patients, with circulating tumor cells testing positive for the androgen receptor splice variant 7 (AR-V7).

The formulations described herein may be used in methods of treating prostate cancer in patients with detectable circulating tumor cells (CTC), circulating DNA, or reduction of plasma DNA. The formulations described herein may be used in methods of treating metastatic prostate cancer in patients with detectable CTCs and/or measurable and non-measurable bony disease or lesions. CTC clearance in patients with metastatic prostate cancer may be established when detecting ≥5 cells per 7.5 mL blood at baseline, detecting <5 cells per 7.5 mL blood at nadir, further confirmed by a second consecutive value obtained 4 or more weeks later.

The free-dose combinations or fixed-dose combinations of abiraterone acetate and niraparib, and optionally a separate composition that comprises a glucocorticoid, for example prednisone, may be administered to a subject, a patient, a mammal, in particular a human, suffering from prostate cancer, primary peritoneal cancer, breast cancer, or ovarian cancer. In one aspect, the human suffering from breast cancer or ovarian cancer is a biomarker-positive patient.

The prostate cancer may be metastatic prostate cancer, advanced prostate cancer, regional prostate cancer, locally advanced prostate cancer, localized prostate cancer, non-metastatic prostate cancer, non-metastatic advanced prostate cancer, non-metastatic regional prostate cancer, non-metastatic locally advanced prostate cancer, non-metastatic localized prostate cancer, hormone-naïve prostate cancer, chemotherapy-naïve prostate cancer, castration-naïve cancer with or without metastases, radiation-naïve prostate cancer, castration-resistant prostate cancer (CRPC), CRPC with DRD, non-metastatic CRPC (nmCRPC), nmCRPC in a patient population with a PSA doubling time equal to or less than 10 months and are HRD positive (or biomarker enriched), nmCRPC in patients having DRD or HRD, nmCRPC in patients having no DRD, nmCRPC in patients with high-risk BCR (e.g. in a DRD+ population), nmCRPC in patients being monitored with new generation imaging techniques (NGI), localized CRPC, locally advanced CRPC, regional CRPC, advanced CRPC, metastatic CRPC (mCRPC), mCRPC in patients having biallelic DNA-repair gene defect (DRD); mCRPC in patients having monoallelic DRD; mCRPC in patients having no DRD; mCRPC in patients having DRD and having received taxane and/or androgen receptor-targeted therapy, CRPC in patients having received hormone therapy (for example enzalutamide, darolutamide, apalutamide), CRPC in patients having received taxane therapy (for example docetaxel, mitoxantrone, cabazitaxel), chemotherapy-naïve CRPC, chemotherapy-naïve mCRPC, hormone-naïve CRPC, hormone-naïve mCRPC, CRPC with progression, CRPC with visceral metastases, CRPC with visceral metastases in patients having received hormone therapy (for example enzalutamide, darolutamide, apalutamide), CRPC with visceral metastases in patients having received taxane therapy (for example docetaxel, mitoxantrone, cabazitaxel), CRPC with visceral metastases and progression, castration-sensitive prostate cancer (CSPC), non-metastatic CSPC (nmCSPC), localized CSPC, locally advanced CSPC, regional CSPC, advanced CSPC, metastatic CSPC (mCSPC), chemotherapy-naïve CSPC, chemotherapy-naïve mCSPC, hormone-naïve CSPC, hormone-naïve mCSPC, hormone-sensitive prostate cancer (HSPC), hormone-dependent prostate cancer, androgen-dependent prostate cancer, androgen-sensitive prostate cancer, biochemically relapsed HSPC, metastatic HSPC (mHSPC), hormone-resistant prostate cancer (HRPC), non-metastatic HRPC (nmHRPC), localized HRPC, locally advanced HRPC, regional HRPC, advanced HRPC, metastatic HRPC (mHRPC), recurrent prostate cancer, prostate cancer with prostate specific antigen (PSA) persistence or recurrence after prostatectomy with or without distant metastases, radiation-resistant prostate cancer, and any combination thereof.

The subject or patient may be in a risk group selected from very low risk, low risk, intermediate favorable risk, intermediate unfavorable risk, high risk, very high risk, and regional risk.

The subject may be surgically castrated or chemically castrated.

Most, but not all, prostate cancers are adenocarcinomas, and the patient may have adenocarcinoma or sarcoma-based prostate cancer. In any of these instances, the prostate cancer may be metastatic.

The patient may have undergone one or more other types of treatment for the prostate cancer prior to the first dose of the free-dose combination or fixed-dose combination of niraparib and abiraterone acetate. For example, the patient may have undergone taxane-based chemotherapy prior to administering the free-dose combination or fixed-dose combination of niraparib and abiraterone acetate. Additionally or alternatively, the patient may have undergone at least one line of androgen receptor-targeted therapy, such as apalutamide (ERLEADA®) and/or enzalutamide (XTANDI®), prior to administering the free-dose combination or fixed-dosed combination of niraparib and abiraterone acetate. In an aspect, the patient does not respond initially or becomes refractory to previous treatments, prior to administering the free-dose or fixed-dosed combination of niraparib and abiraterone acetate. Optionally the glucocorticoid, for example prednisone, can also be administered in addition to the free-dose or fixed-dose combination of niraparib and abiraterone acetate.

The period of time between the end of the other treatment and the administration of the free-dose or fixed-dose combination of niraparib and abiraterone acetate, and optionally plus a glucocorticoid, for example prednisone, in accordance with the present disclosure may be years, months, weeks, days, a single day, or less than 24 hours.

The administration of the free-dose or fixed-dose combination of niraparib and abiraterone acetate, and optionally plus a glucocorticoid, for example prednisone, may be on a once, twice or thrice daily basis.

The daily administration includes administering a single fixed-dose combination (FDC) of niraparib and abiraterone acetate, to the patient one, two or three times per day. Any dosage regimen that is embraced by the preceding description is contemplated. In an aspect, 1 tablet or capsule comprising the FDC of niraparib and abiraterone acetate is administered once daily. In an aspect, 2 tablets or capsules comprising the FDC of niraparib and abiraterone acetate are administered once daily. In an aspect, 3 tablets or capsules comprising the FDC of niraparib and abiraterone acetate are administered once daily. In an aspect, 1 tablet or capsule comprising the FDC of niraparib and abiraterone acetate is administered once daily, at least 1 hour before a meal or at least two hours after a meal. In an aspect, 2 tablets or capsules comprising the FDC of niraparib and abiraterone acetate are administered once daily, at least 1 hour before a meal or at least two hours after a meal. In an aspect, 3 tablets or capsules comprising the FDC of niraparib and abiraterone acetate are administered once daily, at least 1 hour before a meal or at least two hours after meal. In an aspect, 1 tablet or capsule comprising the FDC of niraparib and abiraterone acetate is administered once daily, with water, on an empty stomach at least 1 hour before a meal or at least two hours after meal. In an aspect, 2 tablets or capsules comprising the FDC of niraparib and abiraterone acetate are administered once daily, with water, on an empty stomach at least 1 hour before a meal or at least two hours after meal. In an aspect, 3 tablets or capsules comprising the FDC of niraparib and abiraterone acetate are administered once daily, with water, on an empty stomach at least 1 hour before a meal or at least two hours after a meal.

In an aspect a glucocorticoid is administered once or twice daily. In an aspect prednisone tablets or capsules are administered once or twice daily.

In an aspect, 1 or 2 tablets or capsules comprising the FDC of niraparib and abiraterone acetate are administered once daily and 1 tablet or capsule of a glucocorticoid, for example prednisone is administered once or twice daily.

The amount of niraparib equivalent that is administered to the patient may be about 30 to about 400 mg/day, about 50 to about 350 mg/day, about 66 to about 325 mg/day, about 100 to about 300 mg/day, about 100 to about 275 mg/day, about 125 to about 250 mg/day, about 150 to about 225 mg/day, about 175 to about 225 mg/day, or about 190 to about 210 mg/day, or, about 30, about 33, about 40, about 50, about 60, about 66, about 67, about 70, about 80, about 90, about 99, about 100, about 110, about 120, about 130, about 132, about 134, about 140, about 150, about 160, about 170, about 180, about 190, about 200, about 201, about 210, about 220, about 230, about 240, about 250, about 260, about 270, about 280, about 290, about 300, about 310, about 320, about 330, about 340, or about 350 mg/day.

The amount of abiraterone acetate that is administered to the patient may be about 300 to about 2000 mg/day, about 500 to about 1500 mg/day, about 700 to about 1200 mg/day, about 800 to about 1200 mg/day, about 900 to about 1100 mg/day, about 950 to about 1050 mg/day, or may be about 300, about 333, about 500, about 600, about 666, about 700, about 750, about 800, about 850, about 875, about 900, about 925, about 950, about 999, about 1000, about 1025, about 1050, about 1075, about 1100, about 1125, or about 1500 mg/day.

The amount of prednisone that is administered to the patient may be about 1 to about 25 mg/day, about 2 to about 23 mg/day, about 3 to about 20 mg/day, about 4 to about 18 mg/day, about 5 to about 15 mg/day, about 6 to about 12 mg/day, about 7 to about 11 mg/day, about 8 to about 11 mg/day, about 9 to about 11 mg/day, or may be about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, or about 25 mg/day. In some aspects, the patient has mCSPC and the amount of prednisone is 5 mg/day. In some aspects, the patient has mCRPC and the amount of prednisone is 10 mg/day.

When the FDC of niraparib and abiraterone acetate are administered to a patient, the selected dosage level for each drug will depend on a variety of factors including, but not limited to, the activity of the particular compound, the severity of the individual's symptoms, the route of administration, the time of administration, the rate of excretion of the compound, the duration of the treatment, other drugs, compounds, and/or materials used in combination, and the age, sex, weight, condition, general health, and prior medical history of the patient. The amount of niraparib, the amount of abiraterone acetate, and optionally the amount of prednisone, will ultimately be at the discretion of the physician, although generally the dosage will be to achieve local concentrations at the site of action which achieve the desired effect without causing substantial harmful or deleterious side-effects.

The FDCs may comprise, for example, about 33 to about 350 mg of the niraparib, about 100 to about 1500 mg of the abiraterone acetate.

For example, the instant compositions may include niraparib equivalent in an amount of, for example, 33 to about 350 mg, about 33 to about 300 mg, about 50 to about 200 mg, about 50 to about 150 mg, about 50 to about 100 mg, about 33 to about 100 mg, or may be about 30, about 33, about 50, about 67, about 100, about 110, about 120, about 130, about 140, about 150, about 160, about 170, about 180, about 190, about 200, about 210, about 220, about 230, about 240, about 250, about 260, about 270, about 280, about 290, about 300, about 310, about 320, about 330, about 340, or about 350 mg. The instant compositions may include niraparib equivalent in an amount of about 33, about 50, about 67, or about 100 mg.

The instant compositions may also include abiraterone acetate in an amount of, for example, about 100 to about 1500 mg, about 125 to about 1400 mg, about 150 to about 1300 mg, about 175 to about 1200 mg, about 200 to about 1175 mg, about 225 to about 1150 mg, about 250 to about 1100 mg, about 250 to about 1075 mg, about 250 to about 1050 mg, about 250 to about 1000 mg, about 300 to about 950 mg, about 350 to about 900 mg, about 400 to about 850 mg, about 450 to about 800 mg, or about 500 to about 700 mg, or may be about 100, about 150, about 175, about 200, about 225, about 250, about 275, about 300, about 325, about 350, about 375, about 400, about 450, about 500, about 550, about 600, about 650, about 700, about 750, about 800, about 850, about 900, about 950, about 1000, about 1050, about 1100, about 1150, about 1200, about 1250, about 1300, about 1350, about 1400, about 1450, or about 1500 mg. The instant compositions may include abiraterone in an amount of about 333 or about 500 mg.

The instant compositions may include niraparib equivalent in an amount of about 33 mg and abiraterone in an amount of 333 mg. The instant compositions may include niraparib equivalent in an amount of about 67 mg and abiraterone in an amount of 333 mg. The instant compositions may include niraparib equivalent in an amount of about 50 mg and abiraterone in an amount of 500 mg. The instant compositions may include niraparib equivalent in an amount of about 100 mg and abiraterone in an amount of 500 mg.

The present treatment regimens may also include the separate administration of a glucocorticoid, for example prednisone, in an amount of, for example, about 2 about 15 mg, about 2 to about 14, about 3 to about 13, about 4 to about 12, about 5 to about 11, about 5 to about 10, about 6 to about 11, about 7 to about 11, about 8 to about 11, about 9 to about 11, or may be about 2, about 3, about 4, about 5, about 6, about 7, about 8, about 9, about 10, about 11, about 12, about 13, about 14, or about 15 mg.

The present methods may include administering the FDC of niraparib and abiraterone acetate, and optionally the glucocorticoid or prednisone separately, to the patient over multiple days, weeks, months or years. Preferably, the administration of the FDC of niraparib and abiraterone acetate, occurs on a once, twice or thrice daily basis, and optionally the separate administration of the prednisone occurs on a once, twice, or thrice daily basis. The amount of the niraparib, the abiraterone acetate, and optionally the separately-administered prednisone may be constant over time (i.e., from day to day), or may be increased or decreased over time. For example, the amount of niraparib, the abiraterone acetate, and optionally the separately-administered prednisone, or two or all three of these, that is administered per day may be increased or decreased after one day of administration, after a few days of administration, after a week of administration, and the new dosage amount may be maintained for any desired period of time, e.g., days, weeks, or months, or may subsequently be increased or decreased after the desired interval. In this manner, the present methods may include increasing or decreasing the dosing of the FDC of niraparib and abiraterone acetate (e.g., the amount of niraparib and abiraterone acetate, respectively, that is administered on a once daily basis) at least once over time. The present methods may also or alternatively include increasing or decreasing the dosing of prednisone (e.g., the total amount of the prednisone that is administered on a daily basis) at least once over time. The amount of increase or decrease may be expressed in terms of a percentage, and under such circumstances the amount of a single episode of increase or decrease may be about 5%, about 10%, about 15%, about 20%, about 25%, about 30%, about 35%, about 40%, about 45%, about 50%, about 55%, about 60%, about 65%, about 70%, about 80%, about 85%, about 90%, about 95%, about 100%, or by greater than about 100%.

Described herein are methods for treating a cancer in which a therapeutically effective amount of niraparib, abiraterone acetate, and optionally the separately-administered glucocorticoid, such as prednisone, a prednisolone, hydrocortisone, methylprednisolone, and dexamethasone, are administered to a patient, e.g., a patient in need thereof, in combination with a therapeutically effective amount of at least one additional therapeutic agent including, but not limited to, an anti-cancer agent (for example docetaxel, mitoxantrone, cabazitaxel, cisplatin, carboplatin, oxaliplatin, and etoposide), an immunotherapeutic agent (for example pembrolizumab, sipuleucel-T), bone-targeted therapies (for example denosumab, zoledronic acid, alendronate, radium-223, strontium-89, samarium-153), gonadotropin releasing hormone agonists (GnRHa, including, without being limited to, triptorelin, nafarelin, goserelin, leuprorelin or leuprolide, histrelin, gonadorelin, and buserelin), and hormone therapies (for example nilutamide, flutamide, bicalutamide, goserelin, histrelin, leuprolide, triptorelin, degarelix, enzalutamide, apalutamide, darolutamide, ketoconazole, diethylstilbestrol, estrogens). Such methods can also provide an effective treatment for individuals with a refractory cancer, including individuals who are currently undergoing a cancer treatment. Therefore, the methods may be directed to treating a chemotherapy-resistant prostate cancer in a patient, in which a therapeutically effective amount of niraparib and abiraterone acetate is administered to a patient currently receiving an anti-cancer agent.

Additionally, the methods for treating a cancer described herein may be combined with androgen deprivation therapy (ADT). The methods for treating a cancer described herein may be combined with radiation therapy, preferably in an HRD+ population. In an aspect, the methods for treating a cancer described herein may be combined with ADT and external beam radiation therapy (EBRT). The methods for treating a cancer described herein may be combined with alternative energy sources such as high-intensity focused ultrasound (HIFU), cryosurgery, and laser treatments.

The FDC of the present invention, and a separately administered glucocorticoid (e.g., prednisone, a prednisolone, hydrocortisone, methylprednisolone, or dexamethasone; preferably prednisone or a prednisolone) may be administered to a patient having metastatic prostate cancer. In particular, the FDC of the present invention, and a separately-administered glucocorticoid (e.g., prednisone, a prednisolone, hydrocortisone, methylprednisolone, or dexamethasone; preferably prednisone or a prednisolone) may be administered to a patient having mCRPC, such as first-line (L1) mCRPC (e.g., subjects who have not been treated with any therapy in the metastatic castrate-resistant setting, except for androgen deprivation therapy (ADT) and a limited exposure to abiraterone acetate plus prednisone). The patient may be positive for HRD or not positive for HRD. Preferably the patient is positive for HRD. The metastatic prostate cancer may be confirmed by positive bone scan or metastatic lesions on computed tomography (CT) or magnetic resonance imaging (MRI). The patient may have castrate levels of testosterone ≤50 ng/dL and may be under GnRHa therapy or has undergone bilateral orchiectomy. The patient may continue with GnRHa therapy during the treatment if not surgically castrated. The patient may have an Eastern Cooperative Oncology Group Performance Score (ECOG PS) Grade of 0 or 1.

ADT uses surgery or medicines to lower the levels of androgens made in the testicles, to stop them from fueling prostate cancer cells. ADT includes, without being limited to, surgical castration or orchiectomy; and medical castration like luteinizing hormone-releasing hormone (LHRH) agonists, e.g., leuprolide, goserelin, triptorelin, histrelin; LHRH antagonists; abiraterone acetate; ketoconazole; anti-androgens like flutamide, bicalutamide, nilutamide, enzalutamide, apalutamide, darulotamide; or estrogens.

The FDC of the present invention, and a separately-administered glucocorticoid (e.g., prednisone, a prednisolone, hydrocortisone, methylprednisolone, or dexamethasone; preferably prednisone or a prednisolone) may be administered to a patient having mCSPC, e.g., deleterious germline or somatic homologous recombination repair (HRR) gene-mutated mCSPC. The deleterious germline or somatic HRR gene mutation may be at least one of, without being limited to, BRCA1, BRCA2, ATM, BRIP1, CDK12, CDK17, CHEK2, FANCA, HDAC2, PALB2, PPP2R2A, RAD51B, and RAD54L. The mCSPC may be confirmed by at least one bone lesion(s) on bone scan; the bone metastasis preferably further confirmed by CT or MRI. The mCSPC may be detected by NGI like PSMA-PET. The patient may have an Eastern Cooperative Oncology Group Performance Score (ECOG PS) Grade of less than or equal to 2. The patient may be under androgen deprivation therapy (either medical or surgical castration) and this therapy may have been started within 6 months prior to the FDC plus prednisone (or a prednisolone) treatment, preferably it may have been started at least 14 days prior to the treatment with the FDC plus prednisone (or a prednisolone). Said androgen deprivation therapy may be continued through the FDC plus prednisone (or a prednisolone) treatment. Those patients who have started GnRHa therapy less than 28 days prior to the FDC plus prednisone (or a prednisolone) treatment, preferably are administered a first-generation anti-androgen, preferably for at least 14 days prior to the FDC plus prednisone (or a prednisolone) treatment. Said anti-androgen must be discontinued prior to the start of the FDC plus prednisone (or a prednisolone) treatment. The patient may have received prior docetaxel or cabazitaxel treatment; preferably the patient has received a maximum of 6 cycles of docetaxel therapy; preferably the patient has received the last dose of docetaxel or cabazitaxel within 2 months prior the FDC plus prednisone (or a prednisolone) treatment. Prior to FDC plus prednisone (or a prednisolone) therapy, the patient may have received radiation or surgical intervention to manage symptoms of prostate cancer. Prior to FDC plus prednisone (or a prednisolone) therapy, the patient may have received abiraterone acetate plus glucocorticoid (e.g., prednisone, a prednisolone, hydrocortisone, methylprednisolone, or dexamethasone), preferably during a month prior to FDC plus prednisone (or a prednisolone) therapy. Prior to FDC plus prednisone (or a prednisolone) therapy, the patient may have received treatments for localized prostate cancer, preferably these treatments must have been completed at least 1 year prior to the FDC plus prednisone (or a prednisolone) treatment; for example the patient may have undergone up to 3 years of androgen deprivation therapy; for example the patient may have received radiation therapy, prostatectomy, lymph node dissection, or systemic therapies.

The FDC of the present invention, and a separately administered glucocorticoid (e.g., prednisone, a prednisolone, hydrocortisone, methylprednisolone, or dexamethasone; preferably prednisone or a prednisolone) may be administered to a patient having metastatic castration-resistant prostate cancer (mCRPC), with or without homologous recombination deficiency (HRD) or DRD, and optionally with cyclin dependent kinase 12 (CDK12) pathogenic alterations. The FDC may be low strength: 100 mg eq. niraparib/1000 mg abiraterone acetate, given as 2×FDC tablets (50 mg eq. niraparib/500 mg abiraterone acetate), administered orally as a single dose under modified fasted conditions. The FDC may be regular strength: 200 mg eq. niraparib/1000 mg abiraterone acetate, given as 2×FDC tablets (100 mg eq. niraparib/500 mg abiraterone acetate), administered orally as one daily dose under modified fasted conditions. The patient may be able to continue GnRHa therapy during the FDC plus prednisone (or a prednisolone) treatment if not surgically castrated (i.e., subjects who has not undergone bilateral orchiectomy). The patient may have an Eastern Cooperative Oncology Group Performance Status (ECOG PS) of less than or equal to 1. Prior to the FDC plus prednisone (or a prednisolone) treatment, the patient may have been exposed to anti-androgens including, without being limited to, nilutamide, flutamide, bicalutamide, enzalutamide, apalutamide, darolutamide, or abiraterone acetate; preferably said prior anti-androgen therapy is appropriately washed-out before administering the first dose of FDC plus prednisone or a prednisolone. In the case of bicalutamide, flutamide, and nilutamide, the wash-out time is about 2 weeks. For enzalutamide, the wash-out time is about 8 weeks. For apalutamide, the wash-out time is about 6 weeks.

The FDC of the present invention, and a separately administered glucocorticoid (e.g., prednisone, a prednisolone, hydrocortisone, methylprednisolone, or dexamethasone; preferably prednisone or a prednisolone) may be administered further in combination with leuprorelin acetate (a.k.a. leuprolide acetate), prior to, during, and after radiotherapy, to a patient having high risk and lymph node positive prostate cancer. The radiotherapy may be stereotactic body radiotherapy (SBRT) or ultra-hypofractionated radiotherapy, with a total dose of about 37.5 to 40 Gy.

The FDC of the present invention, and a separately administered glucocorticoid (e.g., prednisone, a prednisolone, hydrocortisone, methylprednisolone, or dexamethasone; preferably prednisone or a prednisolone) may be administered to a patient having castration-naïve prostate cancer, with or without metastases. The patient may be able to continue GnRHa therapy during the FDC plus prednisone (or a prednisolone) treatment if not surgically castrated (i.e., subjects who have not undergone bilateral orchiectomy).

In the disclosed compositions, the niraparib may be present in an amount that is therapeutically effective by itself, the abiraterone acetate may be present in an amount that is therapeutically effective by itself, and optionally the separately-administered prednisone may be present in an amount that is therapeutically effective by itself, or two or more of these conditions may apply. In other examples, the total amount of the niraparib, the abiraterone acetate, and optionally the separately-administered prednisone when considered together may represent a therapeutically effective amount, i.e., the amount of niraparib would not be therapeutically effective by itself, the amount of abiraterone acetate would not be therapeutically effective by itself, and if present, the amount of prednisone would not be therapeutically effective by itself.

Also disclosed herein are kits including a composition that comprises niraparib and abiraterone acetate, and optionally a composition that comprises prednisone, and, an instruction print for administering the compositions to a human patient having prostate cancer. The instruction print may provide instructions for administering the respective compositions once daily, twice daily, or multiple-times daily. For example, the instruction print may provide instructions for administering the composition comprising niraparib and abiraterone acetate to a human patient having prostate cancer on a once daily basis, and optionally for administering the composition comprising prednisone to the human patient on a twice daily basis.

The present disclosure further relates to a method for determining the bioequivalence of a test fixed-dose combination (FDC) formulation of niraparib and abiraterone acetate, relative to an oral dosage form of the present disclosure, said method comprising i) measuring a bioequivalence parameter of the test FDC formulation and optionally measuring a bioequivalence parameter of the oral dosage form of the present disclosure, and ii) comparing the bioequivalence parameter of the test FDC formulation to the corresponding bioequivalence parameter of the oral dosage form of the present disclosure.

In an aspect, the bioequivalence parameter is selected from $AUC_{(0-t)}$, $AUC_{(0-\infty)}$, residual area, $C_{max}$ and $t_{max}$, $AUC_{(0-72\ h)}$, terminal rate constant ($\lambda_z$), $t_{1/2}$, $AUC_{(0-\tau)}$, $C_{max,ss}$, $t_{max,ss}$, $Aer_{(0-t)}$, and $R_{max}$, which bioequivalence parameters are well known to the person skilled in the arts of bioequivalence and pharmacokinetics.

The present invention is further defined in the following examples. It should be understood that these examples, while indicating preferred embodiments of the invention, are given by way of illustration only, and should not be construed as limiting the appended claims. From the above discussion and these examples, one skilled in the art can ascertain the essential characteristics of this invention, and without departing from the spirit and scope thereof, can make various changes and modifications of the invention to adapt it to various usages and conditions.

EXAMPLES

Example 1—Compositions of Formulations

TABLE 1

Composition of abiraterone acetate: niraparib tosylate monohydrate, 500/eq. 50 mg core tablet, prepared according to the procedures of Example 2.1 and 2.2.

| Component | Quality Reference | Function | Quantity per Unit (mg) |
|---|---|---|---|
| Granule composition: | | | |
| Binder Solution: | | | |
| HPMC 2910 15 mPa · s | Ph.Eur | Binder | 22.50 |
| Sodium Lauryl Sulfate | Ph.Eur | Wetting agent | 5.60 |
| Purified Water[a] | Ph.Eur | Solvent[a] | <750.00[a]> |
| Intragranular Phase: | | | |
| Abiraterone acetate | Company Specification | Active | 500.00 |
| Niraparib tosylate monohydrate[b] | Company Specification | Active | 79.70[b] |
| Lactose monohydrate | Ph.Eur | Diluent | 253.20 |
| Crospovidone | Ph.Eur | Disintegrant | 30.00 |
| Extragranular Phase: | | | |
| Silicified Microcrystalline Cellulose | NF | Diluent | 451.70 |
| Crospovidone | Ph.Eur | Disintegrant | 75.00 |
| Sodium Lauryl Sulfate | Ph.Eur | Wetting agent | 56.00 |
| Colloidal Anhydrous Silica | Ph.Eur | Glidant | 11.30 |
| Magnesium Stearate | Ph.Eur | Lubricant | 15.00 |
| Core tablet weight: | | | 1500.00 |

[a]Removed during processing

[b]Salt factor = 1.594; 79.70 mg niraparib tosylate is equivalent to 50.00 mg dose of niraparib (base)

TABLE 2

Composition of abiraterone acetate: niraparib tosylate monohydrate, 500/eq. 50 mg oral film coated tablet of Table 1, prepared according to the procedure of Example 2.3.

| Component | Quality Reference | Function | Quantity per Unit (mg) |
|---|---|---|---|
| Abiraterone acetate: niraparib tosylate monohydrate 500/eq. 50 mg oral tablet of Table 1 | | | 1500.00 |
| Purified Water[a] | Ph.Eur | Processing Agent[a] | <240.00[a]> |
| Opadry ® AMB II 88A620004 Yellow | Company Specification | Coating powder | 60.00 |
| Total Weight: | | | 1560.00 |

[a]Removed during processing

TABLE 3

Composition of abiraterone acetate: niraparib tosylate monohydrate, 500/eq. 100 mg core tablet, prepared according to the procedures of Example 2.1 and 2.2

| Component | Quality Reference | Function | Quantity per Unit (mg) |
|---|---|---|---|
| Granule composition: | | | |
| Binder Solution: | | | |
| HPMC 2910 15 mPa · s | Ph.Eur | Binder | 24.00 |
| Sodium Lauryl Sulfate | Ph.Eur | Wetting agent | 5.60 |
| Purified Water[a] | Ph.Eur | Solvent[a] | <800.00[a]> |
| Intragranular Phase: | | | |
| Abiraterone acetate | Company Specification | Active | 500.00 |
| Niraparib tosylate monohydrate[b] | Company Specification | Active | 159.40[b]. |
| Lactose monohydrate | Ph.Eur | Diluent | 253.20 |
| Crospovidone | Ph.Eur | Disintegrant | 32.00 |
| Extragranular Phase: | | | |
| Silicified Microcrystalline Cellulose | NF | Diluent | 461.80 |
| Crospovidone | Ph.Eur | Disintegrant | 80.00 |
| Sodium Lauryl Sulfate | Ph.Eur | Wetting agent | 56.00 |
| Colloidal Anhydrous Silica | Ph.Eur | Glidant | 12.00 |
| Magnesium Stearate | Ph.Eur | Lubricant | 16.00 |
| Core tablet weight: | | | 1600.00 |

[a]Removed during processing

[b]Salt factor = 1.594; 159.40 mg niraparib tosylate is equivalent to 100.00 mg dose of niraparib (base)

TABLE 4

Composition of abiraterone acetate: niraparib tosylate monohydrate, 500/eq. 100 mg oral film coated tablet of Table 3, prepared according to the procedure of Example 2.3.

| Component | Quality Reference | Function | Quantity per Unit (mg) |
|---|---|---|---|
| Abiraterone acetate: niraparib tosylate monohydrate 500/eq. 100 mg oral tablet of Table 3 | | | 1600.00 |

TABLE 4-continued

Composition of abiraterone acetate: niraparib tosylate monohydrate, 500/eq. 100 mg oral film coated tablet of Table 3, prepared according to the procedure of Example 2.3.

| Component | Quality Reference | Function | Quantity per Unit (mg) |
|---|---|---|---|
| Purified Water[a] | Ph.Eur | Processing Agent[a] | <256.00[a]> |
| Opadry ® AMB II 88A170010 Beige | Company Specification | Coating powder | 64.00 |
| Total Weight: | | | 1664.00 |

[a]Removed during processing

TABLE 5

Composition of abiraterone acetate: niraparib tosylate monohydrate, 333/eq. 33 mg core tablet, prepared according to the procedures of Example 3.1, 3.2 and 3.3.

| Component | Quality Reference | Function | Quantity per Unit (mg) |
|---|---|---|---|
| Internal Phase: | | | |
| Niraparib tosylate monohydrate[a] | Company Specification | Active | 53.13[3] |
| Lactose monohydrate | Ph.Eur | Diluent | 11.56 |
| Microcrystalline Cellulose PH101 | Ph.Eur | Diluent | 37.25 |
| Povidone K30 | Ph.Eur | Binder | 2.22 |
| Crospovidone | Ph.Eur | Disintegrant | 1.11 |
| Colloidal Anhydrous Silica | Ph.Eur | Glidant | 2.78 |
| Magnesium Stearate | Ph.Eur | Lubricant | 0.56 |
| Abiraterone acetate granules[b] | Company Specification | Active | 531.99 |
| External Phase: | | | |
| Silicified Microcrystalline Cellulose (HD90) | NF | Diluent | 533.30 |
| Crospovidone | Ph.Eur | Disintegrant | 65.50 |
| Sodium Lauryl Sulfate | Ph.Eur | Wetting agent | 37.30 |
| Colloidal Anhydrous Silica | Ph.Eur | Glidant | 10.00 |
| Magnesium Stearate | Ph.Eur | Lubricant | 13.30 |
| Core tablet weight: | | | 1300.00 |

[a]Salt factor = 1.594; 53.13 mg niraparib tosylate is equivalent to 33.00 mg dose of niraparib (base)

TABLE 6

Composition of abiraterone acetate: niraparib tosylate monohydrate, 333/eq. 33 mg oral film coated tablet of Table 5, prepared according to the procedure of Example 3.4.

| Component | Quality Reference | Function | Quantity per Unit (mg) |
|---|---|---|---|
| Abiraterone acetate: niraparib tosylate monohydrate 333/eq. 33 mg oral tablet of Table 5 | | | 1300.00 |
| Purified Water[a] | Ph.Eur | Processing Agent[a] | <221.00[a]> |
| Opadry ® AMB II 88A220039 Yellow | Company Specification | Coating powder | 39.00 |
| Total Weight | | | 1339.00 |

[a]Removed during processing

TABLE 7

Composition of abiraterone acetate: niraparib tosylate monohydrate, 333/eq. 67 mg core tablet, prepared according to the procedures of Example 3.1, 3.2 and 3.3.

| Component | Quality Reference | Function | Quantity per Batch (kg) |
|---|---|---|---|
| Internal Phase: | | | |
| Niraparib tosylate monohydrate[a] | Company Specification | Active | 1.063 |
| Lactose monohydrate | Ph.Eur | Diluent | 0.231 |
| Microcrystalline Cellulose PH101 | Ph.Eur | Diluent | 0.745 |
| Povidone K30 | Ph.Eur | Binder | 0.045 |
| Crospovidone | Ph.Eur | Disintegrant | 0.022 |
| Colloidal Anhydrous Silica | Ph.Eur | Glidant | 0.056 |
| Magnesium Stearate | Ph.Eur | Lubricant | 0.011 |
| Abiraterone acetate granules | Company Specification | Active | 5.320 |
| External Phase: | | | |
| Silicified Microcrystalline Cellulose (HD90) | NF | Diluent | 6.109 |
| Crospovidone | Ph.Eur | Disintegrant | 0.755 |
| Sodium Lauryl Sulfate | Ph.Eur | Wetting agent | 0.373 |
| Colloidal Anhydrous Silica | Ph.Eur | Glidant | 0.116 |
| Magnesium Stearate | Ph.Eur | Lubricant | 0.155 |
| Core tablet weight: | | | 15.001 |

[a]Salt factor = 1.594

TABLE 8

Composition of abiraterone acetate: niraparib tosylate monohydrate, 333/eq. 67 mg oral film coated tablet of Table 7, prepared according to the procedure of Example 3.4.

| Component | Quality Reference | Function | Quantity per Batch (kg) (11539 tablets) |
|---|---|---|---|
| Abiraterone acetate: niraparib tosylate monohydrate 333/eq. 67 mg oral tablet of Table 7 | | | 15.00 |
| Purified Water[a] | Ph.Eur | Processing Agent[a] | <2.55[a]> |
| Opadry ® AMB II 88A220039 Yellow | Company Specification | Coating powder | 0.45 |
| Total Weight: | | | 15.45 |

[a]Removed during processing

TABLE 9

Composition of abiraterone acetate: niraparib tosylate monohydrate, 500/eq. 100 mg core tablet prepared according to the procedures of Example 4.1 and 4.2.

| Component | Quality Reference | Function | mg/tablet |
|---|---|---|---|
| Intragranular Phase: | | | |
| Abiraterone acetate | Company Specification | Active | 500 |
| Niraparib tosylate monohydrate[a] | Company Specification | Active | 159.40 |
| Lactose monohydrate | Ph.Eur | Diluent | 110.0 |
| Crospovidone | Ph.Eur | Disintegrant | 40.0 |
| Sodium Lauryl Sulfate | Ph.Eur | Wetting agent | 5.6 |
| Colloidal Anhydrous Silica | Ph.Eur | Glidant | 8.0 |

TABLE 9-continued

Composition of abiraterone acetate: niraparib tosylate monohydrate, 500/eq. 100 mg core tablet prepared according to the procedures of Example 4.1 and 4.2.

| Component | Quality Reference | Function | mg/tablet |
|---|---|---|---|
| Microcrystalline Cellulose PH101 | NF | Diluent | 349.00 |
| Magnesium Stearate | Ph.Eur | Lubricant | 4.0 |
| Extragranular Phase: | | | |
| Silicified Microcrystalline Cellulose | NF | Diluent | 308.0 |
| Crospovidone | Ph.Eur | Disintegrant | 40.0 |
| Sodium Lauryl Sulfate | Ph.Eur | Wetting agent | 56.0 |
| Colloidal Anhydrous Silica | Ph.Eur | Glidant | 8.0 |
| Magnesium Stearate | Ph.Eur | Lubricant | 12.0 |
| Core tablet weight: | | | 1600 |

[a]Salt factor = 1.594

TABLE 10

Composition of abiraterone acetate: niraparib tosylate monohydrate, 500/eq. 100 mg oral film coated tablet of Table 9, prepared according to the procedure of Example 4.3.

| Component | Quality Reference | Function | Quantity per Unit (mg) |
|---|---|---|---|
| Abiraterone acetate: niraparib tosylate monohydrate 500/eq. 100 mg oral tablet of Table 5 | | | 1600.00 |
| Purified Water[a] | Ph.Eur | Processing Agent[a] | <256.00[a]> |
| Opadry ® AMB II 88A170010 Beige | Company Specification | Coating powder | 64.00 |
| Total Weight: | | | 1664.00 |

[a]Removed during processing

TABLE 11

Composition of abiraterone acetate: niraparib tosylate monohydrate, 500/eq. 50 mg core tablet prepared according to the procedures of Example 4.1 and 4.2.

| Component | Quality Reference | Function | mg/tablet |
|---|---|---|---|
| Intragranular Phase: | | | |
| Abiraterone acetate | Company Specification | Active | 500 |
| Niraparib tosylate monohydrate[a] | Company Specification | Active | 79.70 |
| Lactose monohydrate | Ph.Eur | Diluent | 130.0 |
| Crospovidone | Ph.Eur | Disintegrant | 40.0 |
| Sodium Lauryl Sulfate | Ph.Eur | Wetting agent | 5.6 |
| Colloidal Anhydrous Silica | Ph.Eur | Glidant | 8.0 |
| Microcrystalline Cellulose PH101 | NF | Diluent | 408.70 |
| Magnesium Stearate | Ph.Eur | Lubricant | 4.0 |
| Extragranular Phase: | | | |
| Silicified Microcrystalline Cellulose | NF | Diluent | 308.0 |
| Crospovidone | Ph.Eur | Disintegrant | 40.0 |
| Sodium Lauryl Sulfate | Ph.Eur | Wetting agent | 56.0 |

TABLE 11-continued

Composition of abiraterone acetate: niraparib tosylate monohydrate, 500/eq. 50 mg core tablet prepared according to the procedures of Example 4.1 and 4.2.

| Component | Quality Reference | Function | mg/tablet |
|---|---|---|---|
| Colloidal Anhydrous Silica | Ph.Eur | Glidant | 8.0 |
| Magnesium Stearate | Ph.Eur | Lubricant | 12.0 |
| Core tablet weight: | | | 1600 |

[a]Salt factor = 1.594

TABLE 12

Composition of abiraterone acetate: niraparib tosylate monohydrate, 500/eq. 50 mg oral film coated tablet of Table 9, prepared according to the procedure of Example 4.3.

| Component | Quality Reference | Function | Quantity per Unit (mg) |
|---|---|---|---|
| Abiraterone acetate: niraparib tosylate monohydrate 500/eq. 100 mg oral tablet of Table 5 | | | 1600.00 |
| Purified Water[a] | Ph.Eur | Processing Agent[a] | <256.00[a]> |
| Opadry ® AMB II 88A620004 Yellow | Company Specification | Coating powder | 64.00 |
| Total Weight: | | | 1664.00 |

[a]Removed during processing

Example 2—Preparation of a Coated Tablet Comprising Co-Granules of Abiraterone Acetate and Niraparib Tosylate Monohydrate, Prepared by Wet Granulation

2.1 Wet Granulation of Abiraterone Acetate and Niraparib Tosylate Monohydrate A binder solution was made by dissolving HPMC 2910 15 mPa·s and sodium lauryl sulfate in purified water until a clear solution was obtained. The ingredients abiraterone acetate, niraparib tosylate monohydrate, lactose monohydrate, and crospovidone were screened, pre-blended, and transferred into a suitable wet granulation equipment, the fluid bed granulator GPCG30. These ingredients were warmed up while fluidizing. The complete binder solution was sprayed upon the ingredients using the wet granulation technique. The granulate was dried after spraying while fluidizing. The dried powder was collected and packed in aluminum bags.

TABLE 13

Granulometry Results for the granulate resulting from the granulation of the binder solution with the ingredients of the intragranular phase, of the composition of Table 1 and the composition of Table 3

| Parameter | Table 1 | Table 3 |
|---|---|---|
| LOD (%) | 1.46 | 1.41 |
| Angle of repose (°) | 34.73 | 35.07 |
| Bulk density (g/mL) | 0.403 | 0.397 |
| Tapped density (g/mL) | 0.455 | 0.431 |
| $d_{10}$; $d_{50}$; $d_{90}$ (μm) | 230; 403; 726 | 256; 399; 695 |

The LOD profile for the granulates of the compositions of Table 1 and Table 3 is provided in FIG. 6.

The sieve analysis is provided in FIG. 7 for the granulate of Table 1, and in FIG. 8 for the granulate of Table 3.

2.2 Extra-Granular Phase and Compression

Silicified microcrystalline cellulose, crospovidone, sodium lauryl sulfate, and colloidal anhydrous silica were screened, and added to the fluid-bed granulate. All materials were screened and blended in a suitable blender. Magnesium stearate was screened and added to the container, and all materials were again blended in a suitable blender. The blend was then compressed into core tablets using the tablet press Module S (KC11).

The LOD, angle of repose, bulk density, and tapped density of the final blend of the compositions of Table 1 and Table 3 can be found in Table 14.

TABLE 14

LOD, Angle of Repose, and Densities of the Final Blend of the composition of Table 1 and the composition of Table 3

| Parameter | Table 1 | Table 3 |
|---|---|---|
| LOD (%) | 2.57 | 2.37 |
| Angle of repose (°) | 43.46 | 41.22 |
| Bulk density (g/mL) | 0.47 | 0.46 |
| Tapped density (g/mL) | 0.54 | 0.53 |

The blend uniformity (BU) results of the Final Blend of the composition of Table 1 and Table 3 are given in Table 15 and Table 16, while the stratified content uniformity results are presented in Table 17 and Table 18, respectively. The BU results indicate that both blends are well mixed and that both APIs are evenly distributed within the blend. The stratified content uniformity results demonstrate a good and evenly distribution of abiraterone acetate and niraparib tosylate monohydrate within the core tablets during the complete manufacturing process. For the composition of Table 3 also the content uniformity is determined and can be found in Table 19.

TABLE 15

Blend Uniformity Results of the composition of Table 1

| | Abiraterone acetate | Niraparib tosylate monohydrate |
|---|---|---|
| Mean | 100.55 | 100.20 |
| Minimum | 97.19 | 96.88 |
| Maximum | 102.72 | 102.70 |

TABLE 16

Blend Uniformity Results of the composition of Table 3

| | Abiraterone acetate | Niraparib tosylate monohydrate |
|---|---|---|
| Mean | 99.70 | 100.22 |
| Minimum | 94.67 | 95.06 |
| Maximum | 103.42 | 103.84 |

TABLE 17

| Stratified Content Uniformity Results of the composition of Table 1 | | |
|---|---|---|
| | Abiraterone acetate | Niraparib tosylate monohydrate |
| Mean | 102.61 | 102.17 |
| Minimum | 97.66 | 96.99 |
| Maximum | 109.76 | 108.35 |

TABLE 18

| Stratified Content Uniformity Results of the composition of Table 3 | | | |
|---|---|---|---|
| Sample | Abiraterone acetate | Niraparib tosylate monohydrate | Tablet weight (g) |
| Mean | 101.41 | 101.74 | Z |
| Minimum | 97.20 | 97.62 | |
| Maximum | 104.81 | 104.99 | |

TABLE 19

| Content Uniformity Results of the composition of Table 3 | | |
|---|---|---|
| | Abiraterone acetate | Niraparib tosylate monohydrate |
| Mean | 101.32 | 102.18 |
| Stdev | 1.94 | 2.07 |
| RSD | 1.91 | 2.03 |

The resulting tablets were tested for weight, thickness, hardness, and disintegration time, and the results are shown in Table 20. The tablets were collected and packaged in a suitable container.

TABLE 20

| Tablet Weight, Thickness, Hardness and Disintegration Time of the composition of Table 1 and the composition of Table 3 | | | | | |
|---|---|---|---|---|---|
| Composition reference | Sample | Average Weight (min-max) (mg, n = 10) | Average Thickness (min-max) (mm, n = 5) | Average Hardness (min-max) (N, n = 5) | Average Disintegration Time (min-max) (min: sec, n = 6) |
| Table 1 | Sample 1 | 1504.4 (1500.2-1513.6) | 7.81 (7.80-7.83) | 267 (261-273) | 02:59 (02:39-03:13) |
| | Sample 2 | 1506.6 (1502.7-1516.1) | 7.83 (7.82-7.83) | 273 (268-278) | 03:06 (02:57-03:23) |
| | Sample 3 | 1502.7 (1496.8-1513.7) | 7.81 (7.80-7.83) | 266 (262-274) | 02:51 (02:33-03:03) |
| | Sample 4 | 1503.9 (1496.8-1509.8) | 7.81 (7.80-7.82) | 268 (260-274) | 03:07 (02:43-03:25) |
| | Sample 5 | 1505.5 (1496.5-1515.8) | 7.80 (7.80-7.80) | 265 (258-270) | 03:12 (02:55-03:29) |
| Table 3 | Sample 1 | 1608.1 (1597.0-1627.2) | 8.06 (8.06-8.07) | 330 (320-348) | 03:07 (02:47-03:23) |
| | Sample 2 | 1601.7 (1585.3-1614.3) | 8.05 (8.0-8.07) | 321 (311-339) | 03:02 (02:41-03:31) |
| | Sample 3 | 1595.2 (1579.4-1608.2) | 8.06 (8.04-8.07) | 306 (293-318) | 03:36 (03:27-04:05) |
| | Sample 4 | 1597.5 (1580.6-1609.7) | 8.04 (8.03-8.05) | 316 (309-324) | 04:27 (04:09-04:45) |
| | Sample 5 | 1597.9 (1583.8-1608.6) | 8.04 (8.02-8.06) | 316 (299-345) | 03:39 (03:12-04:06) |

All these results indicate that it was possible to successfully manufacture two clinical batches of abiraterone acetate/niraparib tosylate, i.e. the compositions of Tables 1 and 3.

2.3 Film Coating

A coating suspension was prepared by dispersing coating powder in purified water until a suspension was obtained. The core tablets were transferred into a suitable coating pan. The coating solution was then sprayed upon the core tablets using the film coating technique. The film coated tablets were dried, after spraying, in the same coating pan. The coated tablets were collected and packaged in a suitable container.

The resulting film-coated tablets of Table 2 showed no scuffing and no other defects were observed.

The resulting film-coated tablets of Table 4 showed no scuffing defects and no white spots on their surface.

In summary, these film-coated tablets of Tables 2 and 4 were successfully manufactured without defects.

Example 3—Preparation of a Coated Tablet Comprising Granules of Abiraterone Acetate Prepared by Fluid Bed Granulation, and Niraparib Tosylate Monohydrate, the Latter Prepared by Dry Granulation 3.1 Dry Granulation of Niraparib Tosylate Monohydrate Niraparib tosylate monohydrate, lactose monohydrate, microcrystalline cellulose, povidone K30, crospovidone, colloidal anhydrous silica, and magnesium stearate were screened and blended using a suitable blender. Following, the blend was milled and the milled material was further blended with a suitable blender. A dry granulate was made using a suitable compaction technique, e.g. a roller compacter, and the dry granulate was further milled using a suitable dry mill.

3.2 Wet Granulation of Abiraterone Acetate

Abiraterone acetate, lactose monohydrate, and croscarmellose sodium were mixed and optionally sieved. A binder solution comprising hypromellose, sodium lauryl sulfate (SLS) and purified water, was prepared and added to the mixture of abiraterone acetate, lactose monohydrate, and croscarmellose sodium. Granules were then formed by fluid bed granulation and subsequently dried.

3.3 Extra-Granular Phase and Compression

The obtained abiraterone acetate granules and niraparib tosylate monohydrate granules were screened and blended with silicified microcrystalline cellulose, crospovidone, sodium lauryl sulfate, and colloidal anhydrous silica, in a suitable blender. Magnesium stearate was screened and added to the container, and all materials were again blended in a suitable blender.

The blend containing niraparib tosylate monohydrate granules and abiraterone acetate granules was then compressed into core tablets using a suitable tablet press. The tablets were collected and packaged in a suitable container.

3.4 Film Coating

A coating suspension was prepared by dispersing coating powder in purified water until a suspension was obtained. The core tablets were transferred into a suitable coating pan. The coating solution was then sprayed upon the core tablets using the film coating technique. The film coated tablets were dried, after spraying, in the same coating pan. The coated tablets were collected and packaged in a suitable container.

4.1 Dry Granulation of Niraparib Tosylate Monohydrate and Abiraterone Acetate

Abiraterone acetate, niraparib tosylate monohydrate, lactose monohydrate, crospovidone, sodium lauryl sulfate, colloidal anhydrous silica, microcrystalline cellulose, and magnesium stearate were screened and blended using a suitable blender. Following, the blend was milled and the milled material was further blended with a suitable blender. A dry granulate was made using a suitable compaction technique, e.g. a roller compacter, and the dry granulate was further milled using a suitable dry mill.

4.2 Extra-Granular Phase and Compression

The obtained abiraterone acetate and niraparib tosylate monohydrate co-granules were screened and blended with silicified microcrystalline cellulose, crospovidone, sodium lauryl sulfate, and colloidal anhydrous silica, in a suitable blender. Magnesium stearate was screened and added to the container, and all materials were again blended in a suitable blender.

The blend was then compressed into core tablets using a suitable tablet press. The tablets were collected and packaged in a suitable container.

4.3 Film Coating

A coating suspension was prepared by dispersing coating powder in purified water until a suspension was obtained. The core tablets were transferred into a suitable coating pan. The coating solution was then sprayed upon the core tablets using the film coating technique. The film coated tablets were dried, after spraying, in the same coating pan. The coated tablets were collected and packaged in a suitable container.

Example 5—Stability Data of the Prepared Dried Granules of Tables 1 and 3

After preparation of the dried granules of Tables 1 and 3, stability data show no degradation of abiraterone acetate and niraparib tosylate monohydrate. The oxidative degradants for abiraterone acetate remain within specification after 12 months at 5° C., 25° C./60% RH and 30° C./75% RH and after 6 months at 40° C./75% RH.

Example 6—Dissolution Method for Testing In Vitro Release of Active Pharmaceutical Ingredients of Prepared Compositions The parameters of the dissolution methods are summarized in Table 21, below.

TABLE 21

| Parameter | Value |
|---|---|
| Dissolution Apparatus: | Paddle (USP type 2, Ph.Eur, JP.) |
| Dissolution Medium Temperature: | 37.0 ± 0.5° C. |
| Dissolution Medium Volume: | 900 mL |
| Dissolution Medium: | 0.25% (w/v) SLS in 0.05M sodium phosphate buffer pH 4.5 |
| Paddle Rotation Speed: | 75 rpm |
| Sample Filter: | Syringe filter 0.2 μm pore size, regenerated cellulose membrane |
| Analytical Finish: | UHPLC with UV detection at 236 nm |

USP = United States Pharmacopeia; JP = Japan; Ph.Eur. = European Pharmacopoeia; SLS = sodium lauryl sulfate; UHPLC = ultra high-performance liquid chromatography; UV = ultraviolet; w/v = weight/volume.

In vitro dissolution curves for abiraterone acetate and niraparib are provided in FIG. 5A and FIG. 5B, respectively, for a combination of single agents being one capsule of 100-mg eq. niraparib, in its tosylate monohydrate form, and 2 tablets of 250-mg abiraterone acetate;

a FDC tablet with the composition of Table 2 (50-mg eq. niraparib, in its tosylate monohydrate form, and 500-mg abiraterone acetate); and a FDC tablet with the composition of Table 4 (100-mg eq. niraparib, in its tosylate monohydrate form, and 500-mg abiraterone acetate).

Example 7—a Phase 3 Randomized, Placebo-Controlled, Double-Blind Study of Niraparib in Combination with Abiraterone Acetate and Prednisone Versus Abiraterone Acetate and Prednisone for Treatment of Subjects with Metastatic Prostate Cancer, MAGNITUDE The primary objective of this study is to evaluate the effectiveness of niraparib and abiraterone acetate plus prednisone (AAP) compared to abiraterone acetate plus prednisone and placebo, as determined by radiographic progression-free survival (rPFS).

The study consists of 5 phases; a Prescreening Phase for biomarker evaluation only, a Screening Phase, a Treatment Phase, a Follow-up Phase, and an Extension Phase (either Open-label or Long-term, depending on Cohort assignment). A treatment cycle is defined as 28 days.

Cohort 1: Subjects with mCRPC and HRR Gene Alteration

Cohort 1 evaluates the combination of niraparib and AAP versus placebo and AAP in subjects with L1 mCRPC (i.e., have not been treated with any therapy in the metastatic castrate-resistant setting, except for ADT and a limited exposure to AAP) and HRR gene alteration. This cohort enrolls approximately 400 subjects.

Cohort 2: Subjects with mCRPC and No HRR Gene Alteration

Cohort 2 evaluates the combination of niraparib and AAP versus placebo and AAP in subjects with L1 mCRPC (i.e., have not been treated with any therapy in the metastatic castrate-resistant setting, except for ADT and a limited exposure to AAP) and who have no HRR gene alteration. The cohort may enroll approximately 600 subjects. A pre-specified futility analysis was performed after approximately 200 subjects were enrolled and approximately 125 progression events had occurred in this cohort.

Cohort 3: Subjects with mCRPC Receiving the FDC of Niraparib and Abiraterone Acetate To evaluate the clinical efficacy and safety of the FDC tablet formulation of niraparib and abiraterone acetate, a separate open-label cohort has been added to the study (Cohort 3). Up to approximately 100 subjects may be enrolled into Cohort 3 under the same inclusion/exclusion criteria and undergo the same study procedures as Cohort 1, except that subjects in Cohort 3 receive open-label niraparib+abiraterone acetate as an FDC tablet formulation instead of as single agents.

Study Populations

- Intent-to-Treat (ITT) Population: Randomized subjects from both Cohorts 1 and 2.
- Safety Population: Subjects in Cohorts 1 and 2 who receive at least one dose of study drug.
- FDC Population: Subjects in Cohort 3 who receive at least one dose of FDC.

Evaluations

- Efficacy evaluations include the following:
  - Radiographic progression-free survival (rPFS; primary endpoint): evaluated by tumor measurements using CT or Mill scans and whole-body bone scans ($^{99m}$Tc). Scans are collected and reviewed by a central vendor.
  - Serum prostate-specific antigen (measurements at a central laboratory) evaluated by Prostate Cancer Working Group 3 (PCWG3) criteria.
  - Survival status.
  - Subsequent systemic therapy for prostate cancer.
  - Cancer-related radiation therapy or surgical procedures.
  - Symptomatic progression.
  - Patient-reported outcomes.
- PK evaluations. Blood samples to measure plasma levels of niraparib and its metabolite, (if judged relevant), are obtained on Day 1 of Cycles 2 through 7. Population PK parameters and derived exposure are also determined for niraparib. Blood samples to measure plasma levels of abiraterone are obtained pre-dose on Day 1 of Cycles 2 and 3.
- Biomarker evaluations: HRR gene alteration status is evaluated from blood and tumor tissue (archival or recently collected) samples. Other exploratory biomarker analyses are also performed where allowed by local regulations.
- Safety evaluations: Safety assessments are based on medical review of adverse event reports and the results of vital sign measurements, physical examinations, clinical safety laboratory tests, Eastern Cooperative Oncology Group Performance Score, ECG, and other safety evaluations at specified timepoints.

Prescreening Eligibility Criteria

1. Signed informed consent form (ICF).
2. ≥18 years of age (or the local legal age of consent)
3. Histologically confirmed prostate cancer.
4. Can provide a blood sample for determination of HRR gene alterations.
5. Willing to provide a tumor tissue sample (archival or recently collected) for determination of HRR gene alterations selected from BRCA1, BRCA2, CDK12, FANCA, PALB2, CHEK2, BRIP1, HDAC2, and ATM.
6. Metastatic prostate cancer in the setting of castrate levels of testosterone (i.e., taking a gonadotropin releasing hormone analog [GnRHa], or history of bilateral orchiectomy at study entry).

Inclusion Criteria

1. HRR gene alteration status as follows:
   a. Cohort 1: positive for HRR gene alteration
   b. Cohort 2: not positive for HRR gene alteration (i.e., no HRR gene alteration)
   c. Cohort 3: positive for HRR gene alteration and receiving FDC
2. Metastatic disease documented by positive bone scan or metastatic lesions on computed tomography (CT) or magnetic resonance imaging (MRI).
3. Metastatic prostate cancer in the setting of castrate levels of testosterone ≤50 ng/dL on a GnRHa or bilateral orchiectomy as evidenced by prostate-specific antigen (PSA) progression or radiographic progression.
4. Able to continue GnRHa during the study if not surgically castrate.
5. Eastern Cooperative Oncology Group Performance Score (ECOG PS) Grade of 0 or 1
6. Score of ≤3 on the Brief Pain Inventory-Short Form (BPI-SF) Question #3 (worst pain in last 24 hours).
7. Clinical laboratory values at Screening:
   a. Absolute neutrophil count (ANC)≥$1.5\times10^9$/L.
   b. Hemoglobin ≥9.0 g/dL, independent of transfusions for at least 30 days.
   c. Platelet count ≥$100\times10^9$/L.
   d. Serum albumin ≥3.0 g/dL.
   e. Creatinine clearance ≥30 mL/min either calculated or directly measured via 24-hour urine collection.
   f. Serum potassium ≥3.5 mmol/L.
   g. Serum total bilirubin ≤1.5×upper limit of normal (ULN) or direct bilirubin ≤1×ULN (Note: in subjects with Gilbert's syndrome, if total bilirubin is ≥1.5×ULN, measure direct and indirect bilirubin, and if direct bilirubin is ≤1.5×ULN, subject may be eligible as determined by the medical monitor).
   h. Aspartate aminotransferase (AST) and alanine aminotransferase (ALT)≤3×ULN.
8. Able to swallow the study drug tablets and capsules whole.
9. While on study drug and for 3 months following the last dose of study drug, a male subject must agree to use an adequate contraception method as deemed appropriate by the investigator and agree not to donate sperm.
10. Willing and able to adhere to the prohibitions and restrictions specified in this protocol.

Exclusion Criteria

1. Prior treatment with a PARP inhibitor.
2. Systemic therapy (i.e., novel second-generation AR-targeted therapy such as enzalutamide, apalutamide, or darolutamide; taxane-based chemotherapy, or more than 4 months of AAP prior to randomization) in the mCRPC setting; or AAP outside of the mCRPC setting.
3. For subjects who received 2 to 4 months of AAP prior to randomization for the treatment of mCRPC, evidence of progression by PSA (per PCWG3) during screening. These potential subjects are required to have 2 PSA values during the Prescreening and Screening Phases. The second PSA value should be within 2 weeks of randomization. If PSA rise is thought to be due to flare, the investigator should confirm that there is no radiographic progression.

4. Symptomatic brain metastases.
5. History or current diagnosis of myelodysplastic syndrome (MDS)/acute myeloid leukemia (AML).
6. Other prior malignancy (exceptions: adequately treated basal cell or squamous cell skin cancer, superficial bladder cancer, or any other cancer in situ currently in complete remission) ≤2 years prior to randomization, or malignancy that currently requires active systemic therapy.
7. Severe or unstable angina, myocardial infarction or ischemia requiring coronary artery bypass graft or stent within the previous 6 months, symptomatic congestive heart failure, arterial or venous thromboembolic events (e.g., pulmonary embolism, cerebrovascular accident including transient ischemic attacks), or clinically significant ventricular arrhythmias within 6 months prior to randomization or New York Heart Association (NYHA) Class II to IV heart disease.
8. Presence of uncontrolled hypertension (persistent systolic blood pressure [BP] ≥160 mmHg or diastolic BP ≥100 mmHg). Subjects with a history of hypertension are allowed, if BP is controlled to within these limits by anti-hypertensive treatment.
9. Current evidence of any of the following:
   - a. Any medical condition that would make prednisone use contraindicated.
   - b. Any chronic medical condition requiring a higher dose of corticosteroid than 10 mg prednisone (or equivalent) once daily.
10. Active or symptomatic viral hepatitis or chronic liver disease (as evidenced by ascites, encephalopathy, or bleeding disorders secondary to hepatic dysfunction).
11. History of adrenal dysfunction
12. Known allergies, hypersensitivity, or intolerance to AA or niraparib or the corresponding excipients.
13. Subjects who are receiving opioid analgesics at the time of screening.
14. Human immunodeficiency virus (HIV) positive subjects with 1 or more of the following:
    - a. Not receiving highly active antiretroviral therapy.
    - b. Receiving antiretroviral therapy that may interfere with the study drug.
    - c. A change in antiretroviral therapy within 6 months of the start of screening (except if a change is made to avoid a potential drug-drug interaction with the study drug).
    - d. CD4 count <350 at screening.
    - e. An acquired immunodeficiency syndrome-defining opportunistic infection within 6 months of the start of screening.
15. Subjects who have had the following ≤28 days prior to randomization:
    - a. A transfusion (platelets or red blood cells).
    - b. Hematopoietic growth factors.
    - c. An investigational agent for prostate cancer.
    - d. Major surgery (sponsor should be consulted regarding what constitutes major surgery).
    - e. Radiation therapy.

Example 8—a Phase 3 Randomized, Placebo-Controlled, Double-Blind Study of Niraparib in Combination with Abiraterone Acetate and Prednisone Versus Abiraterone Acetate and Prednisone for the Treatment of Participants with Deleterious Germline or Somatic Homologous Recombination Repair (HRR) Gene-Mutated Metastatic Castration-Sensitive Prostate Cancer (mCSPC), AMPLITUDE The objectives of this study are:

- to determine if niraparib and abiraterone acetate, plus prednisone compared with abiraterone acetate plus prednisone in participants with deleterious germline or somatic HRR gene-mutated mCSPC provides superior efficacy in improving radiographic progression-free survival (rPFS);
- to assess the clinical benefit of niraparib and abiraterone acetate, plus prednisone compared with abiraterone acetate plus prednisone in participants with deleterious germline or somatic HRR gene-mutated mCSPC;
- to characterize the safety profile of niraparib and abiraterone acetate, plus prednisone compared with abiraterone acetate plus prednisone in participants with deleterious germline or somatic HRR gene-mutated mCSPC.

Approximately 788 participants are randomly assigned in a 1:1 ratio to either niraparib 200 mg, and abiraterone acetate 1000 mg, plus prednisone 5 mg daily; or abiraterone acetate 1000 mg plus prednisone 5 mg daily. All participants must be receiving background androgen deprivation therapy (ADT; i.e., gonadotropin-releasing hormone analogue or surgical castration). The study consists of 4 phases: a Prescreening Phase for biomarker evaluation for eligibility only, a Screening Phase, a Treatment Phase, and a Follow-up Phase.

Inclusion Criteria

1. Each potential participant must satisfy all of the following criteria to be enrolled in the study:
2. >18 years of age (or the local legal age of consent).
3. Diagnosis of prostate adenocarcinoma.
4. Metastatic disease documented by ≥1 bone lesion(s) on $^{99m}$Tc bone scan. Participants with
5. a single bone lesion must have confirmation of bone metastasis by CT or MM.
6. Must have at least one of the deleterious germline or somatic HRR gene alterations selected from BRCA1, BRCA2, BRIP1, CDK12, CHEK2, FANCA, PALB2, RAD51B, and RAD54L.
7. Eastern Cooperative Oncology Group Performance Status (ECOG PS) Grade <2.
8. Androgen deprivation therapy (either medical or surgical castration) must have been started >14 days prior to randomization and willing to continue through the treatment phase. Participants who start a GnRH agonist <28 days prior to randomization are required to take a first-generation anti-androgen for >14 days prior to randomization. The anti-androgen must be discontinued prior to randomization.
9. Participants who have received prior docetaxel treatment must meet the following criteria:
   - a. Received a maximum of 6 cycles of docetaxel therapy for mCSPC
   - b. Received the last dose of docetaxel <2 months prior to randomization c. Maintained a response to docetaxel of stable disease or better, by investigator assessment of imaging or PSA, prior to randomization.

10. Other allowed prior therapy for mCSPC:
 a. Maximum of 1 course of radiation or surgical intervention to manage symptoms of prostate cancer. Radiation with curative intent is not allowed. Radiation must be completed prior to randomization.
 b. <6 months of ADT prior to randomization.
 c. 30 days of abiraterone acetate plus prednisone allowed if required.

11. Allowed prior treatments for localized prostate cancer (all treatments must have been completed ≥1 year prior to randomization):
 a. ≤3 years total of ADT
 b. All other forms of prior therapies including radiation therapy, prostatectomy, lymph node dissection, and systemic therapies.

12. Clinical laboratory values at Screening:
 a. Absolute neutrophil count $\geq 1.5\times10^9$/L
 b. Hemoglobin ≥9.0 g/dL, independent of transfusions for at least 28 days
 c. Platelet count $\geq 100\times10^9$/L
 d. Creatinine <2×upper limit of normal (ULN)
 e. Serum potassium ≥3.5 mmol/L
 f. Serum total bilirubin ≤1.5×ULN or direct bilirubin ≤1×ULN (Note: In participants with Gilbert's syndrome, if total bilirubin is ≥1.5×ULN, measure direct and indirect bilirubin, and if direct bilirubin is ≤1.5×ULN, participant may be eligible)
 g. AST or ALT ≤3×ULN 13. Able to swallow the study medication tablets whole.

14. Must sign informed consent (written or remote/virtual) indicating that he understands the purpose of, and procedures required for, the study and is willing to participate in the study including providing a DNA sample.

15. While on study medication and for 3 months following the last dose of study medication, a male participant must agree to use an adequate contraception method as deemed appropriate by the investigator.

16. A male participant must agree not to donate sperm while on study treatment and for a minimum of 3 months following the last dose of study medication.

Exclusion Criteria

Any potential participant who meets any of the following criteria is excluded from participating in the study:

1. Pathological finding consistent with small cell ductal or neuroendocrine carcinoma of the prostate.
2. Prior treatment with a PARP inhibitor.
3. Prior AR-targeted therapy (e.g., ketoconazole for prostate cancer, apalutamide, enzalutamide, darolutamide), immunotherapy, or radiopharmaceutical agents with the exception of only 30 days of abiraterone acetate plus prednisone allowed prior to randomization.
4. Initiation of treatment with a bisphosphonate or denosumab for the management of bone metastasis <28 days prior to randomization.
5. History of adrenal dysfunction 6. Long-term use of systemically administered corticosteroids (>5 mg of prednisone or the equivalent) during the study is not allowed. Short-term use (<4 weeks, including taper) and locally administered steroids (e.g., inhaled, topical, ophthalmic, and intra-articular) are allowed, if clinically indicated.

7. Active malignancies (i.e., progressing or requiring treatment change in the last 24 months) other than the disease being treated under study. The only allowed exceptions are:
 a. non-muscle invasive bladder cancer;
 b. skin cancer (non-melanoma or melanoma) treated within the last 24 months that is considered completely cured;
 c. breast cancer—adequately treated lobular carcinoma in situ or ductal carcinoma in situ;
 d. malignancy that is considered cured with minimal risk of recurrence.

8. History or current diagnosis of MDS/AML.

9. Current evidence within 6 months prior to randomization of any of the following: severe/unstable angina, myocardial infarction, symptomatic congestive heart failure, clinically significant arterial or venous thromboembolic events (e.g., pulmonary embolism), or clinically significant ventricular arrhythmias.

10. Presence of sustained uncontrolled hypertension (systolic blood pressure >160 mm Hg or diastolic blood pressure >100 mm Hg). Participants with a history of hypertension are allowed, provided that blood pressure is controlled to within these limits by an antihypertensive treatment.

11. Known allergies, hypersensitivity, or intolerance to the excipients of niraparib, abiraterone acetate, or niraparib/abiraterone acetate FDC.

12. Current evidence of any medical condition that would make prednisone use contraindicated.

13. Received an investigational intervention (including investigational vaccines) or used an invasive investigational medical device within 30 days before the planned first dose of study medication.

14. Participants who have had the following ≤28 days prior to randomization:
 a. A transfusion (platelets or red blood cells);
 b. Hematopoietic growth factors;
 c. Major surgery (sponsor should be consulted regarding what constitutes major surgery).

15. Human immunodeficiency virus positive participants with 1 or more of the following:
 a. Not receiving highly active antiretroviral therapy or on antiretroviral therapy for less than 4 weeks.
 b. Receiving antiretroviral therapy that may interfere with the study medication (consult the sponsor for review of medication prior to enrollment).
 c. A change in antiretroviral therapy within 6 months of the start of screening (except if, after consultation with the sponsor on exclusion criterion, a change is made to avoid a potential drug-drug interaction with the study medication).
 d. CD4 count <350 at screening.
 e. An acquired immunodeficiency syndrome-defining opportunistic infection within 6 months of the start of screening.
 f. Human immunodeficiency virus load >400 copies/mL.

16. Active or symptomatic viral hepatitis or chronic liver disease; encephalopathy, ascites or bleeding disorders secondary to hepatic dysfunction.

17. Severe hepatic impairment Class C per Child-Pugh classification system.

The invention claimed is:

1. A method for the treatment of prostate cancer in a male human patient, said method comprising administering to the patient an effective amount of a pharmaceutical formulation comprising abiraterone acetate and niraparib tosylate monohydrate, plus prednisone, wherein the patient has received or continues with gonadotropin releasing hormone agonists (GnRHa) therapy, or has undergone bilateral orchiectomy, prior to the treatment with the pharmaceutical formulation, plus prednisone.

2. The method of claim 1, wherein the prostate cancer is mCRPC.

3. The method of claim 1, wherein the mCRPC is first-line (L1) mCRPC.

4. The method of claim 1, wherein the patient is positive for homologous recombination deficiency (HRD), or the patient is not positive for HRD.

5. The method of claim 4, wherein the HRD status is detected by monoallelic or biallelic alterations in one or more DNA repair genes comprising BRCA1 (Breast Cancer gene 1), BRCA2 (Breast Cancer gene 2), ATM (ataxia-telangiectasia mutated), FANCA (Fanconi Anemia Complementation Group A gene), PALB2 (Partner and Localizer of BRCA2 gene), CHEK2 (Checkpoint Kinase 2 gene), BRIP1 (BRCA1 Interacting Protein C-terminal Helicase 1 gene), HDAC2 (Histone deacetylase 2), or CDK12 (Cyclin Dependent Kinase 12).

6. The method of claim 1, wherein the patient continues with the GnRHa therapy during the treatment with the pharmaceutical formulation, plus prednisone, if not surgically castrated.

7. A method for the treatment of mCRPC, with or without DNA-repair gene defects (DRD) or HRD in a male human patient, said method comprising administering to the patient an effective amount of a pharmaceutical formulation comprising abiraterone acetate and niraparib tosylate monohydrate, plus prednisone, wherein the mCRPC is also with cyclin dependent kinase 12 (CDK12) pathogenic alterations.

8. A method for the treatment of mCRPC, with or without DNA-repair gene defects (DRD) or HRD in a male human patient, said method comprising administering to the patient an effective amount of a pharmaceutical formulation comprising abiraterone acetate and niraparib tosylate monohydrate, plus prednisone, wherein the patient continues with gonadotropin releasing hormone agonists (GnRHa) therapy during the treatment with the pharmaceutical formulation plus prednisone, if not surgically castrated.

9. A method for the treatment of mCRPC, with or without DNA-repair gene defects (DRD) or HRD in a male human patient, said method comprising administering to the patient an effective amount of a pharmaceutical formulation comprising abiraterone acetate and niraparib tosylate monohydrate, plus prednisone, wherein the patient continues with gonadotropin releasing hormone agonists (GnRHa) therapy during the treatment with the pharmaceutical formulation plus prednisone, if not surgically castrated, and wherein the patient has been exposed to anti-androgens selected from nilutamide, flutamide, bicalutamide, enzalutamide, apalutamide, darolutamide, and abiraterone acetate; prior to the treatment with the pharmaceutical formulation plus prednisone.

10. A method for the treatment of mCRPC, with or without DNA-repair gene defects (DRD) or HRD in a male human patient, said method comprising administering to the patient an effective amount of a pharmaceutical formulation comprising abiraterone acetate and niraparib tosylate monohydrate, plus prednisone, wherein the patient has been exposed to anti-androgens selected from nilutamide, flutamide, bicalutamide, enzalutamide, apalutamide, darolutamide, and abiraterone acetate; prior to the treatment with the pharmaceutical formulation plus prednisone, wherein said anti-androgens are washed-out prior to the treatment with the pharmaceutical formulation plus prednisone.

11. The method of claim 1, wherein said pharmaceutical formulation is a free-dose combination (FrDC) of abiraterone acetate and niraparib; or a FrDC of abiraterone acetate and niraparib tosylate monohydrate.

12. The method of claim 1, wherein said pharmaceutical formulation is a fixed-dose combination (FDC) comprising abiraterone acetate and niraparib; or a FDC comprising abiraterone acetate and niraparib tosylate monohydrate.

13. The method of claim 11, wherein the FrDC or FDC comprise, each independently, about 50 mg niraparib eq. and about 500 mg abiraterone acetate; about 100 mg niraparib eq. and about 500 mg abiraterone acetate; about 50 mg niraparib eq. and about 375 mg abiraterone acetate; about 100 mg niraparib eq. and about 375 mg abiraterone acetate; about 50 mg niraparib eq. and about 250 mg abiraterone acetate; about 100 mg niraparib eq. and about 250 mg abiraterone acetate; about 33 mg niraparib eq. and about 333 mg abiraterone acetate; or about 67 mg niraparib eq. and about 333 mg abiraterone acetate.

14. The method of claim 11, wherein the FrDC or FDC are oral dosage forms.

15. The method of claim 14, wherein the oral dosage form is a tablet, a capsule, or a sachet.

16. The method of claim 1, wherein the patient is positive for homologous recombination deficiency (HRD) and the HRD status is detected by monoallelic or biallelic alterations in one or more DNA repair genes comprising BRCA1 (Breast Cancer gene 1) and BRCA2 (Breast Cancer gene 2).

17. The method of claim 8, wherein the patient is positive for homologous recombination deficiency (HRD) and the HRD status is detected by monoallelic or biallelic alterations in one or more DNA repair genes comprising BRCA1 (Breast Cancer gene 1) and BRCA2 (Breast Cancer gene 2).

18. The method of claim 9, wherein the patient is positive for homologous recombination deficiency (HRD) and the HRD status is detected by monoallelic or biallelic alterations in one or more DNA repair genes comprising BRCA1 (Breast Cancer gene 1) and BRCA2 (Breast Cancer gene 2).

* * * * *